US008648086B2

(12) United States Patent
Jiang et al.

(10) Patent No.: US 8,648,086 B2
(45) Date of Patent: Feb. 11, 2014

(54) 5,6-BICYCLIC HETEROARYL-CONTAINING UREA COMPOUNDS AS KINASE INHIBITORS

(75) Inventors: Shan Jiang, Trumbull, CT (US); Xinglong Xing, Suzhou (CN); Qishan Wang, Pleasenton, CA (US); Ren Kong, Suzhou (CN)

(73) Assignee: Ascepion Pharmaceuticals, Inc., Suzhou (CN)

( * ) Notice: Subject to any disclaimer, the term of this patent is extended or adjusted under 35 U.S.C. 154(b) by 48 days.

(21) Appl. No.: 12/922,527

(22) PCT Filed: Aug. 20, 2010

(86) PCT No.: PCT/CN2010/076199
§ 371 (c)(1),
(2), (4) Date: Mar. 29, 2011

(87) PCT Pub. No.: WO2011/023081
PCT Pub. Date: Mar. 3, 2011

(65) Prior Publication Data
US 2012/0122895 A1    May 17, 2012

Related U.S. Application Data

(60) Provisional application No. 61/236,274, filed on Aug. 24, 2009.

(51) Int. Cl.
*A61K 31/52* (2006.01)
*C07D 513/02* (2006.01)

(52) U.S. Cl.
USPC ............... 514/263.1; 514/300; 514/265.1; 546/113; 544/280

(58) Field of Classification Search
USPC ............... 514/263.1, 300, 265.1; 546/113; 544/280
See application file for complete search history.

(56) References Cited

U.S. PATENT DOCUMENTS

| | | | |
|---|---|---|---|
| 5,541,229 A | 7/1996 | Narr et al. | |
| 5,663,346 A | 9/1997 | Buzzetti et al. | |
| 6,300,325 B1 | 10/2001 | Widdowson et al. | |
| 6,525,067 B1 * | 2/2003 | Chen | 514/311 |
| 7,015,233 B2 | 3/2006 | Gomtsyan et al. | |
| 7,074,805 B2 | 7/2006 | Lee et al. | |
| 7,799,782 B2 * | 9/2010 | Munson et al. | 514/234.5 |
| 2003/0158188 A1 | 8/2003 | Lee et al. | |
| 2005/0037999 A1 | 2/2005 | La Greca et al. | |
| 2005/0288290 A1 | 12/2005 | Borzilleri et al. | |
| 2006/0004006 A1 | 1/2006 | Borzilleri et al. | |
| 2006/0035898 A1 | 2/2006 | Arnold et al. | |
| 2006/0040947 A1 | 2/2006 | Blurton et al. | |
| 2006/0128689 A1 | 6/2006 | Gomtsyan et al. | |
| 2006/0199846 A1 | 9/2006 | Mitchell et al. | |
| 2006/0270702 A1 | 11/2006 | Mitchell et al. | |
| 2007/0078156 A1 | 4/2007 | Fletcher et al. | |
| 2007/0099954 A1 | 5/2007 | Gomtsyan et al. | |
| 2007/0287711 A1 | 12/2007 | Arnold et al. | |
| 2008/0182844 A1 | 7/2008 | Bjergarde et al. | |
| 2009/0076046 A1 | 3/2009 | Zhang et al. | |

FOREIGN PATENT DOCUMENTS

| | | |
|---|---|---|
| EP | 0795556 A1 | 9/1997 |
| WO | WO 00/76501 A1 | 12/2000 |
| WO | WO 2005/062795 A2 | 7/2005 |
| WO | WO 2005/103050 A2 | 11/2005 |
| WO | WO 2006/004636 A2 | 1/2006 |
| WO | WO 2006/009755 A2 | 1/2006 |

(Continued)

OTHER PUBLICATIONS

Drizin Irene, et al., Structure-activity studies of a novel series of 5,6-fused heteroaromatic ureas as TRPV1-antagonists, Bioorganic & Medicinal Chemistry, 2006, p. 4740-4749, Issue 14(14), publisher Elsevier B.V., [[[[Netherlands]]]].

Ries Uwe J., 6-Substituted benzimidazoles as new nonpeptide angiotensin II receptor antagonists synthesis biological activity and structure-activity relationships, Journal of Medicinal Chemistry, 1993, p. 4040-4051, Issue 36 (25), publisher American Chemical Society, United States.

*Primary Examiner* — Rei-tsang Shiao
(74) *Attorney, Agent, or Firm* — Weisun Rao; Greenberg Traurig, LLP

(57) ABSTRACT

The present invention provides 5,6-bicyclic heteroaryl-containing urea compounds of Formula I or II and use of the same for treating conditions mediated by protein kinase such as VEGFR2, c-Met, PDGFRβ c-Kit, CSF1R, or EphA2.

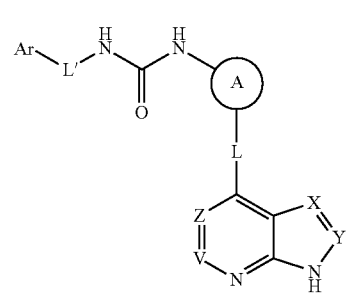

I

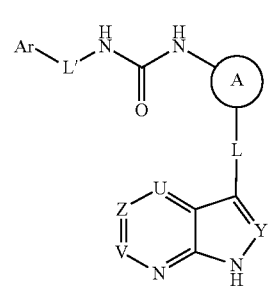

II

35 Claims, No Drawings

(56) References Cited

FOREIGN PATENT DOCUMENTS

| | | |
|---|---|---|
| WO | WO 2006/009797 A1 | 1/2006 |
| WO | WO 2006/069080 A2 | 6/2006 |
| WO | WO 2006/090261 A1 | 8/2006 |
| WO | WO 2007/002325 A1 | 1/2007 |
| WO | WO 2007002433 A1 | 1/2007 |
| WO | WO 2007/013896 A2 | 2/2007 |
| WO | WO 2007/076348 A2 | 7/2007 |
| WO | WO 2007/090141 A2 | 8/2007 |
| WO | WO 2007/121662 A1 | 11/2007 |
| WO | WO 2008/063888 A2 | 5/2008 |
| WO | WO 2008/064255 A2 | 5/2008 |
| WO | WO 2008/064265 A2 | 5/2008 |
| WO | WO 2008/079903 A1 | 7/2008 |
| WO | WO 2008/079906 A1 | 7/2008 |
| WO | WO 2008/079909 A1 | 7/2008 |

* cited by examiner

5,6-BICYCLIC HETEROARYL-CONTAINING UREA COMPOUNDS AS KINASE INHIBITORS

CROSS REFERENCE TO RELATED APPLICATIONS

This application is a national phase application and claims the benefit, under 35 U.S.C. §371, of PCT/CN2010/076199, filed on Aug. 20, 2010, which in turn claims the priority of U.S. Provisional Application No. 61/236,274, filed on Aug. 24, 2009. Both applications are incorporated herein by reference in their entireties.

BACKGROUND OF THE INVENTION

Protein kinases constitute the largest family of human enzymes, encompassing well over 500 proteins. It has been found that kinases play a key role in many basic biological processes in the cell including but not limited to cell proliferation, survival, motility, morphogenesis, angiogenesis, and so on. In addition, many kinases were found involved and implicated in a number of pathological settings such as cancers, autoimmune and inflammatory diseases, eye diseases, and cardiovascular diseases. In general, kinases transmit cell-to-cell or intracellular signals by phosphorylating downstream proteins in the signal transduction pathways such that the downstream proteins are activated and thus signals can be passed from one step to the next down the signaling cascade. These signal transduction pathways are well regulated in the cell under normal physiological conditions. They are activated and shut down appropriately in response to the changes in the intra- and extracellular environments. However, in many pathological settings, one or more signal transduction pathways are often shown to be overactive and responsible for the occurrence and the progression of the diseases. Thus, blocking kinase function in disease settings by chemical or biological agents leading to the disruption of signaling pathways involved in the pathological processes could potentially disrupt or reduce the progression of the diseases and, therefore, confer clinical benefits to the relevant patients. Among many disease-related kinases, receptor tyrosine kinases c-Met (HGF/SF receptor), VEGFR2 (KDR, Flk1), PDGFRβ and c-Kit have been well characterized and considered effective targets for therapies treating diseases such as cancers, autoimmune and inflammatory diseases, and eye diseases. See, e.g., Carmeliet, P., Nature, 2005, 438:932-936; Ferrara, N. et al., Nature, 2005, 438: 967-974; Comoglio, P. M. et al., Nature Reviews: Drug Discovery, 2008, 7: 504-516.

Angiogenesis, the formation of new blood vessels from preexisting ones, plays a significant role in many pathological settings, including cancer, chronic inflammation, diabetic retinopathy, psoriasis, rheumatoid arthritis, and macular degeneration. Anti-angiogenesis therapy represents an important approach for the treatment of solid tumors and other diseases associated with dysregulated vascularization. Given a continuous string of approvals of angiogenesis inhibitor drugs such as bevacizumab, sorafenib, and sunitinib for the treatment of cancers, the clinical benefit from anti-angiogenesis therapy has become increasingly evident. See, e.g., Atkins, M. et al., Discovery, 2006, 5: 279-280; Wilhelm, S. et al., Nature Reviews: Drug Discovery, 2006, 5: 835-844.

The process of angiogenesis requires the concerted actions of multiple angiogenesis mediators as well as the participation of different cell types. Key angiogenesis mediators have been identified, including VEGF, FGF, and angiopoietin 1 and 2 (Ang1 and Ang2) that bind to their cognate receptors (VEGFRs, FGFRs and Tie1 and Tie2, respectively) expressed on endothelial cells, as well as platelet-derived growth factor (PDGF) that binds to its receptor (PDGFRα) expressed on VEGF-producing stromal cells or its receptor (PDGFRβ) expressed on pericytes and smooth muscle cells. Molecules including VEGF, FGF, PDGF, VEGFRs, FGFRs, PDGFRs, Tie1, and Tie2 are key components of multiple different signaling pathways that function in parallel to regulate angiogenesis in both physiological and clinical settings. Among these molecules, the signal transduction pathway mediated by VEGFR2 plays the most critical role in tumor angiogenesis.

A number of monoclonal antibodies (mAbs) against single angiogenesis pathway components such as VEGF and FGF have been developed to block angiogenesis and shown to slow down tumor growth in preclinical and clinical studies. However, to a linear pathway, targeting a single component of the pathway is less effective than simultaneous blocking multiple components of the pathway. Thus development of multiplex small molecular kinase inhibitors is desirable for achieving more efficient angiogenesis inhibition. Since VEGFR2 and PDGFRβ are targeted by both sorafenib and sunitinib, the clinical benefits demonstrated in the use of both drugs unambiguously validate VEGFR2 and/or PDGFRβ kinase as effective target in the treatment of diseases such as cancer. See, e.g., Atkins, M. et al., supra; Wilhelm, S. et al., supra.

The c-Kit proto-oncogene, also known as KIT, CD-117, stem cell factor receptor, or mast cell growth factor receptor, is a receptor tyrosine kinase and a member of the split kinase domain subfamily. Activation of c-Kit by its natural ligand, stem cell factor (SCF), promotes receptor dimerization and autophosphorylation at tyrosine residues Tyr567 and Tyr719. See, e.g., Chian R. et al, Blood, 2001, 98: 1365-1373. Signaling through c-Kit plays an important role in cellular transformation and differentiation, including proliferation, survival, adhesion, and chemotaxis. See, e.g., Linnekin D., Int. J. Biochem. Cell Biol., 1999, 31: 1053-1074. C-Kit expression has been reported in a wide variety of human malignancies such as small cell lung cancer (SCLC), gastrointestinal stromal tumors (GIST), colorectal cancer and so on. As a well proven target in cancer therapy, c-Kit inhibitor such as Gleevec® has been used to treat CML, GIST, and other cancers.

C-Met tyrosine kinase is a cell surface receptor normally activated by its natural ligand, hepatocyte growth factor/scatter factor (HGF/SF). Upon HGF binding, c-Met protein is activated by autophosphorylation and recruits downstream effectors to its cytoplasmic domain. The resulting multi-protein signaling complex can in turn activate a number of downstream intracellular signaling events in epithelial cells and lead to a wide range of cellular responses including but not limited to proliferation, survival, angiogenesis, wound healing, tissue regeneration, scattering, motility and invasion. See, e.g., Comoglio, P. M. et al., supra; and Benvenuti, S, and Comoglio, P. M., J. Cellular Physiology, 2007, 213: 316-325.

Numerous evidences have implicated c-Met as one of the leading molecular targets in cancer therapy. See, e.g., Knudsen, B. S. et al., Current Opinion in Genetics & Development, 2008, 18: 87-96. C-Met has been implicated as a proto-oncogene, which is found genomically amplified, over-expressed, mutated, or aberrantly activated in many types of cancers, suggesting its roles in the tumor growth, invasiveness and metastasis. In addition, elevated c-Met activation has been found in solid tumors which develop resistance to anti-EGFR therapies during the course of treatment, implicating a compensatory role of c-Met activation to the EGFR signaling pathway (see, e.g., Smolen, G. A et al., Proc. Natl. Acad. Sci. USA, 2006, 103: 2316-2321; Lutterbach, B. et al., Cancer Res., 2007, 67: 2081-2088). Thus inhibition of c-Met signaling is considered as a potentially effective therapeutic strategy against solid tumors whose growth is wholly or partially c-Met driven (see, e.g., Smolen, G. A et al., supra). It is thus pharmacologically preferable to develop small molecule kinase inhibitors against c-Met for the treatment of cancer.

Studies have reported that anti-angiogenesis therapies can lead to increased local invasion and distal metastasis of tumor cells and thus elicit malignant progression of tumors (see, e.g., Ebos, J. M. L. et al., Cancer Cell, 2009, 15: 232-239; Paez-Ribes, M. et al., Cancer Cell, 2009, 15: 220-231). This unexpected yet important finding calls for a new generation of anti-angiogenesis therapies which can not only disrupt tumor angiogenesis and arrest tumor growth but also are able to prevent tumor invasion and metastasis at the same time. Due to the important roles that c-Met plays in tumor invasiveness and metastasis, it is strongly conceivable that simultaneous inhibition of VEGF/VEGFR2 and c-Met signaling pathways will produce better clinical outcomes than the current generation of anti-angiogenesis therapy in solid tumor treatment (see, e.g., Loges, S. et al., Cancer Cell, 2009, 15: 167-170).

This invention provides a solution by combining two anti-tumor therapeutic mechanisms with small molecule drugs targeting one or more protein kinases (e.g., both VEGFR2 and c-Met), which offer unexpected clinical advantages over the currently available anti-angiogenesis therapeutics.

BRIEF DESCRIPTION OF THE INVENTION

The present invention in general provides compounds of Formula I or II, and methods of using these compounds for the treatment of conditions mediated by one or more protein kinases (e.g., VEGFR2 or c-Met or PDGFβ or c-Kit or CSF1R, or EphA2, or any of their combinations) such as tumor, rheumatoid arthritis, autoimmune disease, acute inflammation, nephritis, diabetic retinitis, psoriasis, or macular degeneration.

In one aspect, the present invention provides compounds of Formula I or II, crystal forms, chelates, non-covalent complexes, prodrugs, stereoisomers, solvates, N-oxides, pharmaceutically acceptable salts, and mixtures thereof.

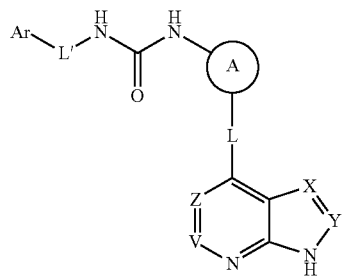

I

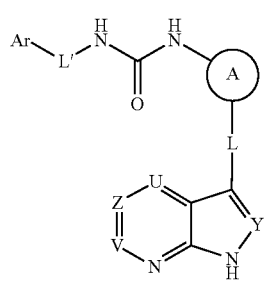

II

In Formula I or II:
U, V, X, Y, and Z are each independently N or C—$R^1$;
L is O, $S(O)_n$, N—$R^2$, or alkylene which is optionally substituted with one or more independent $R^3$ group;
$R^2$ is H, alkyl, aryl, heteroaryl, —C(=O)-alkyl, —C(=O)-aryl, or —C(=O)-heteroaryl, each of which is optionally substituted with one or more independent $Q^1$ groups;
L' is a covalent bond, —C(=O)—, —C(=O)-alkylene, or alkylene, each of which is optionally substituted with one or more independent $R^4$ group;
A is

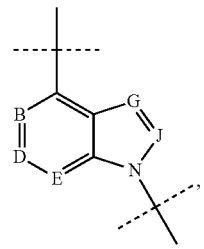

A1

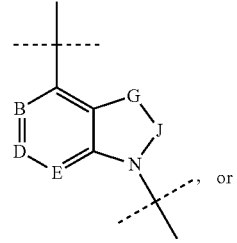

A2 or

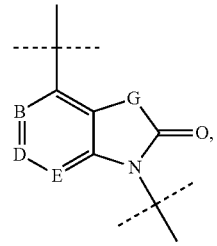

A3 wherein B, D, E, G, and J are each independently N or C—$R^5$; the 5-membered ring of A is connected to L and the 6-membered ring of A is connected to the urea group in Formula I or II; in other words, the fixed nitrogen in A as shown in A1, A2, and A3 is connected to the linker L;

Ar is aryl or heteroaryl, and is optionally substituted with one or more independent $R^6$ groups;

$R^1$, $R^3$, $R^4$, $R^5$, and $R^6$ are each independently H, halo, —CN, —CF$_3$, —NO$_2$, —NH$_2$, —OH, —OCF$_3$, —OCH$_3$, —CO$_2$H, alkyl, alkenyl, alkynyl, cycloalkyl, heterocycloalkyl, arylalkyl, or heteroarylalkyl, each of which is optionally substituted with one or more independent $Q^2$ groups;

$Q^1$ and $Q^2$ are each independently H, halo, —CN, —CF$_3$, —OCF$_3$, —NO$_2$, oxo, alkyl, alkenyl, alkynyl, cycloalkyl, heterocycloalkyl, aryl, heteroaryl, heterocycloaryl, —OR$^7$, —S(O)$_n$R$^8$, —NR$^9$R$^{10}$, —SO$_2$NR$^9$R$^{10}$, —C(O)R$^{11}$, —C(O)NR$^9$R$^{10}$, —C(O)OR$^{12}$, —OC(O)R$^{13}$, —NR$^9$C(O)R$^{11}$, —NR$^9$S(O)$_2$R$^{14}$, —NR$^{15}$C(O)NR$^9$R$^{10}$, —NR$^{15}$S(O)$_2$NR$^9$R$^{10}$ or —NR$^{15}$S(O)NR$^9$R$^{10}$, each of which is optionally substituted with one or more independent H, halo, —CN, —OH, —NH$_2$, —NO$_2$, oxo, —CF$_3$, —OCF$_3$, —CO$_2$H, —S(O)—H, alkyl, aryl, heteroaryl, cycloalkyl, heterocycloalkyl, heterocycloaryl, or —O-alkyl, each of which may be partially or fully halogenated;

R$^7$, R$^8$, R$^{11}$, R$^{12}$, R$^{13}$, R$^{14}$, or R$^{15}$ are each independently H, alkyl, alkenyl, alkynyl, cycloalkyl, heterocycloalkyl, aryl, heteroaryl, or heterocycloaryl;

R$^9$ and R$^{10}$ are each independently H, alkyl, alkenyl, alkynyl, cycloalkyl, heterocycloalkyl, aryl, heteroaryl, or heterocycloaryl; or when in —NR$^9$R$^{10}$, R$^9$ and R$^{10}$, together with the nitrogen atom to which they are attached, form a 3- to 12-membered saturated or unsaturated ring, wherein said ring optionally includes one or more heteroatoms each independently being O, N, or S(O)$_n$; and n is 0, 1, or 2.

In some embodiments, X, Y, Z, V, and U are each independently C—R$^1$, thus giving the compound of Formula Ia or IIa, in which the R$^1$ groups can be the same or different.

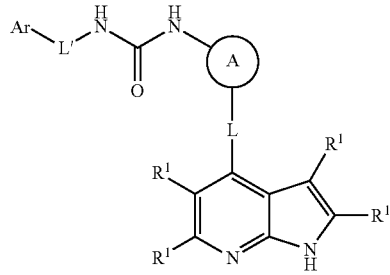

Ia

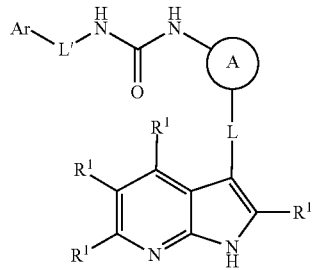

IIa

In some embodiments, each R$^1$ is H, and L' is a covalent bond.

In some embodiments, Y is N, and X, Z, V, and U are each independently C—R$^1$, thus giving the compound of Formula Ib or IIb, in which the R$^1$ groups can be the same or different.

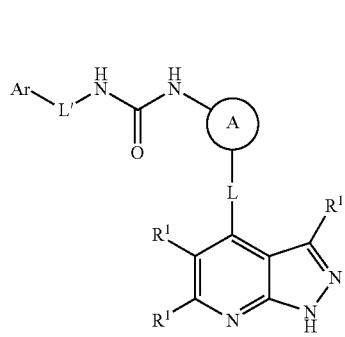

Ib

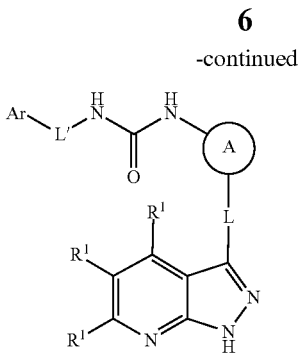

IIb

In some embodiments, each R$^1$ is H and L' is a covalent bond.

In some embodiments, Z is N; and X, Y, V, and U are each independently C—R$^1$, thus giving the compound of Formula Ic or IIc, in which the R$^1$ groups can be the same or different.

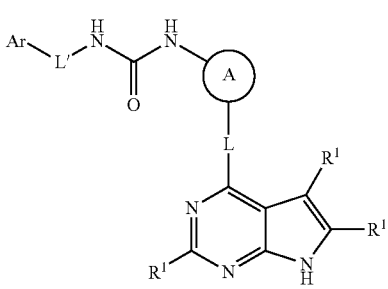

Ic

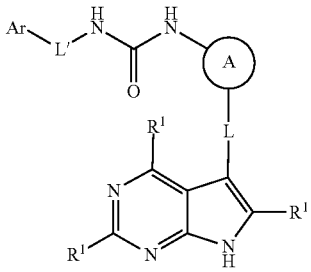

IIc

In some embodiments, each R$^1$ is H and L' is a covalent bond.

In some embodiments, the compound is of Formula I; X is N; and Y, Z, and V are each independently C—R$^1$, thus giving the compound of Formula Id, in which the R$^1$ groups can be the same or different.

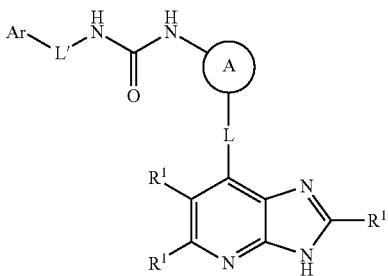

Id

In some embodiments, each R¹ is H and L' is a covalent bond.

In some embodiments, the compound is of Formula I; X and Z are each N; and Y and V are each independently C—R¹, thus giving the compound of Formula Ie in which the R¹ groups can be the same or different.

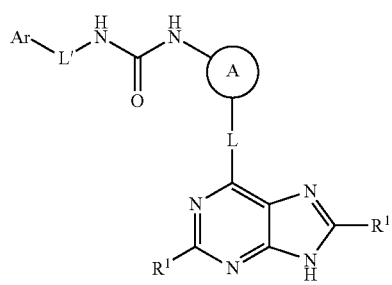

Ie

In some embodiments, each R¹ is H and L' is a covalent bond.

In some embodiments, L is alkylene optionally substituted with one or more independent R³ groups.

In some embodiments, L is alkylene (e.g., methylene, ethylene, propylene, or i-propylene).

In some embodiments, L' is a covalent bond.

In some embodiments, Ar is phenyl or indolinyl, and is optionally substituted with one or more groups each independent being halo, alkoxy, alkyl, haloalkoxy, cyano, oxo, or optionally substituted heterocycloalkyl.

In some embodiments, A is A1-a, A1-b, A1-c, A1-d, A1-e, A1-f, A1-g, A1-h, A1-i, A2-a, A2-b, A3-a, A3-b, A3-c, A3-d, or A3-e (as shown below), and is optionally substituted with one or more independent R⁵ groups.

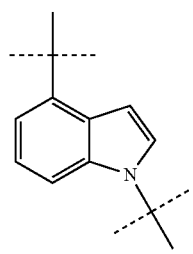

A1-a

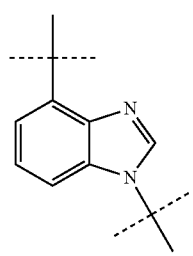

A1-b

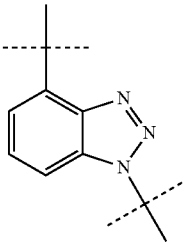

A1-c

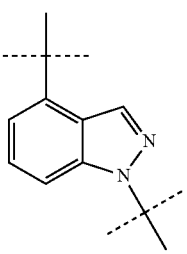

A1-d

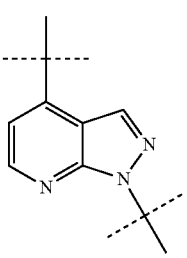

A1-e

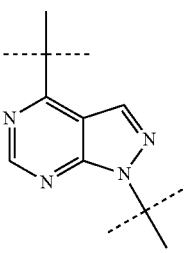

A1-f

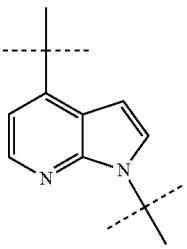

A1-g

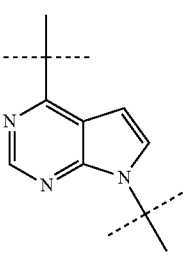

A1h

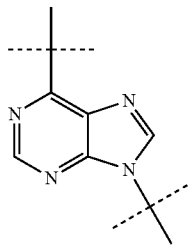
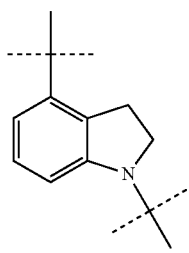
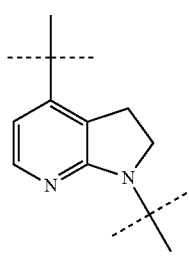
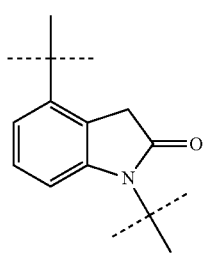
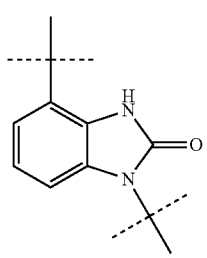
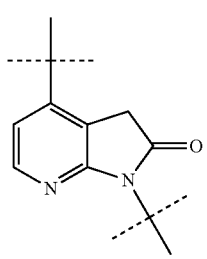

A1-i

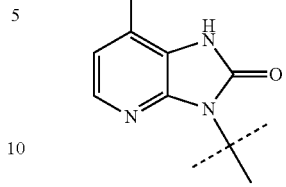

A2-a

A2-b

A3-a

A3-b

A3-c

A3-d

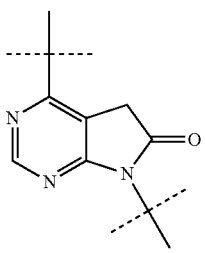

A3-e

In some embodiments, A is A1-a, A1-b, A1-d, A1-e, A1-g, A2-a, A2-b, A3-a, or A3-c, and is optionally substituted with one or more independent $R^5$ groups.

In some embodiments, A is A1-a, A1-b, A1-d, A1-g, A2-a, or A2-b, and is optionally substituted with one or more independent $R^5$ groups.

In some embodiments, A is A1-a or A2-a, and is optionally substituted with one or more independent $R^5$ groups.

In some embodiments, A is A1-a or A2-a without optional substituent.

In some embodiments, the compound is of the structure:

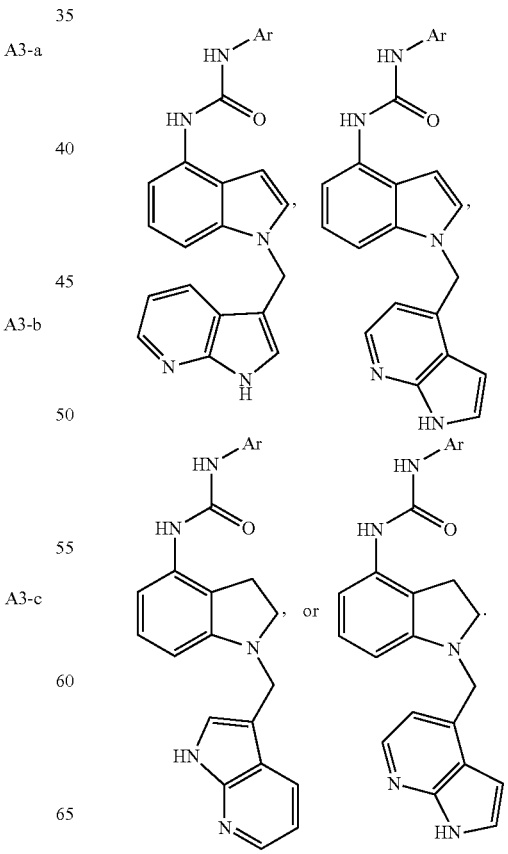

In some embodiments, Ar is phenyl, naphthyl, pyridinyl, pyridonyl, pyrimidinyl, pyridazinyl, triazinyl, imidazolyl, thiophenyl, furyl, thiazolyl, oxazolyl, triazolyl, quinolinyl, isoquinolinyl, tetrahydroquinolinyl, indolyl, azaindolyl, indazolyl, benzimidazolyl, benzofuryl, benzothiophenyl, benzotriazolyl, 2-oxindolyl, or indolinyl, each of which is optionally substituted with one or more groups each independent being halo, alkoxy, alkyl, haloalkoxy, cyano, oxo, or optionally substituted heterocycloalkyl.

In some embodiments, the compound is

1-Phenyl-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Fluorophenyl)-3-[1-(1H-pyrrolo[2,3-b]pyridin-3-ylmethyl)-1H-indol-4-yl]urea;
1-(4-Fluorophenyl)-3-[1-(1H-pyrrolo[2,3-b]pyridin-3-ylmethyl)-1H-indol-4-yl]urea;
1-(2-Chlorophenyl)-3-[1-(1H-pyrrolo[2,3-b]pyridin-3-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Chlorophenyl)-3-[1-(1H-pyrrolo[2,3-b]pyridin-3-ylmethyl)-1H-indol-4-yl]urea;
1-(2-Bromophenyl)-3-[1-(1H-pyrrolo[2,3-b]pyridin-3-ylmethyl)-1H-indol-4-yl]urea;
1-(3-Bromophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(2-Methylphenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(4-Methylphenyl)-3-[1-(1H-pyrrolo[2,3-b]pyridin-3-ylmethyl)-1H-indol-4-yl]urea;
1-(2-Methoxyphenyl)-3-[1-(1H-pyrrolo[2,3-b]pyridin-3-ylmethyl)-1H-indol-4-yl]urea;
1-(3-Methoxyphenyl)-3-[1-(1H-pyrrolo[2,3-b]pyridin-3-ylmethyl)-1H-indol-4-yl]urea;
1-(4-Methoxyphenyl)-3-[1-(1H-pyrrolo[2,3-b]pyridin-3-ylmethyl)-1H-indol-4-yl]urea;
1-(2-Trifluoromethoxyphenyl)-3-[1-(1H-pyrrolo[2,3-b]pyridin-3-ylmethyl)-1H-indol-4-yl]urea;
1-(3-Trifluoromethoxyphenyl)-3-[1-(1H-pyrrolo[2,3-b]pyridin-3-ylmethyl)-1H-indol-4-yl]urea;
1-(4-Trifluoromethoxyphenyl)-3-[1-(1H-pyrrolo[2,3-b]pyridin-3-ylmethyl)-1H-indol-4-yl]urea;
1-(2-Trifluoromethylphenyl)-3-[1-(1H-pyrrolo[2,3-b]pyridin-3-ylmethyl)-1H-indol-4-yl]urea;
1-(3-Trifluoromethylphenyl)-3-[1-(1H-pyrrolo[2,3-b]pyridin-3-ylmethyl)-1H-indol-4-yl]urea;
1-(4-Trifluoromethylphenyl)-3-[1-(1H-pyrrolo[2,3-b]pyridin-3-ylmethyl)-1H-indol-4-yl]urea;
1-(2-Cyanophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(4-Cyanophenyl)-3-[1-(1H-pyrrolo[2,3-b]pyridin-3-ylmethyl)-1H-indol-4-yl]urea;
1-(2-Methoxyl-5-fluorophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea;
1-(2-Methoxyl-5-bromophenyl)-3-[1-(1H-pyrrolo[2,3-b]pyridin-3-ylmethyl)-1H-indol-4-yl]urea;
1-(2-Methoxyl-5-methylphenyl)-3-[1-(1H-pyrrolo[2,3-b]pyridin-3-ylmethyl)-1H-indol-4-yl]urea;
1-(2,5-Dimethoxyphenyl)-3-[1-(1H-pyrrolo[2,3-b]pyridin-3-ylmethyl)-1H-indol-4-yl]urea;
1-(2-Methoxyl-5-trifluomethylphenyl)-3-[1-(1H-pyrrolo[2,3-b]pyridin-3-ylmethyl)-1H-indol-4-yl]urea;
1-(2-Fluoro-5-methylphenyl)-3-[1-(1H-pyrrolo[2,3-b]pyridin-3-ylmethyl)-1H-indol-4-yl]urea;
1-(2-Fluoro-5-methoxyphenyl)-3-[1-(1H-pyrrolo[2,3-b]pyridin-3-ylmethyl)-1H-indol-4-yl]urea;
1-(2-Fluoro-5-trifluoromethylphenyl)-3-[1-(1H-pyrrolo[2,3-b]pyridin-3-ylmethyl)-1H-indol-4-yl]urea;
1-(2-Fluoro-5-chlorophenyl)-3-[1-(1H-pyrrolo[2,3-b]pyridin-3-ylmethyl)-1H-indol-4-yl]urea;
1-(2-Fluoro-5-bromophenyl)-3-[1-(1H-pyrrolo[2,3-b]pyridin-3-ylmethyl)-1H-indol-4-yl]urea;
1-(2-Trifluoromethyl-5-methylphenyl)-3-[1-(1H-pyrrolo[2,3-b]pyridin-3-ylmethyl)-1H-indol-4-yl]urea;
1-(2-oxo-2,3-dihydro-1H-indol-5-yl)-3-[1-(1H-pyrrolo[2,3-b]pyridin-3-ylmethyl)-1H-indol-4-yl]urea;
1-[4-(5-oxopyrrolidin-2-yl)phenyl]-3-[1-(1H-pyrrolo[2,3-b]pyridin-3-ylmethyl)-1H-indol-4-yl]urea;
1-Phenyl-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(4-Chlorophenyl)-3-[1-(1H-pyrrolo[2,3-b]pyridin-4-ylmethyl)-1H-indol-4-yl]urea;
1-(2-Bromophenyl)-3-[1-(1H-pyrrolo[2,3-b]pyridin-4-ylmethyl)-1H-indol-4-yl]urea;
1-(3-Bromophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-4-ylmethyl)-1H-indol-4-yl]urea;
1-(2-Methylphenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(4-Methylphenyl)-3-[1-(1H-pyrrolo[2,3-b]pyridin-4-ylmethyl)-1H-indol-4-yl]urea;
1-(2-Methoxyphenyl)-3-[1-(1H-pyrrolo[2,3-b]pyridin-4-ylmethyl)-1H-indol-4-yl]urea;
1-(3-Methoxyphenyl)-3-[1-(1H-pyrrolo[2,3-b]pyridin-4-ylmethyl)-1H-indol-4-yl]urea;
1-(4-Methoxyphenyl)-3-[1-(1H-pyrrolo[2,3-b]pyridin-4-ylmethyl)-1H-indol-4-yl]urea;
1-(2-Trifluoromethoxyphenyl)-3-[1-(1H-pyrrolo[2,3-b]pyridin-4-ylmethyl)-1H-indol-4-yl]urea;
1-(3-Trifluoromethoxyphenyl)-3-[1-(1H-pyrrolo[2,3-b]pyridin-4-ylmethyl)-1H-indol-4-yl]urea;
1-(4-Trifluoromethoxyphenyl)-3-[1-(1H-pyrrolo[2,3-b]pyridin-4-ylmethyl)-1H-indol-4-yl]urea;
1-(2-Trifluoromethylphenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;

1-(2-Cyanophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(4-Cyanophenyl)-3-[1-(1H-pyrrolo[2,3-b]pyridin-4-ylmethyl)-1H-indol-4-yl]urea;
1-(2-Methoxyl-5-fluorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(2-Methoxyl-5-bromophenyl)-3-[1-(1H-pyrrolo[2,3-b]pyridin-4-ylmethyl)-1H-indol-4-yl]urea;
1-(2-Methoxyl-5-methylphenyl)-3-[1-(1H-pyrrolo[2,3-b]pyridin-4-ylmethyl)-1H-indol-4-yl]urea;
1-(2,5-Dimethoxyphenyl)-3-[1-(1H-pyrrolo[2,3-b]pyridin-4-ylmethyl)-1H-indol-4-yl]urea;
1-(2-Methoxyl-5-trifluomethylphenyl)-3-[1-(1H-pyrrolo[2,3-b]pyridin-4-ylmethyl)-1H-indol-4-yl]urea;
1-(2-Fluoro-5-methylphenyl)-3-[1-(1H-pyrrolo[2,3-b]pyridin-4-ylmethyl)-1H-indol-4-yl]urea;
1-(2-Fluoro-5-methoxyphenyl)-3-[1-(1H-pyrrolo[2,3-b]pyridin-4-ylmethyl)-1H-indol-4-yl]urea;
1-(2-Fluoro-5-trifluoromethylphenyl)-3-[1-(1H-pyrrolo[2,3-b]pyridin-4-ylmethyl)-1H-indol-4-yl]urea
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Trifluoromethyl-5-methylphenyl)-3-[1-(1H-pyrrolo[2,3-b]pyridin-4-ylmethyl)-1H-indol-4-yl]urea;
1-(2-oxo-2,3-dihydro-1H-indol-5-yl)-3-[1-(1H-pyrrolo[2,3-b]pyridin-4-ylmethyl)-1H-indol-4-yl]urea;
1-[4-(5-oxopyrrolidin-2-yl)phenyl]-3-[1-(1H-pyrrolo[2,3-b]pyridin-4-ylmethyl)-1H-indol-4-yl]urea;
1-Phenyl-3-[1-(1H-pyrrolo[2,3-b]pyridin-3-ylmethyl)-2,3-dihydro-1H-indol-4-yl]urea;
1-(2-Fluorophenyl)-3-[1-(1H-pyrrolo[2,3-b]pyridin-3-ylmethyl)-2,3-dihydro-1H-indol-4-yl]urea;
1-(3-Fluorophenyl)-3-[1-(1H-pyrrolo[2,3-b]pyridin-3-ylmethyl)-2,3-dihydro-1H-indol-4-yl]urea;
1-(4-Fluorophenyl)-3-[1-(1H-pyrrolo[2,3-b]pyridin-3-ylmethyl)-2,3-dihydro-1H-indol-4-yl]urea;
1-(2-Chlorophenyl)-3-[1-(1H-pyrrolo[2,3-b]pyridin-3-ylmethyl)-2,3-dihydro-1H-indol-4-yl]urea;
1-(3-Chlorophenyl)-3-[1-(1H-pyrrolo[2,3-b]pyridin-3-ylmethyl)-2,3-dihydro-1H-indol-4-yl]urea;
1-(4-Chlorophenyl)-3-[1-(1H-pyrrolo[2,3-b]pyridin-3-ylmethyl)-2,3-dihydro-1H-indol-4-yl]urea;
1-(2-Bromophenyl)-3-[1-(1H-pyrrolo[2,3-b]pyridin-3-ylmethyl)-2,3-dihydro-1H-indol-4-yl]urea;
1-(3-Bromophenyl)-3-[1-(1H-pyrrolo[2,3-b]pyridin-3-ylmethyl)-2,3-dihydro-1H-indol-4-yl]urea;
1-(4-Bromophenyl)-3-[1-(1H-pyrrolo[2,3-b]pyridin-3-ylmethyl)-2,3-dihydro-1H-indol-4-yl]urea;
1-(2-Methylphenyl)-3-[1-(1H-pyrrolo[2,3-b]pyridin-3-ylmethyl)-2,3-dihydro-1H-indol-4-yl]urea;
1-(3-Methylphenyl)-3-[1-(1H-pyrrolo[2,3-b]pyridin-3-ylmethyl)-2,3-dihydro-1H-indol-4-yl]urea;
1-(4-Methylphenyl)-3-[1-(1H-pyrrolo[2,3-b]pyridin-3-ylmethyl)-2,3-dihydro-1H-indol-4-yl]urea;
1-(2-Methoxyphenyl)-3-[1-(1H-pyrrolo[2,3-b]pyridin-3-ylmethyl)-2,3-dihydro-1H-indol-4-yl]urea;
1-(3-Methoxyphenyl)-3-[1-(1H-pyrrolo[2,3-b]pyridin-3-ylmethyl)-2,3-dihydro-1H-indol-4-yl]urea;
1-(4-Methoxyphenyl)-3-[1-(1H-pyrrolo[2,3-b]pyridin-3-ylmethyl)-2,3-dihydro-1H-indol-4-yl]urea;
1-(2-Trifluoromethoxyphenyl)-3-[1-(1H-pyrrolo[2,3-b]pyridin-3-ylmethyl)-2,3-dihydro-1H-indol-4-yl]urea;
1-(3-Trifluoromethoxyphenyl)-3-[1-(1H-pyrrolo[2,3-b]pyridin-3-ylmethyl)-2,3-dihydro-1H-indol-4-yl]urea;
1-(4-Trifluoromethoxyphenyl)-3-[1-(1H-pyrrolo[2,3-b]pyridin-3-ylmethyl)-2,3-dihydro-1H-indol-4-yl]urea;
1-(2-Trifluoromethylphenyl)-3-[1-(1H-pyrrolo[2,3-b]pyridin-3-ylmethyl)-2,3-dihydro-1H-indol-4-yl]urea;
1-(3-Trifluoromethylphenyl)-3-[1-(1H-pyrrolo[2,3-b]pyridin-3-ylmethyl)-2,3-dihydro-1H-indol-4-yl]urea;
1-(4-Trifluoromethylphenyl)-3-[1-(1H-pyrrolo[2,3-b]pyridin-3-ylmethyl)-2,3-dihydro-1H-indol-4-yl]urea;
1-(2-Cyanophenyl)-3-[1-(1H-pyrrolo[2,3-b]pyridin-3-ylmethyl)-2,3-dihydro-1H-indol-4-yl]urea;
1-(3-Cyanophenyl)-3-[1-(1H-pyrrolo[2,3-b]pyridin-3-ylmethyl)-2,3-dihydro-1H-indol-4-yl]urea;
1-(4-Cyanophenyl)-3-[1-(1H-pyrrolo[2,3-b]pyridin-3-ylmethyl)-2,3-dihydro-1H-indol-4-yl]urea;
1-(2-Methoxyl-5-fluorophenyl)-3-[1-(1H-pyrrolo[2,3-b]pyridin-3-ylmethyl)-2,3-dihydro-1H-indol-4-yl]urea;
1-(2-Methoxyl-5-chlorophenyl)-3-[1-(1H-pyrrolo[2,3-b]pyridin-3-ylmethyl)-2,3-dihydro-1H-indol-4-yl]urea;
1-(2-Methoxyl-5-bromophenyl)-3-[1-(1H-pyrrolo[2,3-b]pyridin-3-ylmethyl)-2,3-dihydro-1H-indol-4-yl]urea;
1-(2-Methoxyl-5-methylphenyl)-3-[1-(1H-pyrrolo[2,3-b]pyridin-3-ylmethyl)-2,3-dihydro-1H-indol-4-yl]urea;
1-(2,5-Dimethoxyphenyl)-3-[1-(1H-pyrrolo[2,3-b]pyridin-3-ylmethyl)-2,3-dihydro-1H-indol-4-yl]urea;
1-(2-Methoxyl-5-trifluomethylphenyl)-3-[1-(1H-pyrrolo[2,3-b]pyridin-3-ylmethyl)-2,3-dihydro-1H-indol-4-yl]urea;
1-(2-Fluoro-5-methylphenyl)-3-[1-(1H-pyrrolo[2,3-b]pyridin-3-ylmethyl)-2,3-dihydro-1H-indol-4-yl]urea;
1-(2-Fluoro-5-methoxyphenyl)-3-[1-(1H-pyrrolo[2,3-b]pyridin-3-ylmethyl)-2,3-dihydro-1H-indol-4-yl]urea;
1-(2-Fluoro-5-trifluoromethylphenyl)-3-[1-(1H-pyrrolo[2,3-b]pyridin-3-ylmethyl)-2,3-dihydro-1H-indol-4-yl]urea;
1-(2-Fluoro-5-chlorophenyl)-3-[1-(1H-pyrrolo[2,3-b]pyridin-3-ylmethyl)-2,3-dihydro-1H-indol-4-yl]urea;
1-(2-Fluoro-5-bromophenyl)-3-[1-(1H-pyrrolo[2,3-b]pyridin-3-ylmethyl)-2,3-dihydro-1H-indol-4-yl]urea;
1-(2-Trifluoromethyl-5-methylphenyl)-3-[1-(1H-pyrrolo[2,3-b]pyridin-3-ylmethyl)-2,3-dihydro-1H-indol-4-yl]urea;
1-(2-oxo-2,3-dihydro-1H-indol-5-yl)-3-[1-(1H-pyrrolo[2,3-b]pyridin-3-ylmethyl)-2,3-dihydro-1H-indol-4-yl]urea;
1-[4-(5-oxopyrrolidin-2-yl)phenyl]-3-[1-(1H-pyrrolo[2,3-b]pyridin-3-ylmethyl)-2,3-dihydro-1H-indol-4-yl]urea;
1-Phenyl-3-[1-(1H-pyrrolo[2,3-b]pyridin-4-ylmethyl)-2,3-dihydro-1H-indol-4-yl]urea;
1-(2-Fluorophenyl)-3-[1-(1H-pyrrolo[2,3-b]pyridin-4-ylmethyl)-2,3-dihydro-1H-indol-4-yl]urea;
1-(3-Fluorophenyl)-3-[1-(1H-pyrrolo[2,3-b]pyridin-4-ylmethyl)-2,3-dihydro-1H-indol-4-yl]urea;
1-(4-Fluorophenyl)-3-[1-(1H-pyrrolo[2,3-b]pyridin-4-ylmethyl)-2,3-dihydro-1H-indol-4-yl]urea;
1-(2-Chlorophenyl)-3-[1-(1H-pyrrolo[2,3-b]pyridin-4-ylmethyl)-2,3-dihydro-1H-indol-4-yl]urea;
1-(3-Chlorophenyl)-3-[1-(1H-pyrrolo[2,3-b]pyridin-4-ylmethyl)-2,3-dihydro-1H-indol-4-yl]urea;
1-(4-Chlorophenyl)-3-[1-(1H-pyrrolo[2,3-b]pyridin-4-ylmethyl)-2,3-dihydro-1H-indol-4-yl]urea;
1-(2-Bromophenyl)-3-[1-(1H-pyrrolo[2,3-b]pyridin-4-ylmethyl)-2,3-dihydro-1H-indol-4-yl]urea;
1-(3-Bromophenyl)-3-[1-(1H-pyrrolo[2,3-b]pyridin-4-ylmethyl)-2,3-dihydro-1H-indol-4-yl]urea;
1-(4-Bromophenyl)-3-[1-(1H-pyrrolo[2,3-b]pyridin-4-ylmethyl)-2,3-dihydro-1H-indol-4-yl]urea;

1-(2-Methylphenyl)-3-[1-(1H-pyrrolo[2,3-b]pyridin-4-ylmethyl)-2,3-dihydro-1H-indol-4-yl]urea;
1-(3-Methylphenyl)-3-[1-(1H-pyrrolo[2,3-b]pyridin-4-ylmethyl)-2,3-dihydro-1H-indol-4-yl]urea;
1-(4-Methylphenyl)-3-[1-(1H-pyrrolo[2,3-b]pyridin-4-ylmethyl)-2,3-dihydro-1H-indol-4-yl]urea;
1-(2-Methoxyphenyl)-3-[1-(1H-pyrrolo[2,3-b]pyridin-4-ylmethyl)-2,3-dihydro-1H-indol-4-yl]urea;
1-(3-Methoxyphenyl)-3-[1-(1H-pyrrolo[2,3-b]pyridin-4-ylmethyl)-2,3-dihydro-1H-indol-4-yl]urea;
1-(4-Methoxyphenyl)-3-[1-(1H-pyrrolo[2,3-b]pyridin-4-ylmethyl)-2,3-dihydro-1H-indol-4-yl]urea;
1-(2-Trifluoromethoxyphenyl)-3-[1-(1H-pyrrolo[2,3-b]pyridin-4-ylmethyl)-2,3-dihydro-1H-indol-4-yl]urea;
1-(3-Trifluoromethoxyphenyl)-3-[1-(1H-pyrrolo[2,3-b]pyridin-4-ylmethyl)-2,3-dihydro-1H-indol-4-yl]urea;
1-(4-Trifluoromethoxyphenyl)-3-[1-(1H-pyrrolo[2,3-b]pyridin-4-ylmethyl)-2,3-dihydro-1H-indol-4-yl]urea;
1-(2-Trifluoromethylphenyl)-3-[1-(1H-pyrrolo[2,3-b]pyridin-4-ylmethyl)-2,3-dihydro-1H-indol-4-yl]urea;
1-(3-Trifluoromethylphenyl)-3-[1-(1H-pyrrolo[2,3-b]pyridin-4-ylmethyl)-2,3-dihydro-1H-indol-4-yl]urea;
1-(4-Trifluoromethylphenyl)-3-[1-(1H-pyrrolo[2,3-b]pyridin-4-ylmethyl)-2,3-dihydro-1H-indol-4-yl]urea;
1-(2-Cyanophenyl)-3-[1-(1H-pyrrolo[2,3-b]pyridin-4-ylmethyl)-2,3-dihydro-1H-indol-4-yl]urea;
1-(3-Cyanophenyl)-3-[1-(1H-pyrrolo[2,3-b]pyridin-4-ylmethyl)-2,3-dihydro-1H-indol-4-yl]urea;
1-(4-Cyanophenyl)-3-[1-(1H-pyrrolo[2,3-b]pyridin-4-ylmethyl)-2,3-dihydro-1H-indol-4-yl]urea;
1-(2-Methoxyl-5-fluorophenyl)-3-[1-(1H-pyrrolo[2,3-b]pyridin-4-ylmethyl)-2,3-dihydro-1H-indol-4-yl]urea;
1-(2-Methoxyl-5-chlorophenyl)-3-[1-(1H-pyrrolo[2,3-b]pyridin-4-ylmethyl)-2,3-dihydro-1H-indol-4-yl]urea;
1-(2-Methoxyl-5-bromophenyl)-3-[1-(1H-pyrrolo[2,3-b]pyridin-4-ylmethyl)-2,3-dihydro-1H-indol-4-yl]urea;
1-(2-Methoxyl-5-methylphenyl)-3-[1-(1H-pyrrolo[2,3-b]pyridin-4-ylmethyl)-2,3-dihydro-1H-indol-4-yl]urea;
1-(2,5-Dimethoxyphenyl)-3-[1-(1H-pyrrolo[2,3-b]pyridin-4-ylmethyl)-2,3-dihydro-1H-indol-4-yl]urea;
1-(2-Methoxyl-5-trifluomethylphenyl)-3-[1-(1H-pyrrolo[2,3-b]pyridin-4-ylmethyl)-2,3-dihydro-1H-indol-4-yl]urea;
1-(2-Fluoro-5-methylphenyl)-3-[1-(1H-pyrrolo[2,3-b]pyridin-4-ylmethyl)-2,3-dihydro-1H-indol-4-yl]urea;
1-(2-Fluoro-5-methoxyphenyl)-3-[1-(1H-pyrrolo[2,3-b]pyridin-4-ylmethyl)-2,3-dihydro-1H-indol-4-yl]urea;
1-(2-Fluoro-5-trifluoromethylphenyl)-3-[1-(1H-pyrrolo[2,3-b]pyridin-4-ylmethyl)-2,3-dihydro-1H-indol-4-yl]urea;
1-(2-Fluoro-5-chlorophenyl)-3-[1-(1H-pyrrolo[2,3-b]pyridin-4-ylmethyl)-2,3-dihydro-1H-indol-4-yl]urea;
1-(2-Fluoro-5-bromophenyl)-3-[1-(1H-pyrrolo[2,3-b]pyridin-4-ylmethyl)-2,3-dihydro-1H-indol-4-yl]urea;
1-(2-Trifluoromethyl-5-methylphenyl)-3-[1-(1H-pyrrolo[2,3-b]pyridin-4-ylmethyl)-2,3-dihydro-1H-indol-4-yl]urea;
1-(2-oxo-2,3-dihydro-1H-indol-5-yl)-3-[1-(1H-pyrrolo[2,3-b]pyridin-4-ylmethyl)-2,3-dihydro-1H-indol-4-yl]urea;
1-[4-(5-oxopyrrolidin-2-yl)phenyl]-3-[1-(1H-pyrrolo[2,3-b]pyridin-4-ylmethyl)-2,3-dihydro-1H-indol-4-yl]urea;
1-(2-chloro-5-methylphenyl)-3-[1-(1H-pyrrolo[2,3-b]pyridin-3-ylmethyl)-1H-indol-4-yl]urea;
1-(2-bromo-5-methylphenyl)-3-[1-(1H-pyrrolo[2,3-b]pyridin-3-ylmethyl)-1H-indol-4-yl]urea;
1-(2-fluoro-4-chlorophenyl)-3-[1-(1H-pyrrolo[2,3-b]pyridin-3-ylmethyl)-1H-indol-4-yl]urea;
1-(2-fluoro-6-chlorophenyl)-3-[1-(1H-pyrrolo[2,3-b]pyridin-3-ylmethyl)-1H-indol-4-yl]urea;
1-(4-morpholinomethylphenyl)-3-[1-(1H-pyrrolo[2,3-b]pyridin-3-ylmethyl)-1H-indol-4-yl]urea;
1-(2-Methyl-3-fluorophenyl)-3-[1-(1H-pyrrolo[2,3-b]pyridin-3-ylmethyl)-1H-indol-4-yl]urea;
1-(2-Methyl-3-chlorophenyl)-3-[1-(1H-pyrrolo[2,3-b]pyridin-3-ylmethyl)-1H-indol-4-yl]urea;
1-(2-Methyl-3-bromophenyl)-3-[1-(1H-pyrrolo[2,3-b]pyridin-3-ylmethyl)-1H-indol-4-yl]urea;
1-(2-chloro-5-methylphenyl)-3-[1-(1H-pyrrolo[2,3-b]pyridin-4-ylmethyl)-1H-indol-4-yl]urea;
1-(2-bromo-5-methylphenyl)-3-[1-(1H-pyrrolo[2,3-b]pyridin-4-ylmethyl)-1H-indol-4-yl]urea;
1-(2-fluoro-6-chlorophenyl)-3-[1-(1H-pyrrolo[2,3-b]pyridin-4-ylmethyl)-1H-indol-4-yl]urea;
1-(4-morpholinomethylphenyl)-3-[1-(1H-pyrrolo[2,3-b]pyridin-4-ylmethyl)-1H-indol-4-yl]urea;
1-(2-Methyl-3-fluorophenyl)-3-[1-(1H-pyrrolo[2,3-b]pyridin-4-ylmethyl)-1H-indol-4-yl]urea;
1-(2-Methyl-3-chlorophenyl)-3-[1-(1H-pyrrolo[2,3-b]pyridin-4-ylmethyl)-1H-indol-4-yl]urea;
1-(2-Methyl-3-bromophenyl)-3-[1-(1H-pyrrolo[2,3-b]pyridin-4-ylmethyl)-1H-indol-4-yl]urea;
1-(2-Methoxy-5-chlorophenyl)-3-[1-(1H-pyrrolo[2,3-b]pyridin-4-ylmethyl)-2,3-dihydro-1H-indol-4-yl]urea.

In some other embodiments, the compound is:
1-Phenyl-3-[1-(1H-pyrrolo[2,3-b]pyridin-3-ylmethyl)-1H-indol-4-yl]urea;
1-(2-Chlorophenyl)-3-[1-(1H-pyrrolo[2,3-b]pyridin-3-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Chlorophenyl)-3-[1-(1H-pyrrolo[2,3-b]pyridin-3-ylmethyl)-1H-indol-4-yl]urea;
1-(2-Bromophenyl)-3-[1-(1H-pyrrolo[2,3-b]pyridin-3-ylmethyl)-1H-indol-4-yl]urea;
1-(3-Bromophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(2-Methoxyphenyl)-3-[1-(1H-pyrrolo[2,3-b]pyridin-3-ylmethyl)-1H-indol-4-yl]urea;
1-(3-Methoxyphenyl)-3-[1-(1H-pyrrolo[2,3-b]pyridin-3-ylmethyl)-1H-indol-4-yl]urea;
1-(4-Methoxyphenyl)-3-[1-(1H-pyrrolo[2,3-b]pyridin-3-ylmethyl)-1H-indol-4-yl]urea;
1-(2-Methylphenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(4-Methylphenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Fluorophenyl)-3-[1-(1H-pyrrolo[2,3-b]pyridin-3-ylmethyl)-1H-indol-4-yl]urea;
1-(4-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(4-Cyanophenyl)-3-[1-(1H-pyrrolo[2,3-b]pyridin-3-ylmethyl)-1H-indol-4-yl]urea;
1-(2-Trifluoromethylphenyl)-3-[1-(1H-pyrrolo[2,3-b]pyridin-3-ylmethyl)-1H-indol-4-yl]urea;
1-(3-Trifluoromethylphenyl)-3-[1-(1H-pyrrolo[2,3-b]pyridin-3-ylmethyl)-1H-indol-4-yl]urea;
1-(4-Trifluoromethylphenyl)-3-[1-(1H-pyrrolo[2,3-b]pyridin-3-ylmethyl)-1H-indol-4-yl]urea;

1-(2-Trifluoromethoxyphenyl)-3-[1-(1H-pyrrolo[2,3-b]pyridin-3-ylmethyl)-1H-indol-4-yl]urea;
1-(3-Trifluoromethoxyphenyl)-3-[1-(1H-pyrrolo[2,3-b]pyridin-3-ylmethyl)-1H-indol-4-yl]urea;
1-(4-Trifluoromethoxyphenyl)-3-[1-(1H-pyrrolo[2,3-b]pyridin-3-ylmethyl)-1H-indol-4-yl]urea;
1-(2-Fluoro-5-chlorophenyl)-3-[1-(1H-pyrrolo[2,3-b]pyridin-3-ylmethyl)-1H-indol-4-yl]urea;
1-(2-Fluoro-5-bromophenyl)-3-[1-(1H-pyrrolo[2,3-b]pyridin-3-ylmethyl)-1H-indol-4-yl]urea;
1-(2-Fluoro-5-methoxyphenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea;
1-(2,5-Dimethoxyphenyl)-3-[1-(1H-pyrrolo[2,3-b]pyridin-3-ylmethyl)-1H-indol-4-yl]urea;
1-(2-fluoro-4-chlorophenyl)-3-[1-(1H-pyrrolo[2,3-b]pyridin-3-ylmethyl)-1H-indol-4-yl]urea;
1-Phenyl-3-[1-(1H-pyrrolo[2,3-b]pyridin-4-ylmethyl)-1H-indol-4-yl]urea;
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(4-Chlorophenyl)-3-[1-(1H-pyrrolo[2,3-b]pyridin-4-ylmethyl)-1H-indol-4-yl]urea;
1-(2-Bromophenyl)-3-[1-(1H-pyrrolo[2,3-b]pyridin-4-ylmethyl)-1H-indol-4-yl]urea;
1-(3-Bromophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-4-ylmethyl)-1H-indol-4-yl]urea;
1-(2-Methoxyphenyl)-3-[1-(1H-pyrrolo[2,3-b]pyridin-4-ylmethyl)-1H-indol-4-yl]urea;
1-(3-Methoxyphenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(4-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(4-Cyanophenyl)-3-[1-(1H-pyrrolo[2,3-b]pyridin-4-ylmethyl)-1H-indol-4-yl]urea;
1-(2-Trifluoromethylphenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(4-Trifluoromethoxyphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(2-bromo-5-methylphenyl)-3-[1-(1H-pyrrolo[2,3-b]pyridin-4-ylmethyl)-1H-indol-4-yl]urea;
1-(2-fluoro-4-chlorophenyl)-3-[1-(1H-pyrrolo[2,3-b]pyridin-4-ylmethyl)-1H-indol-4-yl]urea;
1-(2-Methyl-3-fluorophenyl)-3-[1-(1H-pyrrolo[2,3-b]pyridin-4-ylmethyl)-1H-indol-4-yl]urea;
1-(2-Trifluoromethoxyphenyl)-3-[1-(1H-pyrrolo[2,3-b]pyridin-4-ylmethyl)-1H-indol-4-yl]urea
1-(2-Methylphenyl)-3-[1-(1H-pyrrolo[2,3-b]pyridin-4-ylmethyl)-1H-indol-4-yl]urea; or
1-(2-Methoxy-5-chlorophenyl)-3-[1-(1H-pyrrolo[2,3-b]pyridin-4-ylmethyl)-2,3-dihydro-1H-indol-4-yl]urea.

In some other embodiments, the compound is:
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Fluoro-4-chlorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

In some other embodiments, the compound is
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;

1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Fluoro-4-chlorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b.]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

In some embodiments, the compound is:
1-(3-Cyanophenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2, 3-1).]pyridin-4-ylmethyl)-1H-indol-4-yl]urea;
1-(2-Fluoro-4-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

In some embodiments, the compound is:
1-(2-Fluoro-5-bromophenyl)-3-[1-(1H-pyrrolo[2,3-b]pyridin-4-ylmethyl)-1H-indol-4-yl]urea;
1-(2-fluoro-4-chlorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

In some embodiments, the compound is:
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea; or
1-(2-Fluoro-5-chlorophenyl)-3-[1-(1H-pyrrolo[2,3-b]pyridin-4-ylmethyl)-1H-indol-4-yl]urea.

In some embodiments, the compound is:
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea; or
1-(2-Methoxyl-5-chlorophenyl)-3-[1-(1H-pyrrolo[2,3-b]pyridin-3-ylmethyl)-1H-indol-4-yl]urea.

In some embodiments, the compound is:
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Fluoro-4-chlorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea; or
1-(4-Bromophenyl)-3-[1-(1H-pyrrolo[2,3-b]pyridin-3-ylmethyl)-1H-indol-4-yl]urea.

In some embodiments, the compound is:
1-(2-Chlorophenyl)-3-[1-(1H-pyrrolo[2,3-b]pyridin-4-ylmethyl)-1H-indol-4-yl]urea;

1-(3-Chlorophenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea; or
1-(4-Fluorophenyl)-3-[1-(1H-pyrrolo[2,3-b]pyridin-4-ylmethyl)-1H-indol-4-yl]urea.

In some embodiments, the compound is:
1-(3-Cyanophenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea; or
1-(2-Fluoro-4-chlorophenyl)-3-[1-(1H-pyrrolo[2,3-b]pyridin-4-ylmethyl)-1H-indol-4-yl]urea.

In some embodiments, the compound is:
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea;

In some embodiments, the compound is:
1-(3-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea; or
1-(2-Methoxyl-5-chlorophenyl)-3-[1-(1H-pyrrolo[2,3-b]pyridin-3-ylmethyl)-1H-indol-4-yl]urea;

In some embodiments, the compound is:
1-(3-Cyanophenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-4-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

Another aspect of the present invention provides pharmaceutical compositions each including a therapeutically effective amount of any of the compounds described above and a pharmaceutically acceptable carrier. The pharmaceutical compositions can be any form that is suitable for an intended administration method, e.g., injectable, aerosol, cream, gel, capsule, pill, tablet, syrup, eye drop, or ointment.

The compounds described above exhibit inhibitory effect on one or more protein kinases, e.g., c-Met, VEGFR2, PDGFRβ, c-Kit, CSF1R, and EphA2.

Accordingly, another aspect of the present invention provides a method for treating a patient having a condition mediated by an abnormal protein kinase activity (e.g., overexpressed protein kinase). The method includes administering to the patient in need thereof a therapeutically effective amount of any of the compounds or pharmaceutical compositions described above. The compound or pharmaceutical composition can be administered in a suitable manner, e.g., intravenously, subcutaneously, orally, parenterally, or topically. Examples of such a protein kinase include VEGFR2, c-Met, RON, PDGFRα, PDGFRβ, c-Kit, CSF1R, EphA2, Alk, Tie-1, Tie-2, Flt3, FGFR1, FGFR2, FGFR3, FGFR4, EGFR, Her2, Abl, Aurora A, Aurora B, Aurora C, Src, Lck, IGF-1R, and IR. Examples of such a condition include cancer, tumor, rheumatoid arthritis, autoimmune disease, acute inflammation, nephritis, diabetic retinitis, psoriasis, and macular degeneration. The tumor or cancer can be, e.g., bone cancer (e.g., Ewing's sarcoma, osteosarcoma, chondrosarcoma, or orthopaedics links), brain and CNS tumor (e.g., acoustic neuroma, spinal cord tumor, brain tumor ring of hope), breast cancer, breast cancer, colorectal cancer (e.g., anal cancer), endocrine cancer (e.g., adrenocortical carcinoma, pancreatic cancer (e.g. pancreatic carcinoma such as exocrine pancreatic carcinoma), pituitary cancer, thyroid cancer, parathyroid cancer, thymus cancer, multiple endocrine neoplasia, or other endocrine cancer), gastrointestinal cancer (e.g., stomach cancer, esophageal cancer, small intestine cancer, gall bladder cancer, liver cancer, extra-hepatic bile duct cancer, or gastrointestinal carcinoid tumor), genitourinary cancer (e.g., testicular cancer, penile cancer, or prostate cancer), gynecological cancer (e.g., cervical cancer, ovarian cancer, vaginal cancer, uterus/endometrium cancer, vulva cancer, gestational trophoblastic cancer, fallopian tube cancer, or uterine sarcoma), head and neck cancer (e.g., oral cavity, lip, salivary gland cancer, larynx, hypopharynx, oropharynx cancer, nasal, paranasal, or nasopharynx cancer), leukemia (e.g., acute lymphocytic leukemia, acute myeloid leukemia, chronic lymphocytic leukemia, chronic myeloid leukemia, hairy cell leukemia, acute promyelocytic leukemia, plasma cell leukemia), lung cancer (e.g., adenocarcinoma, small cell lung cancer, or non-small cell lung cancer), lymphoma (e.g., Hodgkin's Disease, Non-Hodgkin's Lymphoma, AIDS-related Lymphoma), eye cancer (e.g., retinoblastoma or intraocular melanoma), skin cancer (e.g., melanoma, non-melanoma skin cancer or Merkel cell cancer), soft tissue sarcoma (e.g., Kaposi's Sarcoma), urinary system cancer (e.g., kidney cancer, Wilm's tumor, bladder cancer, urethral cancer, or transitional cell cancer), and other types or related disorders (e.g., histiocytosis, mesothelioma, metastatic cancer, carcinoid tumors, neurofibromatosis, germ cell tumors, desmoplasic small round cell tumor, malignant rhabdoid tumor, desmoid tumor, ataxia-telangiectasia, Nijmegen breakage syndrome, Rothmund-Thomson syndrome, Li-Fraumeni Syndrome, von Hipple-Lindau Disease, Beckwith-Wiedemann syndrome, Down's syndrome, Denys-Drash syndrome, WAGR syndrome, or CIN cervical intraepithelial neoplasm).

Chemical entities of the present invention include, but are not limited to compounds of Formula I or II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, crystal forms, chelates, non-covalent complexes, prodrugs, and mixtures.

As noted above, prodrugs also fall within the scope of chemical entities, for example ester or amide derivatives of the compounds of Formula I or II. The term "prodrugs" includes any compounds that become compounds of Formula I or II when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I or II.

As used herein, the term "solvate" refers to the chemical entity formed by the interaction of a solvent and a compound. Suitable solvates are pharmaceutically acceptable solvates, such as hydrates, including monohydrates and hemi-hydrates.

As used herein, the term "chelate" refers to the chemical entity formed by the coordination of a compound to a metal ion at two (or more) points.

As used herein, the term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example, an active agent may be an anti-cancer therapeutic.

As used herein, the term "alkyl", used alone or as part of a larger moiety (e.g., as in "cycloalkenylalkyl" or "haloalkyloxy"), refers to a saturated aliphatic hydrocarbon group. It can contain 1 to 8 (e.g., 1 to 6 or 1 to 4) carbon atoms. As a moiety, it can be denoted as —$C_nH_{2n+1}$. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., optionally substituted) with one or more substituents.

As used herein, the term "alkylene", used alone or as part of a larger moiety (e.g., as in "arylalkyleneoxy" or "arylhaloalkylenoxy"), refers to a saturated aliphatic hydrocarbon group with two radical points for forming two covalent bonds with two other moieties. It can contain 1 to 8 (e.g., 1 to 6 or 1 to 4) carbon atoms. As a moiety, it can be denoted as —$C_nH_{2n}$—. Examples of an alkylene group include, but are not limited to, methylene (—$CH_2$—), ethylene (—$CH_2CH_2$—), and propylene (—$CH_2CH_2CH_2$—).

As used herein, the term "alkynyl", used alone or as part of a larger moiety (e.g., as in "alkynylalkyl" or "haloalkynylalkoxy"), refers to an aliphatic hydrocarbon group with at least one triple bond. It can contain 2 to 8 (e.g., 2 to 6 or 2 to 4) carbon atoms. An alkynyl group can be straight or branched. Examples of an alkynyl group include, but are not limited to, propargyl and butynyl.

As used herein, the term "alkenyl", used alone or as part of a larger moiety (e.g., as in "alkenylalkyl" or "alkenylalkoxy"), refers to an aliphatic hydrocarbon group with at least one double bond. It can contain 2 to 8 (e.g., 2 to 6 or 2 to 4) carbon atoms. An alkenyl group with one double bond can be denoted as —$C_nH_{2n-1}$, or —$C_nH_{2n-3}$ with two double bonds. Like an alkyl group, an alkenyl group can be straight or branched. Examples of an alkenyl group include, but are not limited to, allyl, isoprenyl, 2-butenyl, and 2-hexenyl.

As used herein, the term "cycloalkyl", used alone or as part of a larger moiety (e.g., as in "cycloalkylalkyl" or "halocycloalkylalkoxy"), refers to a saturated carbocyclic mono-, bi-, or tri-cyclic (fused or bridged or spiral) ring system. It can contain 3 to 12 (e.g., 3 to 10, or 5 to 10) carbon atoms. Examples of cycloalkyl groups include, but are not limited to, cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, or ((aminocarbonyl)cycloalkyl) cycloalkyl.

As used herein, the term "cycloalkenyl", used alone or as part of a larger moiety (e.g., as in "cycloalkenylalkyl" or "cyanocycloalkenylalkoxy"), refers to a non-aromatic carbocyclic ring system having one or more double bonds. It can contain 3 to 12 (e.g., 3 to 10, or 5 to 10) carbon atoms. Examples of cycloalkenyl groups include, but are not limited to, cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

As used herein, the term "heterocycloalkyl", used alone or as part of a larger moiety (e.g., as in "heterocycloalkylalkyl" or "heterocycloalkoxy"), refers to a 3- to 16-membered mono-, bi-, or tri-cyclic (fused or bridged or spiral)) saturated ring structure, in which one or more of the ring atoms is a heteroatom (e.g., N, O, S, or combinations thereof). In addition to the heteroatom(s), the heterocycloalkyl can contain 3 to 15 carbon atoms (e.g., 3 to 12 or 5 to 10). Examples of a heterocycloalkyl group include, but are not limited to, piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-azabicyclo[2.2.2]octyl, 3-aza-bicyclo[3.2.1]octyl, and 2,6-dioxa-tricyclo[3.3.1.03,7]nonyl. A monocyclic heterocycloalkyl group can be fused with a phenyl moiety such as tetrahydroisoquinoline.

As used herein, the term "aryl", used alone or as part of a larger moiety (e.g., as in "aralkyl", "aralkoxy," or "haloaryloxyalkyl"), refers to a monocyclic (e.g., phenyl); bicyclic (e.g., indenyl, naphthalenyl, or tetrahydronaphthyl); and tricyclic (e.g., fluorenyl, tetrahydrofluorenyl, tetrahydroanthracenyl, or anthracenyl) ring system in which the monocyclic ring system is aromatic (e.g., phenyl) or at least one of the rings in a bicyclic or tricyclic ring system is aromatic (e.g., phenyl). The bicyclic and tricyclic groups include, but are not limited to, benzo-fused 2- or 3-membered carbocyclic rings. For instance, a benzo-fused group includes phenyl fused with two or more $C_{4-8}$ carbocyclic moieties.

As used herein, the term "heteroaryl" refers to a monocyclic, bicyclic, or tricyclic ring system having 5 to 15 ring atoms wherein at least one of the ring atoms is a heteroatom (e.g., N, O, S, or combinations thereof) and in which the monocyclic ring system is aromatic or at least one of the rings in the bicyclic or tricyclic ring systems is aromatic. It can contain e.g., 5 to 12 or 8 to 10 ring atoms. A heteroaryl group includes, but is not limited to, a benzo-fused ring system having 2 to 3 rings. For example, a benzo-fused group includes benzo fused with one or two 4- to 8-membered heterocycloalkyl moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzithiazolyl, xanthenyl, thioxanthenyl, phenothiazinyl, dihydroindolyl, benzo[1,3]dioxolyl, benzo[b]furyl, benzo[b]thiophenyl, indazolyl, benzimidazolyl, benzthiazolyl, puryl, quinolinyl, quinazolinyl, phthalazyl, quinazolyl, quinoxalyl, isoquinolinyl, 4H-quinolizyl, benzo-1,2,5-thiadiazolyl, and 1,8-naphthyridyl.

As used herein, the term "bridged bicyclic ring system" refers to a bicyclic heterocycloalkyl ring system or bicyclic cycloalkyl ring system in which the rings have at least two common atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxatricyclo[3.3.1.0³,⁷]nonyl.

As used herein, the term "halo" refers to fluoro, chloro, bromo, or iodo.

As used herein, the term "independent", e.g., as in "optionally substituted with one or more independent $R^3$ groups", means that when the number of substituent is more than one (e.g., two or three), these multiple substituents can be the same or different.

As used herein, the term "optionally" (e.g., as in "optionally substituted with") means that the moiety at issue is either substituted or not substituted, and that the substitution occurs only when chemically feasible. For instance, H cannot be substituted with a substituent; and a covalent bond or —C(═O)— group cannot be substituted with a substituent.

As used herein, an "oxo" group refers to ═O.

As used herein, a "carbonyl" group refers to —C(O)— or —C(═O)—.

As used herein, a "cyano" group refers to —CN.

As used herein, a "urea" group refers to the structure —NR$_X$—CO—NR$_Y$R$_Z$ when terminally included in a compound or —NR$_X$—CO—NR$_Y$— when internally included in a compound.

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a Spiro-bicyclic ring system, e.g., both rings share one common atom.

As one of ordinary skill in the art will recognize, combinations of substituents envisioned by this invention are those combinations that result in the formation of stable or chemically feasible compounds.

For convenience and as commonly understood, the term "optionally substituted" only applies to the chemical entities that can in fact be substituted with suitable substituents, not to those that chemically cannot be substituted. Thus, it is effective only when chemically possible. For instance, when "$R^2$ is H, alkyl, aryl, heteroaryl, —C(═O)-alkyl, —C(═O)-aryl, or —C(═O)-heteroaryl, each of which is optionally substituted with one or more independent $Q^1$ groups," although the phrase "each of which is optionally substituted with one or more independent $Q^1$ groups" gramatically applies to H, but since H (hydrogen atom) chemically cannot be substituted, the phase therefore does not actually apply to H. As another example, when "L' is a covalent bond, —C(═O)—, —C(═O)-alkylene, or alkylene, each of which is optionally substituted with one or more independent $R^4$ groups," the phrase "each of which is optionally substituted with one or more independent $R^4$ groups" will not apply to a covalent bond or —C(═O)— since these two are not chemically possible to be substituted.

As used herein, the term "stable" or "chemically feasible" refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "or" as in, e.g., "one or more independent halo, alkoxy, alkyl . . . cyano, oxo, or optionally substituted heterocycloalkyl" (emphasis added) can mean "or" or "and." In other words, under this scenario, for instance, the substituents (when more than one) can be two halo groups or one halo and one alkyl. In another example, "VEGFR2 or c-Met" can mean "VEGFR2," "c-Met," or "VEGFR2 and c-Met."

As used herein, the phrase "pharmaceutically acceptable salt(s)" means those salts of the compounds of the invention that are safe and effective for internal use (or topical use, if needed) in a subject (e.g., a mammal such as a human patient, a dog, or a cat) and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, a "subject" for treatment generally refers to and thus may be interchangeable with a "patient," such as an animal (e.g., a mammal such as a human, a cat, or a dog).

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., *Scientific Tables*, Geigy Pharmaceuticals, Ardsley, N.Y., 537 (1970).

Unless otherwise specified, all cyclic radical moieties identified herein can be bonded to another moiety in any of the formulae included herein at any of its ring atoms.

Unless otherwise stated, the structures depicted herein are meant to include all isomeric (e.g., enantiomeric, diastereomeric, and geometric (or conformational)) forms of the structure; for example, the R and S configurations for each asymmetric center, (Z) and (E) double bond isomers, and (2) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "therapeutically effective amount" of a compound of this invention refers to an amount effective, when administered to a human or non-human patient, for the treatment of a disease, e.g., a therapeutically effective amount may be an amount sufficient to treat a disease or disorder responsive to kinase inhibition. The therapeutically effective amount may be ascertained experimentally, for example by assaying blood concentration of the chemical entity, or theoretically, by calculating bioavailability.

As used herein, the term "significant" refers to any detectable change that is statistically significant in a standard parametric or nonparametric test of hypothesis such as Student's T-test, where p<0.05.

As used herein, the term "patient" or "subject" refers to an animal, such as a mammal, for example a human, a dog, or a cat, that has been or will be the object of treatment, observation or experiment. The methods of the invention can be useful in both human therapy and veterinary applications.

As used herein, the term "angiogenesis kinase" refers to a kinase involved in angiogenesis. Its examples include VEGFR2, PDGFRβ, and c-Met.

As used herein, the term "inhibition" refers to a decrease in kinase activity as a direct or indirect response to the presence of compounds of Formula I or II, relative to the activity of the kinase in the absence of the compound. The decrease may be due to the direct interaction of the compound with the kinase, or due to the interaction of the compound with one or more other factors that in turn affect kinase activity. For example, the presence of the compound may, for example, decrease kinase activity by directly binding to the kinase, by causing (directly or indirectly) another factor to decrease the kinase activity, or by (directly or indirectly) decreasing the amount of kinase present in the cell or organism.

As used herein, the term "treatment" or "treating" refers to any treatment of a disease in a patient, including: (a) preventing the disease, that is, causing the clinical symptoms of the disease not to develop; (b) inhibiting the disease; (c) slowing or arresting the development of clinical symptoms; or (d) relieving the disease, that is, causing the regression of clinical symptoms.

As used herein, the term "diseases or disorders responsive to kinase inhibition" refer to pathologic conditions that depend, at least in part, on the activity of one or more protein kinases, for example, angiogenesis kinases. Kinases either directly or indirectly participate in the signal transduction pathways of a variety of cellular activities including cell proliferation, differentiation, and invasion. Diseases responsive to kinase inhibition include but are not limited to tumor growth, angiogenesis supporting solid tumor growth, and diseases characterized by excessive growth of local vasculature such as diabetic retinopathy, macular degeneration, and inflammation.

As used herein, the term "change in angiogenesis" refers to a change in the vascular network or quality of vasculature. Change in angiogenesis may be measured by many parameters and, for instance, may be assessed by delayed appearance of neovascular structures, slowed development of neovascular structures, decreased occurrence of neovascular structures, changes in vascular permeability, changes in blood flow, slowed or decreased severity of angiogenesis-dependent disease effects, arrested vasculature growth, or regression of previous vasculature.

DETAILED DESCRIPTION OF THE INVENTION

The present invention provides compounds of Formula I or II, or a pharmaceutically acceptable salt thereof.

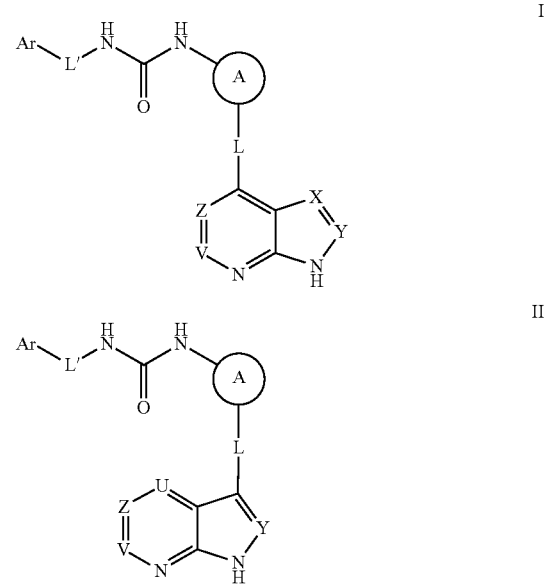

In Formula I or II:

U, V, X, Y, and Z are each independently N or C—$R^1$;

L is O, $S(O)_n$, N—$R^2$, or alkylene which is optionally substituted with one or more independent $R^3$ group;

$R^2$ is H, alkyl, aryl, heteroaryl, —C(=O)-alkyl, —C(=O)-aryl, or —C(=O)-heteroaryl, each of which is optionally substituted with one or more independent $Q^1$ groups;

L' is a covalent bond, —C(=O)—, —C(=O)-alkylene, or alkylene, and is optionally substituted with one or more independent $R^4$ group;

A is

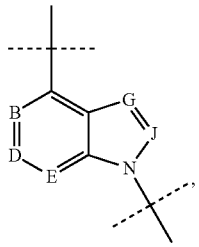
A1

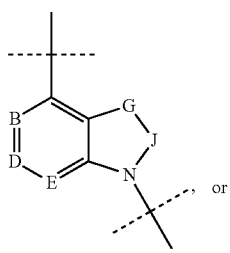
A2
, or

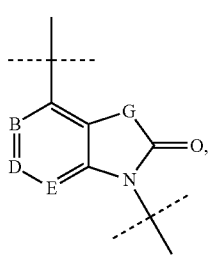
A3 wherein B, D, E, G, and J are each independently N or C—$R^5$; the 5-membered ring of A is connected to L and the 6-membered ring of A is connected to the urea group in Formula I or II;

Ar is aryl or heteroaryl, each of which is optionally substituted with one or more independent $R^6$ groups;

$R^1$, $R^3$, $R^4$, $R^5$, and $R^6$ are each independently H, halo, —CN, —$CF_3$, —$NO_2$, —$NH_2$, —OH, —$OCF_3$, —$OCH_3$, —$CO_2H$, alkyl, alkenyl, alkynyl, cycloalkyl, heterocycloalkyl, arylalkyl, or heteroarylalkyl, each of which is optionally substituted with one or more independent $Q^2$ groups;

$Q^1$ and $Q^2$ are each independently H, halo, —CN, —$CF_3$, —$OCF_3$, —$NO_2$, oxo, alkyl, alkenyl, alkynyl, cycloalkyl, heterocycloalkyl, aryl, heteroaryl, heterocycloaryl, —$OR^7$, —$S(O)_nR^8$, —$NR^9R^{10}$, —$SO_2NR^9R^{10}$, —$C(O)R^{11}$, —$C(O)NR^9R^{10}$, —$C(O)OR^{12}$, —$OC(O)R^{13}$, —$NR^9C(O)R^{11}$, —$NR^9S(O)_2R^{14}$, —$NR^{15}C(O)NR^9R^{10}$, —$NR^{15}S(O)_2NR^9R^{10}$ or —$NR^{15}S(O)NR^9R^{10}$, each of which is optionally substituted with one or more independent H, halo, —CN, —OH, —$NH_2$, —$NO_2$, oxo, —$CF_3$, —$OCF_3$, —$CO_2H$, —$S(O)_nH$, alkyl, aryl, heteroaryl, cycloalkyl, heterocycloalkyl, or heterocycloaryl, each of which may be partially or fully halogenated, or —O-alkyl which may be partially or fully halogenated;

$R^7$, $R^8$, $R^{11}$, $R^{12}$, $R^{13}$, $R^{14}$, or $R^{15}$ are each independently H, alkyl, alkenyl, alkynyl, cycloalkyl, heterocycloalkyl, aryl, heteroaryl, or heterocycloaryl;

$R^9$ and $R^{10}$ are each independently H, alkyl, alkenyl, alkynyl, cycloalkyl, heterocycloalkyl, aryl, heteroaryl, or heterocycloaryl; or when in —$NR^9R^{10}$, $R^9$ and $R^{10}$, together with the nitrogen atom to which they are attached to, form a 3- to 12-membered saturated or unsaturated ring, wherein said ring optionally includes one or more heteroatoms each independently being O, N, or $S(O)_n$; and n is 0, 1, or 2.

General Synthetic Schemes

Compounds of this invention may be synthesized from commercially available or known starting materials by known methods. Exemplary synthetic routes to produce these compounds are provided in the schemes shown below wherein the substituents are as defined herein unless otherwise noted. These generic schemes are for illustration only and not limiting, and they can be applied to preparation of other compounds that include different variables than those explicitly shown below.

The following abbreviations are used:
NMR=Nuclear magnetic resonance
TMS=Tetramethylsilane
DCM=Dichloromethane
THF=Tetrahydrofuran
EtOAc=Ethyl acetate
MeCN=Acetonitrile
DMSO=Dimethylsulfoxide
Boc=t-Butyloxycarbonyl
DMF=N,N-Dimethylformamide
DME=Dimethyl ether
TFA=Trifluoroacetic acid
$CDCl_3$=Deuterated chloroform
DMSO-$d_6$=Deuterated dimethylsulfoxide
TLC=Thin layer chromatography
HPLC=High performance liquid chromatography
Min=Minute(s)
h=Hour(s)
d=Day(s)
RT or rt=Room temperature
$t_R$=Retention time
L=Liter
mL=Milliliter
mmol or mM=Millimole
g=gram
mg=Milligram
LG=Leaving Group
PG=Protecting Group Scheme 1:

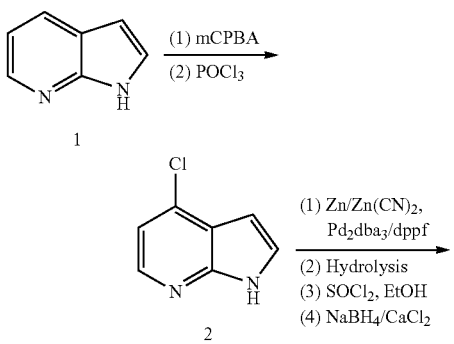

-continued

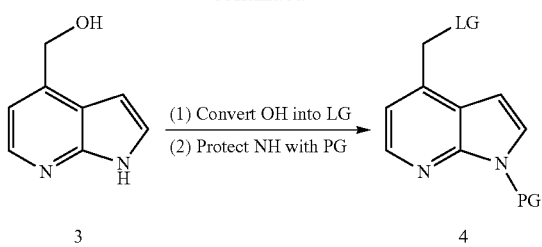

Intermediate 4 can be prepared in several steps from commercially available 7-azaindole (1) according to Scheme 1 illustrated above. Specifically, 4-chloro-7-azaindole (2) was obtained by oxidation of starting material 1 with an oxidant, such as m-chloroperoxybenzoic acid (mCPBA) or hydrogen peroxide or other peroxyacid, followed by treatment with POCl$_3$ or SOCl$_2$. Compound 2 was then converted into alcohol 3 by Pd-catalyzed cyanation, base- or acid-mediated hydrolysis, esterification, and reduction. The hydroxyl group in compound 3 was replaced with a leaving group (LG), such as Cl, Br, I, MeSO$_3$—, TfO—, and TsO—, by reacting with SOCl$_2$, CBr$_4$+PPh$_3$, PBr$_3$, MeSO$_2$Cl, Tf$_2$O, TsCl, etc. The amino group (NH) on the azaindolyl ring was protected by a commonly used nitrogen protecting group (PG), e.g., Boc or Cbz or other carbamate, PhSO$_2$— or other organosulfonyl, p-methoxybenzyl (PMB), methoxymethyl (MOM), [β-(trimethylsilyl)ethoxy]methyl (SEM), etc.

Scheme 2:

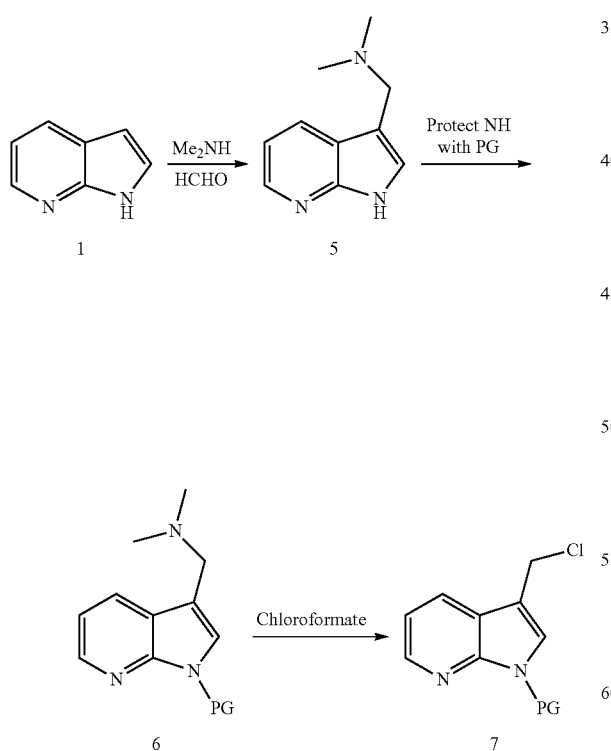

Intermediate 7 can be easily prepared in three steps from commercially available 7-azaindole (1). On treatment with Me$_2$NH and formaldehyde, compound 1 was converted to amine 5, which was protected with a nitrogen protecting group (PG), e.g., Boc or Cbz or other carbamate, PhSO$_2$— or other organosulfonyl, p-methoxybenzyl (PMB), methoxymethyl (MOM), [β-(trimethylsilyl)ethoxy]methyl (SEM), etc, to give compound 6. Compound 6 was converted to chloride 7 by reacting with a chloroformate, such as methyl, ethyl, n-propyl, i-propyl, n-buyl, or i-butyl chloroformate.

Scheme 3:

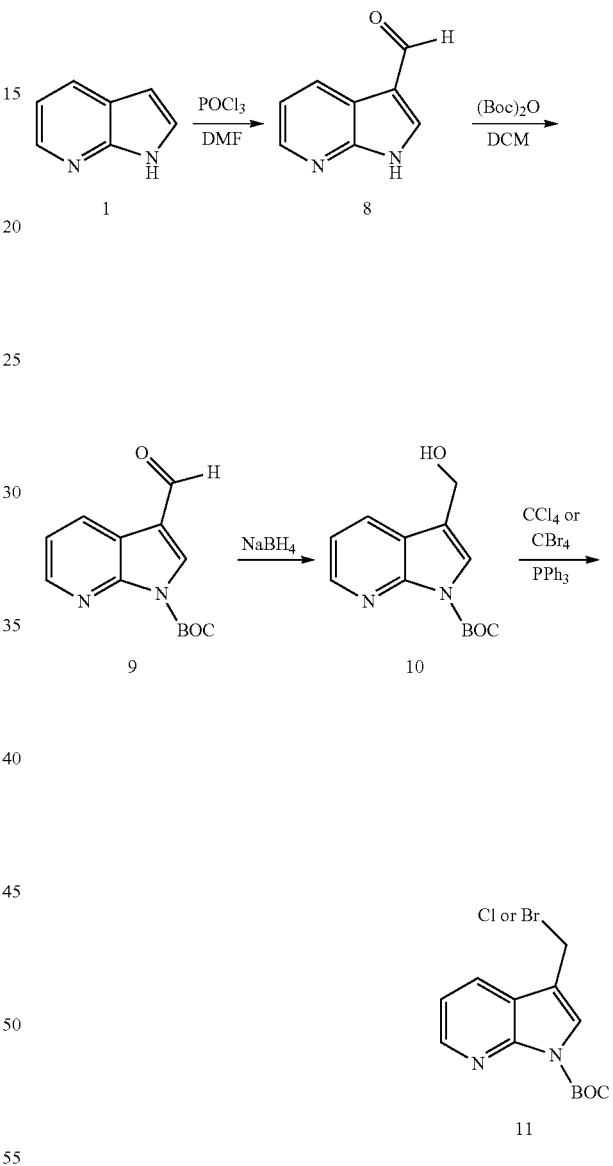

Intermediates 11 can be prepared in four steps from commercially available 7-azaindole (1) as shown in Scheme 3. On treatment with DMF and POCl$_3$, compound 1 was converted to aldehyde 8, which was protected by a Boc group to give compound 9. Compound 9 was then reduced to a primary alcohol 10 with NaBH$_4$. Treatment of this alcohol 10 with carbon tetrachloride/triphenylphosphine or carbon tetrabromide/triphenylphosphine afforded a corresponding chloride or bromide compound 11.

Scheme 4:
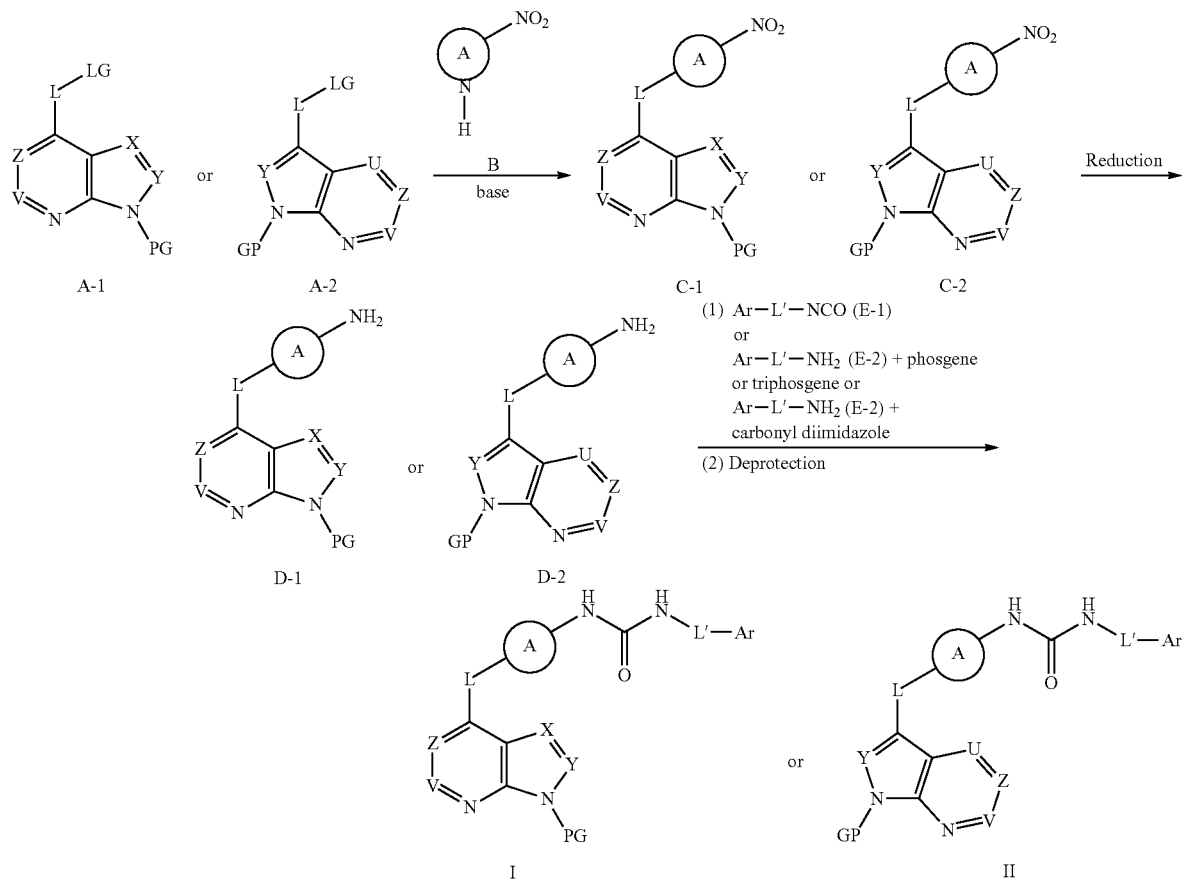
For example:
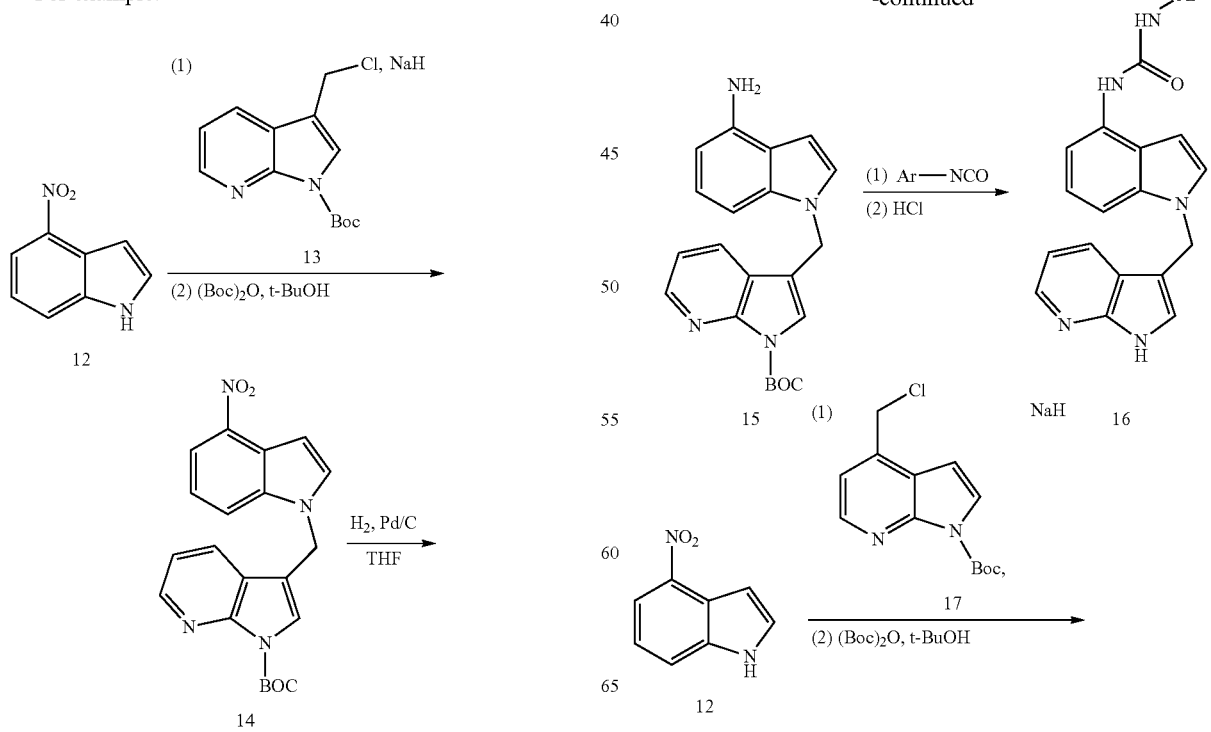

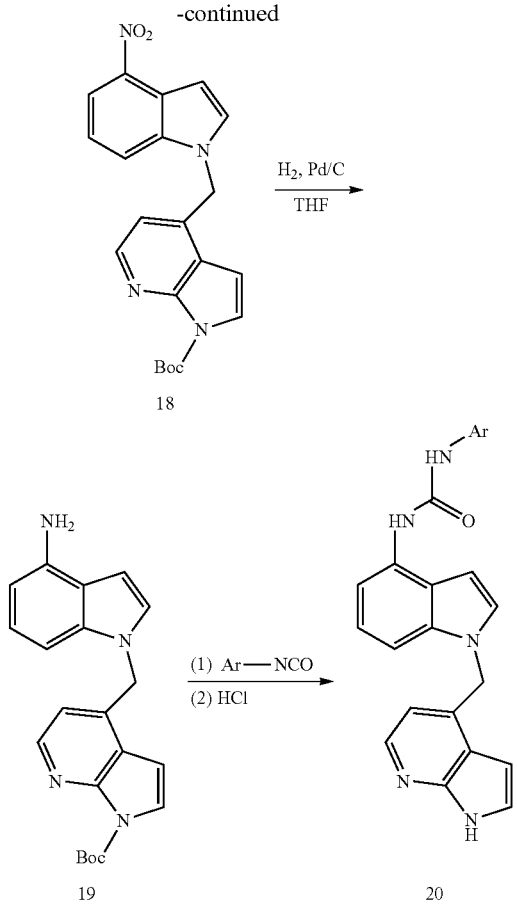

Scheme 4 shows the synthesis of exemplary compounds of Formula I or II. Intermediate A-1 or A-2, prepared by Schemes 1-3, reacted with commercially available monocyclic or bicyclic aryl or heteroaryl nitro compounds under basic conditions to generate compound C-1 or C-2. Reduction of nitro group by catalytic hydrogenation (commonly used catalysts are Pd- or Pt-based), Fe/HCl or Zn/HOAc, or $SnCl_2$ to give amines D-1 or D-2, which reacted with isocyanate E-1 or amine E-2 mediated by phosgene or triphosgene or carbonyl diimidazole to afford the urea product I or II after removal of protecting group (PG) under acidic or basic conditions. For example, 4-nitroindole (12) was alkylated with chloride 13 in the presence of NaH, followed by protection with Boc to give compound 14. The nitro group of 14 was reduced into amino group by Pd/C-catalyzed hydrogenation to generate amine 15. Compound 15 reacted readily with aryl isocyanate to afford urea product, which was deprotected by HCl treatment to form the final product 16. Following the same reaction sequence, urea 20 was generated from 4-nitroindole (12) and chloride 17.

Scheme 5:

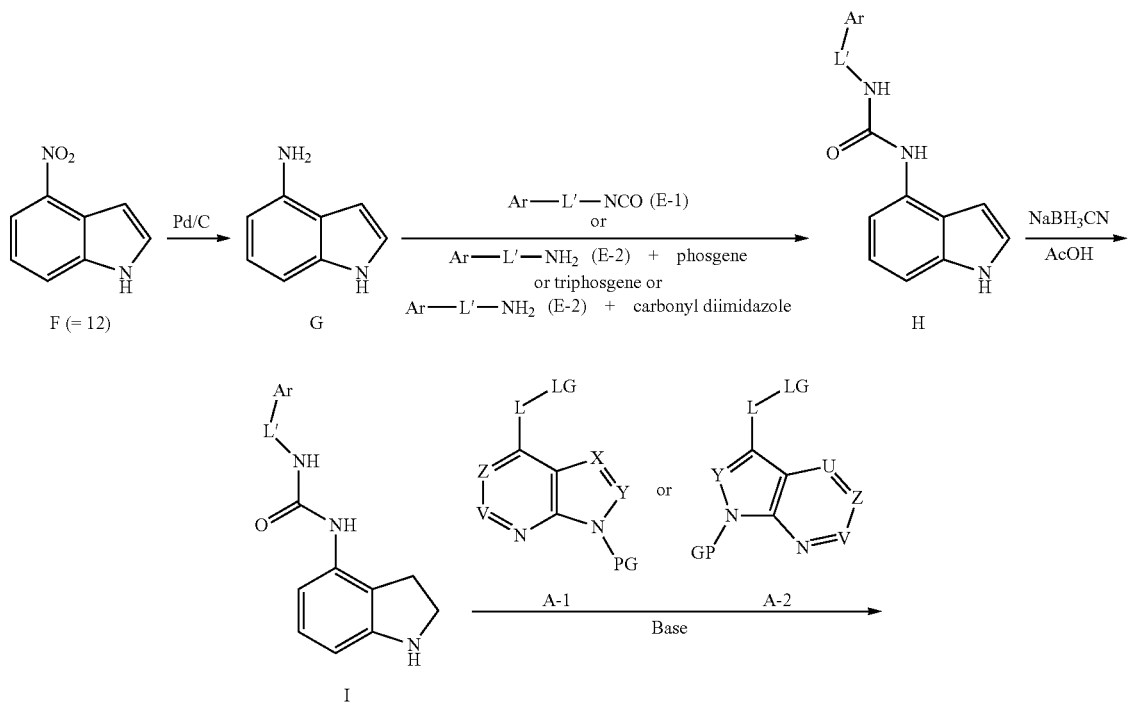

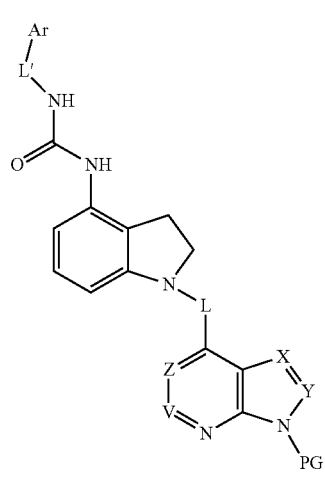
J-1
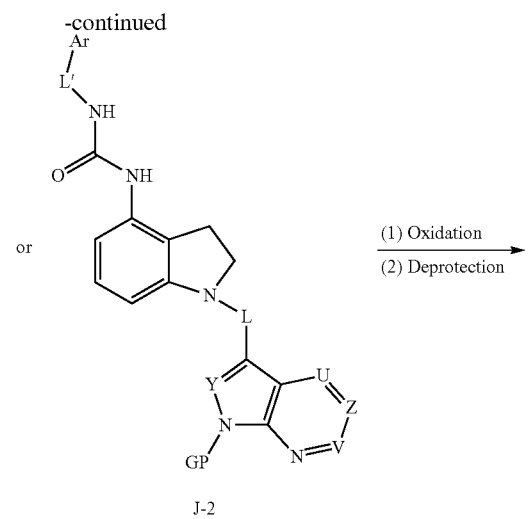
J-2
(1) Oxidation
(2) Deprotection →
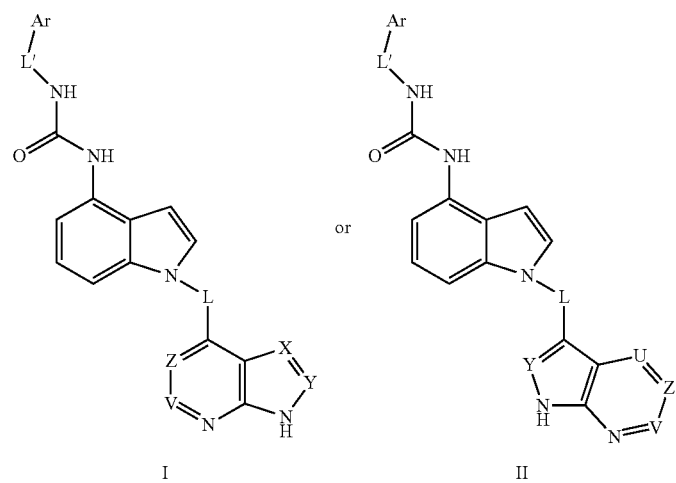
I  or  II
For example:
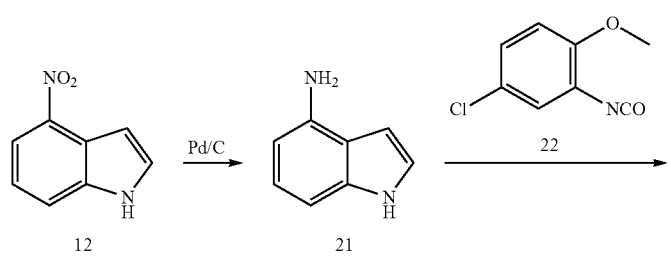

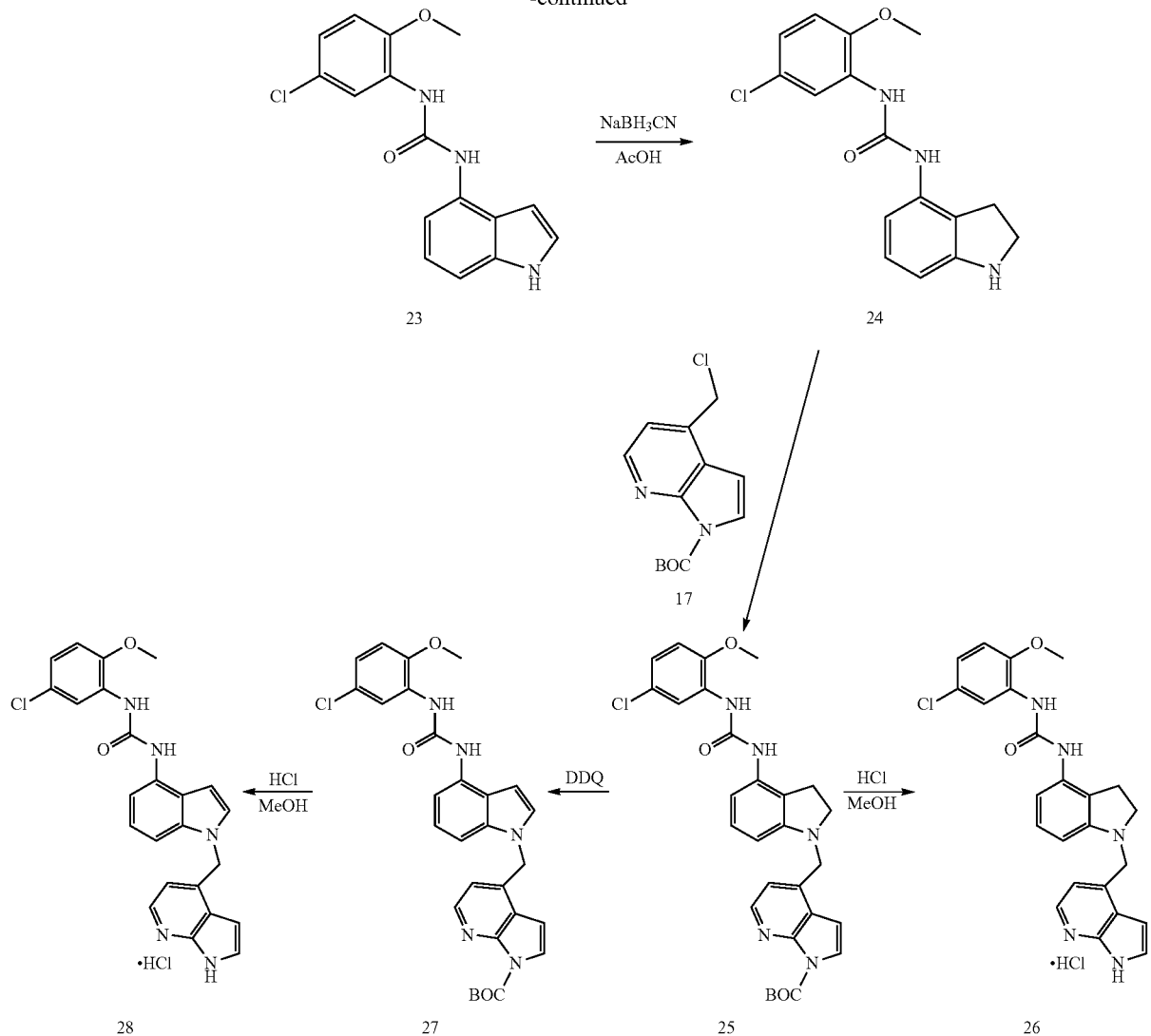

Scheme 5 shows another way to synthesize compounds of Formula I or II. Commercially available 4-nitroindole F was reduced to 4-aminoindole G, which reacted with isocyanate E-1 or amine E-2 mediated by phosgene or triphosgene or carbonyl diimidazole to afford the urea product H. Upon treatment with NaBH₃CN+AcOH, H was converted into compound I. Alkylation of I with intermediate A-1 or A-2, prepared in Schemes 1-3 gave compounds J-1 or J-2, which can be converted to product I or II after removal of protecting group (PG) under acidic or basic conditions. For example, hydrogenation of 4-nitroindole (12) yielded amine 21, which reacted with isocyanate 22 to afford urea 23. Compound 23 was reduced into indolinyl compound 24, which was successfully alkylated with 17 to generate compound 25. Compound 25 was either deprotected by HCl to form target compound 26 or oxidized by DDQ into 27, which gave target compound 28 after removal of Boc group.

GENERAL EXPERIMENTAL AND ANALYTICAL METHODS

Unless otherwise noted, all materials/reagents were obtained from commercial suppliers and used without further purification. NMR spectra were recorded on a Bruker or Varian 300 or 400 MHz instrument at ambient temperature with TMS or the residual solvent peak as the internal standard. The line positions or multiples are given in ppm (δ) and the coupling constants (J) are given as absolute values in Hertz (Hz). The multiplicities in ¹H NMR spectra are abbreviated as follows: s (singlet), d (doublet), t (triplet), q (quartet), quint (quintet), m (multiplet), m$_c$ (centered multiplet), br or broad (broadened). Mass spectra (MS) were measured by ESI methods. Reactions were monitored by thin layer chromatography (TLC) on silica gel 60 F-254 (0.2 mm) and visualized using UV light. Flash chromatography was performed with silica gel (400-230 mesh).

Preparation I

2-Methoxy-5-chlorophenyl isocyanate (Int-4)

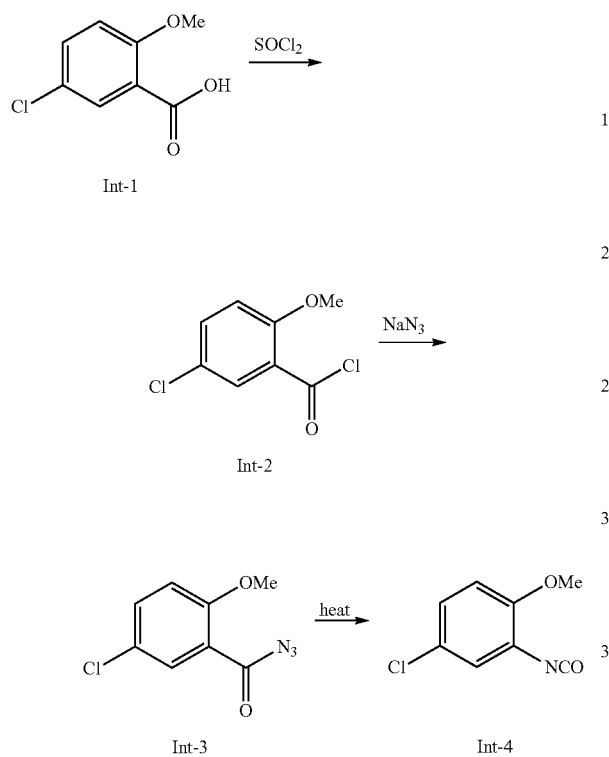

To a suspension of 2-methoxy-5-chlorobenzoic acid (Int-1, 18.7 g, 100 mmol) in dry dichloromethane (120 mL) under nitrogen was added dropwise thionyl chloride (25 mL, 130 mmol). After the reaction mixture was refluxed for 2 h, a clear solution was formed. Evaporation of excess thionyl chloride and solvent gave a solid product Int-2, which was used directly in the next step without purification.

To a solution of acid chloride Int-2 in acetone (100 mL) under nitrogen was added sodium azide (7.8 g, 120 mmol) and 50 mL water. After being stirred for 2 h at room temperature, another 50 mL water was added. The mixture was filtered and the filter cake was washed with water and dried to afford acyl azide Int-3 as white solid, which was used directly in the next step without purification.

The acyl azide Int-3 obtained from previous step was dissolved in dry toluene (100 mL). The resulted solution was added slowly to an empty round-bottom flask preheated in an oil bath at 110° C. Evolution of nitrogen was observed, which ceased after about 1 h of addition. The reaction mixture was then cooled to room temperature and solvent was removed under reduced pressure to yield a yellowish solid residue, which was recrystallized from petroleum ether to afford the desired product Int-4 as white crystals (10.3 g, 56% for 3 steps), which turn yellowish on standing.

MS (ESI$^+$): m/z 238.0 (100) [M+MeOH+Na, $^{35}$Cl]$^+$, 240.0 (33) [M+MeOH+Na, $^{37}$Cl]$^+$.

Preparation II 1-(t-Butyloxycarbonyl)-4-chloromethyl-7-azaindole (Int-11)

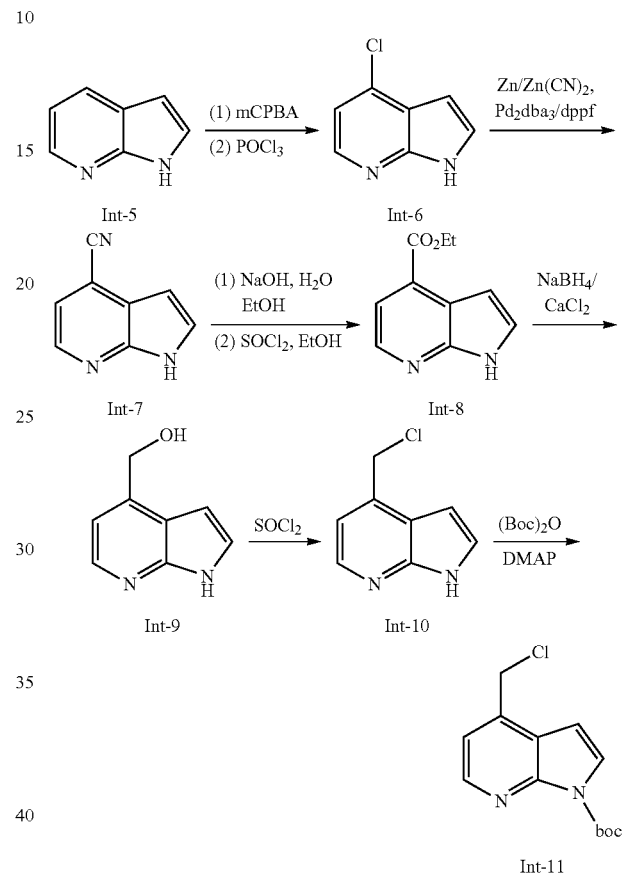

To a solution of 7-azaindole (Int-5, 23.6 g, 200 mmol) in DME/heptane (1:2, 300 mL) was added 3-chloroperoxybenzoic acid (85 wt %, 44.7 g, 220 mmol) portion-wise. The slurry was stirred at room temperature for 3 h. The precipitate was collected by filtration and washed with heptane (100 mL). After dried, 51.9 g of 7-azaindole N-oxide 3-chlorobenzoate was obtained (51.9 g, 89%). mp 140-143° C.

To 7-azaindole N-oxide 3-chlorobenzoate (51.9 g, 178 mmol) was added phosphorus oxychloride (200 mL) at room temperature. The solution was heated with stirring at 85-90° C. overnight. Phosphorus oxychloride was distilled off under reduced pressure. Water was added, and the mixture was basified to pH 9 with 50% sodium hydroxide aqueous solution. The slurry was allowed to cool to room temperature and filtered. The solids collected was suspended in water (200 mL), stirred, filtered, and dried to afford the product Int-6 (21.7 g, 80%).

$^1$H NMR (400 MHz, CDCl$_3$) δ 11.40 (brs, 1H), 8.24 (d, J=5.2 Hz, 1H), 7.43 (d, J=3.6 Hz, 1H), 7.15 (d, J=5.2 Hz, 1H), 6.63 (d, J=3.6 Hz, 1H).

A suspension of 4-chloro-7-azaindole (Int-6, 18.2 g, 119 mmol) in dimethylacetamide (100 mL) was degassed and then filling with nitrogen. To this suspension was added zinc powder (720 mg, 11 mmol), diphenylphosphinoferrocene (2.1 g, 3.8 mmol), zinc cyanide (8.2 g, 69.8 mmol), and tris(dibenzylideneacetone) dipalladium (1.74 g, 1.9 mmol) at room temperature. The mixture was heated at 120° C. under nitrogen for 2 h. After cooled to room temperature, water (300 mL) was added, and the mixture was extracted with ethyl acetate, the organic layer was washed sequentially with saturated aqueous ammonium chloride, brine, dried over anhydrous sodium sulfate, filtered, and concentrated under reduced pressure to give the crude product, which was purified by flash column chromatography to provide Int-7 (12.3 g, yield: 70%).

MS (ESI+): m/z 144.1 [M+H]+.

A mixture of Int-7 (11.5 g, 80 mmol), sodium hydroxide (32 g, 800 mmol), water (100 mL), and ethyl alcohol (100 mL) was heated to reflux. After 6 h, the reaction mixture was cooled to room temperature and neutralized and acidified with concentrated hydrochloric acid. The solids were collected by filtration to afford 7-azaindole-4-carboxylic acid (10.4 g, 80%), which was used directly in the next step without purification.

A mixture of 7-azaindole-4-carboxylic acid (10.4 g, 64 mmol), thionyl chloride (17.8 g, 150 mmol), and ethyl alcohol (150 mL) was heated to reflux. After the reaction was complete (by TLC), the mixture was concentrated, basified to pH 9 with aqueous potassium carbonate, and extracted with ethyl acetate. The organic layer was washed with water, brine, dried over anhydrous sodium sulfate, filtered, and concentrated under reduced pressure to dryness. The residue was purified by flash column chromatography to give Int-8 (11.0 g, 90%).

$^1$H NMR (400 MHz, CDCl$_3$) δ 10.51 (brs, 1H), 8.45 (d, J=4.4 Hz, 1H), 7.75 (d, J=4.4 Hz, 1H), 7.54 (s, 1H), 7.08 (d, J=2.0 Hz, 1H), 4.50 (q, J=7.2 Hz, 2H), 1.49 (t, J=7.2 Hz, 3H).

To the solution of Int-8 (9.5 g, 50 mmol) in THF (150 mL) was added sodium borohydride (3.8 g, 100 mmol) and calcium chloride (11.1 g, 100 mmol), and the mixture was heated to reflux for 6 h. After the reaction was complete (by TLC), methanol and water were added, the resulting mixture was extracted with ethyl acetate. The organic layer was washed by water, brine, dried over anhydrous sodium sulfate, filtered, and concentrated under reduced pressure to afford Int-9 (5.0 g, 67%).

$^1$H NMR (400 MHz, DMSO-d$_6$) δ 11.84 (brs, 1H), 8.22 (d, J=5.6 Hz, 1H), 7.51 (t, J=2.8 Hz, 1H), 7.31 (d, J=6.4 Hz, 1H), 6.74 (q, J=1.6 Hz, 1H), 5.65 (t, J=6.0 Hz, 1H), 4.92 (d, J=5.2 Hz, 2H).

A mixture of Int-9 (4.4 g, 30 mmol) and thionyl chloride (11.9 g, 100 mmol) in DCM (100 mL) was stirred at room temperature overnight. Then the mixture was concentrated, basified to pH 9 with aqueous potassium carbonate, and extracted with ethyl acetate. The organic layer was washed with water, brine, dried over anhydrous sodium sulfate, filtered, and concentrated under reduced pressure to dryness. The residue was purified by flash column chromatography to provide Int-10 (4.3 g, 87%).

MS (ESI+): m/z 167.0 (100) [M+H, $^{35}$Cl]+, 169.0 (33) [M+H, $^{37}$Cl]+.

A round-bottom flask was charged with Int-10 (4.2 g, 25 mmol), (Boc)$_2$O (10.9 g, 50 mmol), and 4-dimethylaminopyridine (cat.), triethylamine (75 mmol) and DCM (80 mL). The mixture was stirred at room temperature for 6 h, then concentrated to dryness. The residue was purified by flash column chromatography to provide Int-11 (6.1 g, 91%).

Preparation III 1-(t-Butyloxycarbonyl)-3-chloromethyl-7-azaindole (Int-14)

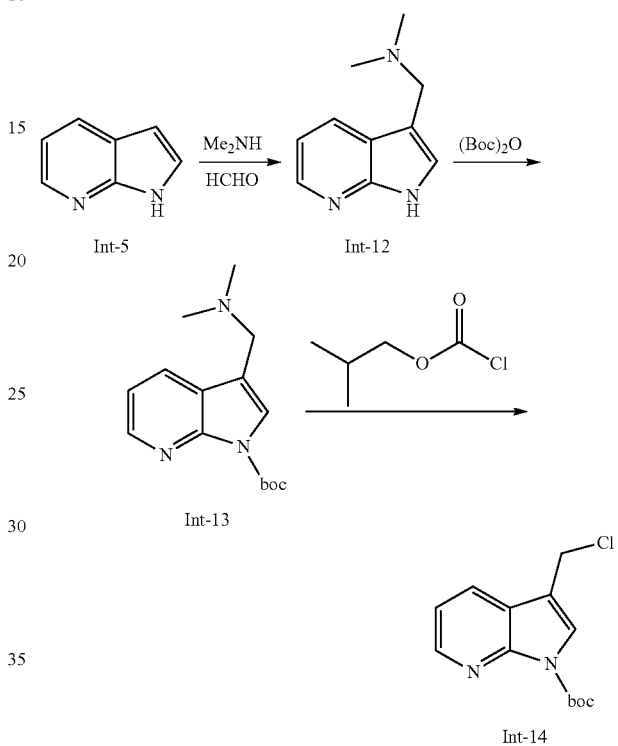

Isopropyl alcohol (100 mL) was added to a mixture of 7-azaindole (Int-5, 8.3 g, 70 mmol), dimethylamine hydrochloride (5.7 g, 70 mmol), and formaldehyde (38% aqueous solution, 5.5 g, 70 mmol). The reaction mixture was stirred at room temperature overnight, and then refluxed for 2 h. The resulting suspension was evaporated to dryness in vacuo, water (50 mL) and conc. hydrochloric acid (5 mL) were added, and the water layer was extracted with ethyl acetate, dried with sodium sulfate, and concentrated to give product Int-12, which was used directly in the next step without purification.

$^1$H NMR (400 MHz, DMSO-d$_6$) δ 11.44 (s, 1H), 8.18, 8.17 (dd, J=4.8, 1.2 Hz, 1H), 7.98, 7.96 (dd, J=7.6, 1.6 Hz, 1H), 7.32 (d, J=2.8 Hz, 1H), 7.03, 7.01 (dd, J=8.0, 4.8 Hz, 1H), 3.51 (s, 2H), 2.12 (s, 6H).

A round-bottom flask was charged with Int-12 from previous step, (Boc)$_2$O (30 g, 140 mmol), 4-dimethylaminopyridine (cat.), triethylamine (210 mmol) and DCM (80 mL). The mixture was stirred at room temperature overnight, concentrated to dryness, purified by flash column chromatography to afford product Int-13 (12.7 g, 66% for two steps).

Under an atmosphere of nitrogen, isobutyl chloroformate (6.8 g, 50 mmol) was added to Int-13 (12.4 g, 45 mmol) in toluene (100 mL), the reaction mixture was stirred overnight. Water was added, and the mixture was extracted with ethyl acetate, concentrated, and purified by flash column chromatography to give product Int-14 (1.6 g, 12% yield).

$^1$H NMR (400 MHz, CDCl$_3$) δ 8.55 (d, J=4.4 Hz, 1H), 8.01 (d, J=7.2 Hz, 1H), 7.69 (s, 1H), 7.27-7.24 (m, 1H), 4.76 (s, 2H), 1.67 (s, 9H).

Preparation IV 1-(t-Butyloxycarbonyl)-3-chloromethyl-7-azaindole (Int-14)

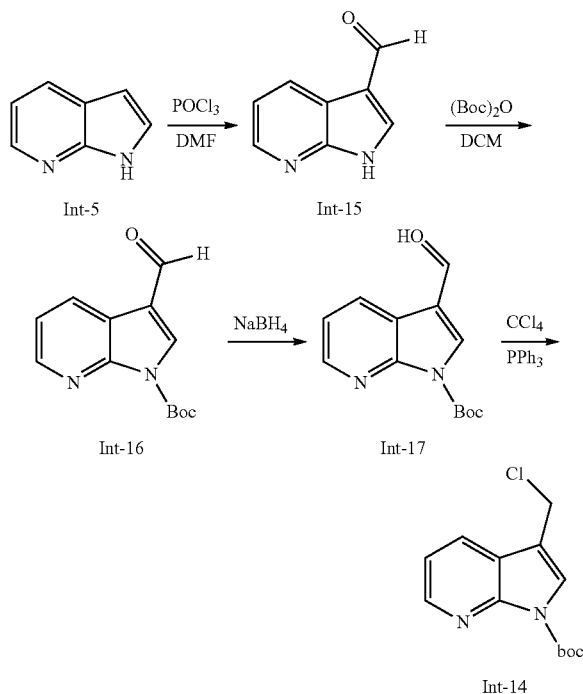

A three-necked flask was charged with dimethylformamide (33 mL, 425 mmol) and cooled in an ice-salt bath. Phosphorus oxychloride (35 mL, 340 mmol) was added with stirring over a period of 0.5 h. After another 10 min, 7-azaindole (Int-5, 10.8 g, 91 mmol) was added while the temperature in the flask should not rise above 10° C. The resulting mixture was then stirred at 80° C. for 48 h. After cooled to rt, crushed ice was added producing a clear, cherry-red aqueous solution, which was neutralized with sodium hydroxide (s). The mixture was extracted with ethyl acetate and the combined organic layers were concentrated and purified by flash column chromatography to give product Int-15 (6.6 g, 50%).

A round-bottom flask was charged with Int-15 (6.6 g, 45 mmol), (Boc)$_2$O (10.7 g, 50 mmol), 4-dimethylaminopyridine (55 mg, 0.45 mmol), triethylamine (13 g, 130 mmol), and DCM (50 mL). The mixture was stirred at room temperature overnight, concentrated to dryness, and purified by flash column chromatography to afford product Int-16 (9.8 g, 89%).

A mixture of 1-(tert-butyloxycarbonyl)-3-formyl-7-azaindole (Int-16, 9.8 g, 40 mmol) and sodium borohydride (1.7 g, 44 mmol) in methanol (50 mL) were stirred at rt for 4 h. TLC showed the reaction was complete. Water was added and the mixture was extracted with ethyl acetate. The combined organic phases were washed with water, brine, dried, concentrated, and purified by flash column chromatography to afford alcohol Int-17 (8.4 g, 85%).

A mixture of 1-(tert-butyloxycarbonyl)-3-(hydroxymethyl)-7-azaindole (Int-17, 8.4 g, 34 mmol), triphenylphosphine (9.9 g, 37 mmol), dry CCl$_4$ (50 mL) in dry DMF (35 mL) were stirred at room temperature for 48 h. Solvents were removed and the residue was purified by flash column chromatography to give chloride Int-14 (3.45 g, 38%).

$^1$H NMR (400 MHz, CDCl$_3$) δ 8.55 (d, J=4.4 Hz, 1H), 8.01 (d, J=7.2 Hz, 1H), 7.69 (s, 1H), 7.27-7.24 (m, 1H), 4.76 (s, 2H), 1.67 (s, 9H).

Example 1

1-(2-Methoxyl-5-chlorophenyl)-3-[1-(1H-pyrrolo[2,3-b]pyridin-4-ylmethyl)-2,3-dihydro-1H-indol-4-yl] urea hydrochloride A round-bottom flask was charged with 4-nitroindole (4.8 g, 30 mmol), Palladium on carbon (10%, 480 mg), and THF (50 mL), and the mixture was stirred under one hydrogen atmosphere overnight. TLC showed the reaction was complete. The catalyst was filtered off and the filtrate was concentrated to afford 4-amino-1H-indole, which was used directly in the next step without purification.

A solution of 5-chloro-2-methoxyphenyl isocyanate (Int-4, 5.5 g, 30 mmol) in DCM (20 mL) was added dropwise to the 4-amino-1H-indole in DCM (30 mL) from Step A, and the resulting mixture was stirred overnight, then filtered to give the crude product 1-(5-chloro-2-methoxyphenyl)-3-(1H-indol-4-yl)urea (6.6 g, 70%), which was used directly in the next step without purification.

To a mixture of 1-(5-chloro-2-methoxyphenyl)-3-(1H-indol-4-yl)urea (6.3 g, 20 mmol) in acetic acid (50 mL) was added portionwise NaBH$_3$CN (1.9 g, 30 mmol), and the resulting mixture was stirred at rt for 1 h. The solvent was evaporated and residue was diluted with water, neutralized with NaHCO$_3$ and extracted with EtOAc. The combined organic phase were washed with brine, dried and evaporated to give crude 1-(5-chloro-2-methoxyphenyl)-3-(2,3-dihydro-1H-indol-4-yl)urea (6.3 g, 100%), which was used directly in the next step without purification.

$^1$H NMR (300 MHz, DMSO-d$_6$) δ 8.72 (s, 1H), 8.65 (s, 1H), 8.22 (d, J=1.8 Hz, 1H), 7.14 (d, J=6.3 Hz, 1H), 7.03-6.94 (m, 2H), 6.83 (t, J=6.0 Hz, 1H), 6.20 (d, J=5.7 Hz, 1H), 5.47 (s, 1H), 3.88 (s, 3H), 3.44-3.40 (m, 2H), 2.86 (t, J=6.3 Hz, 2H).

To a mixture of 1-(5-chloro-2-methoxyphenyl)-3-(2,3-dihydro-1H-indol-4-yl)urea (2.2 g, 7 mmol), potassium carbonate (1.16 g, 8.4 mmol), and DMF (30 mL) was added portionwise 1-(t-butyloxycarbonyl)-4-chloromethyl-7-azaindole (Int-11, 2.2 g, 8.4 mmol), and the mixture was stirred at 80° C. until the reaction complete (by TLC). Water was then added, the mixture was extracted with EtOAc. The combined organic phases were washed with brine, dried over anhydrous sodium sulfate, filtered, concentrated under reduced pressure, and purified by flash column chromatography to provide the product (1.9 g, 50%).

$^1$H NMR (400 MHz, CDCl$_3$) δ 8.49 (d, J=4.8 Hz, 1H), 8.29 (d, J=2.4 Hz, 1H), 7.65 (d, J=4.0 Hz, 1H), 7.43 (s, 1H), 7.22 (d, J=5.2 Hz, 1H), 7.12 (t, J=8.0 Hz, 2H), 6.91 (dd, J=8.8, 2.4 Hz, 1H), 6.86 (d, J=8.4 Hz, 1H), 6.74 (d, J=8.8 Hz, 1H), 6.64 (d, J=4.0 Hz, 1H), 6.36 (d, J=8.0 Hz, 1H), 6.32 (s, 1H), 4.51 (s, 2H), 3.78 (s, 3H), 3.40 (t, J=8.4 Hz, 2H), 2.98 (t, J=8.0 Hz, 2H), 1.67 (s, 9H).

1-(2-Methoxyl-5-chlorophenyl)-3-{1-[1-(t-butyloxycarbonyl)-1H-pyrrolo[2,3-b]pyridin-4-ylmethyl]-2,3-dihydro-1H-indol-4-yl}urea (500 mg, 0.92 mmol) was added to a 25% HCl in methanol solution. The resulting reaction mixture was stirred at rt overnight, then concentrated to afford the product 1-(2-methoxyl-5-chlorophenyl)-3-[1-(1H-pyrrolo[2,3-b]pyridin-4-ylmethyl)-2,3-dihydro-1H-indol-4-yl]urea hydrochloride (412 mg, 93%).

$^1$H NMR (400 MHz, DMSO-d$_6$): δ 12.67 (s, 1H), 8.77 (s, 1H), 8.71 (s, 1H), 8.39 (d, J=6.0 Hz, 1H), 8.22 (d, J=2.4 Hz, 1H), 7.70 (t, J=2.4 Hz, 1H), 7.42 (d, J=6.0 Hz, 1H), 7.23 (d, J=8.0 Hz, 1H), 7.03-6.90 (m, 4H), 6.26 (d, J=8.0 Hz, 1H), 4.72 (s, 2H), 3.88 (s, 3H), 3.42 (t, J=8.4 Hz, 2H), 2.95 (t, J=8.4 Hz, 2H). MS (ESI$^+$): m/z 448.4 (100) [M+H, $^{35}$Cl]$^+$, 450.3 (33) [M+H, $^{37}$Cl]$^+$.

Example 2a 1-(2-Methoxyl-5-chlorophenyl)-3-[1-(1H-pyrrolo[2,3-b]pyridin-4-ylmethyl)-1H-indol-4-yl]urea hydrochloride To a solution of 1-(2-methoxyl-5-chlorophenyl)-3-{1-[1-(t-butyloxycarbonyl)-1H-pyrrolo[2,3-b]pyridin-4-ylmethyl]-2,3-dihydro-1H-indol-4-yl}urea (1.64 g, 3 mmol) (from Example 1) in acetone (20 mL) was added portionwise DDQ (6 mmol), and the mixture was stirred at rt overnight. The solvent was evaporated and residue was purified by flash column chromatography to provide the product (1.05 g, 64%).

$^1$H NMR (400 MHz, CDCl$_3$): δ 8.49 (d, J=5.2 Hz, 1H), 8.33 (s, 1H), 7.65 (s, 1H), 7.56 (s, 1H), 7.50 (d, J=8.0 Hz, 1H), 7.31 (t, J=6.8 Hz, 2H), 7.26-7.25 (m, 1H), 7.14 (s, 1H), 7.09 (t, J=6.0 Hz, 1H), 6.91 (d, J=8.8 Hz, 1H), 6.71-6.68 (m, 2H), 6.57 (s, 1H), 5.41 (s, 2H), 3.64 (s, 3H), 1.67 (s, 9H).

1-(2-Methoxyl-5-chlorophenyl)-3-{1-[1-(t-butyloxycarbonyl)-1H-pyrrolo[2,3-b]pyridin-4-ylmethyl]-1H-indol-4-yl}urea (500 mg, 0.92 mmol) was added to 25% HCl in methanol solution. The mixture was stirred overnight, then concentrated to afford the product 1-(2-Methoxyl-5-chlorophenyl)-3-[1-(1H-pyrrolo[2,3-b]pyridin-4-ylmethyl)-1H-indol-4-yl]urea hydrochloride (400 mg, 90%).

$^1$H NMR (400 MHz, DMSO-d$_6$): δ 12.08 (s, 1H), 9.23 (s, 1H), 8.79 (s, 1H), 8.28 (d, J=2.8 Hz, 1H), 8.19 (d, J=5.2 Hz, 1H), 7.70 (dd, J=6.0, 2.0 Hz, 1H), 7.54 (s, 1H), 7.50 (d, J=3.2 Hz, 1H), 7.05-6.96 (m, 4H), 6.79 (d, J=3.2 Hz, 1H), 6.73 (d, J=5.6 Hz, 1H), 6.47 (t, J=2.0 Hz, 1H), 5.80 (s, 2H), 3.91 (s, 3H). MS (ESI$^+$): m/z 446.2 (100) [M+H, $^{35}$Cl]$^+$, 448.3 (33) [M+H, $^{37}$Cl]$^+$.

Example 2b 1-(2-Methoxyl-5-chlorophenyl)-3-[1-(1H-pyrrolo[2,3-b]pyridin-4-ylmethyl)-1H-indol-4-yl]urea hydrochloride The title compound was also prepared according to the following method. Specifically, sodium hydride (144 mg, 6 mmol) was added to a solution of 4-nitroindole (973 mg, 6 mmol) in THF and the resulting mixture was stirred for 4 h. 1-(t-butyloxycarbonyl)-4-chloromethyl-7-azaindole (Int-11, 1.5 g, 5.5 mmol) was then added. After the reaction was complete (by TLC), the mixture was quenched with saturated aqueous ammonium chloride. The organic layer was separated and the aqueous layer was extracted with ethyl acetate. The combined organic layers were washed with brine, dried over anhydrous sodium sulfate, filtered, concentrated under reduced pressure, and purified by flash column chromatography to provide 4-[(4-nitro-1H-indol-1-yl)methyl]-1H-pyrrolo[2,3-b]pyridine (254 mg, 16%).

$^1$H NMR (400 MHz, CDCl$_3$): δ 10.00 (brs, 1H), 8.26 (d, J=4.8, 1H), 8.20 (d, J=8.0, 1H), 7.59 (d, J=8.0 Hz, 1H), 7.51 (d, J=1.2, 1H), 7.41 (d, J=1.6, 1H), 7.40 (d, J=1.6, 1H), 7.29 (t, J=8.0, 1H), 6.70 (d, J=4.0, 1H), 6.33 (d, J=1.6, 1H), 5.76 (s, 2H).

A round-bottom flask was charged with 4-[(4-nitro-1H-indol-1-yl)methyl]-1H-pyrrolo[2,3-b]pyridine (526 mg, 1.8 mmol), Boc$_2$O (786 mg, 3.6 mmol), 4-dimethylaminopyridine (cat.), and DCM (30 mL). The mixture was stirred overnight, concentrated and purified by flash column chromatography to afford product 4-[(4-nitro-1H-indol-1-yl)methyl]-1-(t-butyloxycarbonyl)-1H-pyrrolo[2,3-b]pyridine (516 mg, 73%).

$^1$H NMR (400 MHz, CDCl$_3$): δ 8.38 (d, J=4.8, 1H), 8.10 (d, J=8.4, 1H), 7.59 (d, J=4.0, 1H), 7.43 (d, J=8.0 Hz, 1H), 7.39 (d, J=3.2, 1H), 7.31 (d, J=3.2, 1H), 7.17 (t, J=8.0, 1H), 6.70 (d, J=5.2, 1H), 6.14 (d, J=4.0, 1H), 5.62 (s, 2H), 1.61 (s, 9H).

In a round-bottom flask was added 4-[(4-nitro-1H-indol-1-yl)methyl]-1-(t-butyloxycarbonyl)-1H-pyrrolo[2,3-b]pyridine (500 mg, 1.3 mmol), Palladium on carbon (50 mg, 10%), and THF (30 mL). The mixture was stirred under a hydrogen atmosphere for 2 h, then filtered, concentrated to afford 4-[(4-amino-1H-indol-1-yl)methyl]-1-(t-butyloxycarbonyl)-1H-pyrrolo[2,3-b]pyridine (450 mg).

To a solution of 4-[(4-amino-1H-indol-1-yl)methyl]-1-(t-butyloxycarbonyl)-1H-pyrrolo[2,3-b]pyridine (450 mg) in DCM was added 5-chloro-2-methoxyphenyl isocyanate (Int-4, 275 mg, 1.5 mmol). The mixture was stirred overnight, then concentrated, and purified by flash column chromatography to give the desired product 1-(2-methoxyl-5-chlorophenyl)-3-{1-[1-(t-butyloxycarbonyl)-1H-pyrrolo[2, 3-1])pyridin-4-ylmethyl]-1H-indol-4-yl}urea (540 mg, 80% for two steps).

$^1$H NMR (400 MHz, CDCl$_3$): δ 8.40 (d, J=1.6, 1H), 8.34 (s, J=4.2, 1H), 7.91 (s, 1H), 7.76 (s, 1H), 7.63 (d, J=4.0, 1H), 7.46 (d, J=7.6, 1H), 7.12 (t, J=8.0, 1H), 7.03 (d, J=3.2, 1H), 6.96 (J=8.4, 1H), 6.90, 6.87 (dd, J=8.8, 2.8, 1H), 6.68-6.64 (m, 3H), 6.27 (d, J=4.4, 1H), 5.51 (s, 2H), 3.60 (s, 3H), 1.66 (s, 9H).

1-(2-Methoxyl-5-chlorophenyl)-3-{1-[1-(t-butyloxycarbonyl)-1H-pyrrolo[2,3-b]pyridin-4-ylmethyl]-1H-indol-4-yl}urea (500 mg, 0.92 mmol) was added to 25% HCl in methanol solution. The mixture was stirred overnight, then concentrated to afford the product 1-(2-Methoxyl-5-chlorophenyl)-3-[1-(1H-pyrrolo[2,3-b]pyridin-4-ylmethyl)-1H-indol-4-yl]urea hydrochloride (400 mg, 90%).

$^1$H NMR (400 MHz, DMSO-d$_6$): δ 12.08 (s, 1H), 9.23 (s, 1H), 8.79 (s, 1H), 8.28 (d, J=2.8 Hz, 1H), 8.19 (d, J=5.2 Hz, 1H), 7.70 (dd, J=6.0, 2.0 Hz, 1H), 7.54 (s, 1H), 7.50 (d, J=3.2 Hz, 1H), 7.05-6.96 (m, 4H), 6.79 (d, J=3.2 Hz, 1H), 6.73 (d, J=5.6 Hz, 1H), 6.47 (t, J=2.0 Hz, 1H), 5.80 (s, 2H), 3.91 (s, 3H).

Example 3

1-(2-Methoxyl-5-chlorophenyl)-3-[1-(1H-pyrrolo[2,3-b]pyridin-3-ylmethyl)-1H-indol-4-yl]urea hydrochloride Sodium hydride (144 mg, 6 mmol) was added to a solution of 4-nitroindole (973 mg, 6 mmol) in THF, and the resulting mixture was stirred for 4 h. 1-(t-Butyloxycarbonyl)-3-chloromethyl-7-azaindole (Int-14, 1.5 g, 5.5 mmol) was then added. Upon completion (by TLC), the reaction was quenched with saturated aqueous ammonium chloride. The organic layer was separated and the aqueous layer was extracted with ethyl acetate. The combined organic layers were washed with brine, dried over anhydrous sodium sulfate, filtered, and concentrated under reduced pressure to dryness. The residue was purified by flash column chromatography to provide 3-[(4-nitro-1H-indol-1-yl)methyl]-1H-pyrrolo[2,3-b]pyridine (547 mg, 34%).

¹H NMR (400 MHz, CDCl₃): δ 9.54 (brs, 1H), 8.34 (brs, 1H), 8.16 (d, J=7.6, 1H), 7.76 (d, J=8.4 Hz, 1H), 7.65 (d, J=8.4, 1H), 7.41 (d, J=3.6, 1H), 7.31 (s, 1H), 7.29 (d, J=9.6, 2H), 7.08 (t, J=6.4, 1H), 5.57 (s, 2H).

A round-bottom flask was charged with 3-[(4-nitro-1H-indol-1-yl)methyl]-1H-pyrrolo[2,3-b]pyridine (526 mg, 1.8 mmol), Boc₂O (786 mg, 3.6 mmol), 4-dimethylaminopyridine (cat.), triethylamine (5.4 mmol) and DCM (30 mL). The mixture was stirred overnight, concentrated, and purified by flash column chromatography to afford product 3-[(4-nitro-1H-indol-1-yl)methyl]-1-(t-butyloxycarbonyl)-1H-pyrrolo[2,3-b]pyridine (516 mg, 73%).

¹H NMR (400 MHz, CDCl₃): δ 8.51 (d, J=4.0, 1H), 8.17 (d, J=8.0, 1H), 7.74 (d, J=8.4 Hz, 1H), 7.63 (s, 1H), 7.45 (d, J=6.8, 1H), 7.39 (d, J=2.8, 1H), 7.32-7.29 (m, 2H), 7.10 (dd, J=6.8, 2.8, 1H), 5.49 (s, 2H), 1.67 (s, 9H).

A round-bottom flask was charged with 3-[(4-nitro-1H-indol-1-yl)methyl]-1-(t-butyloxycarbonyl)-1H-pyrrolo[2,3-b]pyridine (510 mg, 1.3 mmol), Pd/C (50 mg, 10%) and THF (30 mL). The mixture was then stirred under a hydrogen atmosphere for 2 h, filtered, and concentrated under reduced pressure to afford 3-[(4-amino-1H-indol-1-yl)methyl]-1-(t-butyloxycarbonyl)-1H-pyrrolo[2,3-b]pyridine (470 mg).

A solution of 3-[(4-amino-1H-indol-1-yl)methyl]-1-(t-butyloxycarbonyl)-1H-pyrrolo[2,3-b]pyridine from previous step and 5-chloro-2-methoxyphenyl isocyanate (Int-14, 275 mg, 1.5 mmol) in toluene was stirred overnight. The reaction mixture was concentrated and purified by flash column chromatography to afford product 1-(2-methoxyl-5-chlorophenyl)-3-{1-[1-(t-butyloxycarbonyl)-1H-pyrrolo[2,3-b]pyridin-3-ylmethyl]-1H-indol-4-yl}urea (518 mg, 73% for two steps).

¹H NMR (400 MHz, CDCl₃): δ 8.49 (d, J=5.2, 1H), 8.33 (s, 1H), 7.65 (s, 1H), 7.56 (s, 1H), 7.50 (d, J=8.0, 1H), 7.31 (t, J=6.8, 2H), 7.26-7.25 (m, 1H), 7.14 (s, 1H), 7.09 (t, J=6.0, 1H), 6.91 (d, J=8.8, 1H), 6.71-6.68 (m, 2H), 6.57 (s, 1H), 5.41 (s, 2H), 3.64 (s, 3H), 1.67 (s, 9H).

To 1-(2-methoxyl-5-chlorophenyl)-3-{1-[1-(t-butyloxycarbonyl)-1H-pyrrolo[2,3-b]pyridin-3-ylmethyl]-1H-indol-4-yl}urea (500 mg, 0.92 mmol) was added hydrogen chloride methanol solution (25%), and the resulting mixture was stirred overnight, then concentrated to give the product 1-(2-Methoxyl-5-chlorophenyl)-3-[1-(1H-pyrrolo[2,3-b]pyridin-3-ylmethyl)-1H-indol-4-yl]urea hydrochloride (412 mg, 93%).

MS (ESI⁺): m/z 446.4 (100) [M+H, ³⁵Cl]⁺, 448.3 (33) [M+H, ³⁷Cl]⁺.

General Procedure 1:

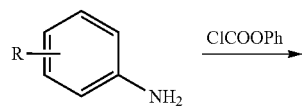

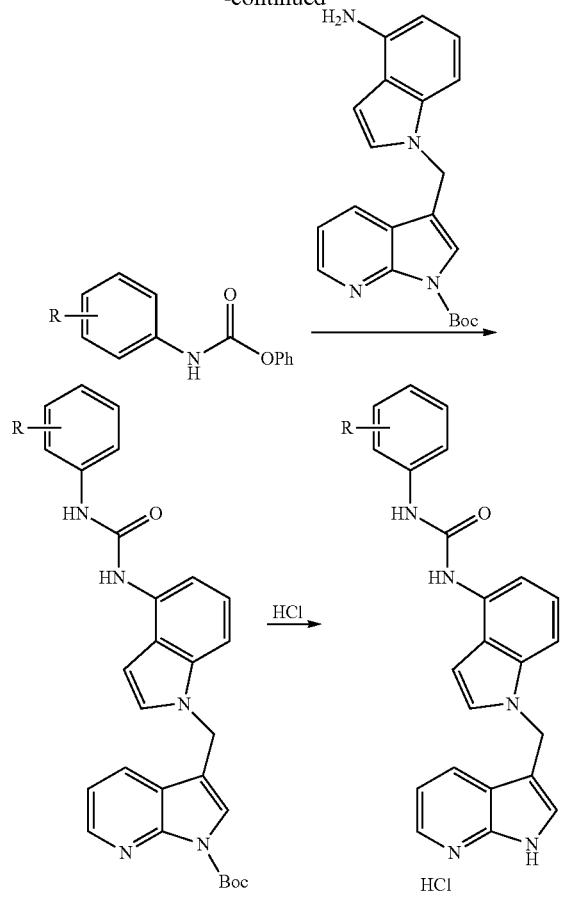

Under General Procedure 1, phenyl chloroformate (1 mmol) was added to a solution of arylamine (1 mmol) and NaHCO₃ (1 mmol) in DCM. After the reaction was completed (by TLC), the reaction mixture was concentrated under reduced pressure to dryness to provide phenyl arylcarbamate, which was used directly in the next step without purification.

A mixture of phenyl arylcarbamate, Et₃N (3 mmol), and 3-[(4-amino-1H-indol-1-yl)methyl]-1-(t-butyloxycarbonyl)-1H-pyrrolo[2,3-b]pyridine (1 mmol) in MeCN (30 mL) was stirred at 80° C. until the reaction was complete (by TLC). The reaction mixture was concentrated under reduced pressure, and residue was purified by flash column chromatography to give the urea product.

The following Preparations and Examples were synthesized according to General Procedure 1 or the procedures for preparing Example 3:

Example 4

1-Phenyl-3-[1-(1H-pyrrolo[2,3-b]pyridin-3-ylmethyl)-1H-indol-4-yl]urea hydrochloride MS (ESI⁺): m/z 382.7 [M+H]⁺

Example 4A

1-Phenyl-3-{1-[1-(t-butyloxycarbonyl)-1H-pyrrolo[2,3-b]pyridin-3-ylmethyl]-1H-indol-4-yl}urea ¹H NMR (400 MHz, CDCl₃) δ 8.38 (dd, J=4.8, 1.6 Hz, 1H), 8.22 (s, 1H), 7.78 (s, 1H), 7.65 (s, 1H), 7.56-7.53 (m, 2H), 7.42 (dd, J=8.0, 1.2 Hz, 1H), 7.34 (d, J=2.0 Hz, 1H), 7.24 (s, 1H), 7.15-7.14 (m, 2H), 7.04 (t, J=8.0 Hz, 1H), 6.99 (dd, J=8.0, 4.8 Hz, 1H), 6.89-6.87 (m, 1H), 6.79 (d, J=3.2 Hz, 1H), 6.09 (d, J=2.8 Hz, 1H), 5.27 (s, 2H), 1.63 (s, 9H).

Example 5

1-(2-Fluorophenyl)-3-[1-(1H-pyrrolo[2,3-b]pyridin-3-ylmethyl)-1H-indol-4-yl]urea hydrochloride MS (ESI$^+$): m/z 400.7 [M+H]$^+$

Example 6

1-(3-Fluorophenyl)-3-[1-(1H-pyrrolo[2,3-b]pyridin-3-ylmethyl)-1H-indol-4-yl]urea hydrochloride MS (ESI$^+$): m/z 400.7 [M+H]$^+$

Example 7

1-(4-Fluorophenyl)-3-[1-(1H-pyrrolo[2,3-b]pyridin-3-ylmethyl)-1H-indol-4-yl]urea hydrochloride MS (ESI$^+$): m/z 400.7 [M+H]$^+$

Example 8

1-(2-Chlorophenyl)-3-[1-(1H-pyrrolo[2,3-b]pyridin-3-ylmethyl)-1H-indol-4-yl]urea hydrochloride MS (ESI$^+$): m/z 416.7 (100) [M+H, $^{35}$Cl]$^+$, 418.6 (33) [M+H, $^{37}$Cl]$^+$

Example 8A 1-(2-Chlorophenyl)-3-{1-[1-(t-butyloxycarbonyl)-1H-pyrrolo[2,3-b]pyridin-3-ylmethyl]-1H-indol-4-yl}urea $^1$H NMR (400 MHz, CDCl$_3$) δ 8.41 (d, J=5.2 Hz, 1H), 8.25 (d, J=8.4 Hz, 1H), 7.56 (s, 1H), 7.48 (s, 1H), 7.38 (dd, J=8.4, 1.2 Hz, 1H), 7.30 (d, J=7.6 Hz, 1H), 7.25 (d, J=8.4 Hz, 1H), 7.20-7.14 (m, 3H), 7.06-6.98 (m, 3H), 6.86 (t, J=8.0 Hz, 1H), 6.50 (d, J=2.8 Hz, 1H), 5.34 (s, 2H), 1.59 (s, 9H).

Example 9

1-(3-Chlorophenyl)-3-[1-(1H-pyrrolo[2,3-b]pyridin-3-ylmethyl)-1H-indol-4-yl]urea hydrochloride MS (ESI$^+$): m/z 416.7 (100) [M+H, $^{35}$Cl]$^+$, 418.6 (33) [M+H, $^{37}$Cl]$^+$

Example 10

1-(4-Chlorophenyl)-3-[1-(1H-pyrrolo[2,3-b]pyridin-3-ylmethyl)-1H-indol-4-yl]urea hydrochloride MS (ESI$^+$): m/z 416.7 (100) [M+H, $^{35}$Cl]$^+$, 418.7 (33) [M+H, $^{37}$Cl]$^+$

Example 11

1-(2-Bromophenyl)-3-[1-(1H-pyrrolo[2,3-b]pyridin-3-ylmethyl)-1H-indol-4-yl]urea hydrochloride MS (ESI$^+$): m/z 460.6 (98) [M+H, $^{79}$Br]$^+$, 462.6 (100) [M+H, $^{81}$Br]$^+$

Example 12

1-(3-Bromophenyl)-3-[1-(1H-pyrrolo[2,3-b]pyridin-3-ylmethyl)-1H-indol-4-yl]urea hydrochloride MS (ESI$^+$): m/z 460.6 (98) [M+H, $^{79}$Br]$^+$, 462.6 (100) [M+H, $^{81}$Br]$^+$

Example 12A 1-(3-Bromophenyl)-3-{1-[1-(t-butyloxycarbonyl)-1H-pyrrolo[2,3-b]pyridin-3-ylmethyl]-1H-indol-4-yl}urea $^1$H NMR (400 MHz, CDCl$_3$) δ 8.44 (d, J=4.8 Hz, 1H), 7.67 (s, 1H), 7.60 (s, 1H), 7.51 (s, 1H), 7.48 (dd, J=8.0, 1.2 Hz, 1H), 7.40-7.34 (m, 2H), 7.29-7.21 (m, 2H), 7.14-7.04 (m, 4H), 6.99 (d, J=3.2 Hz, 1H), 6.34 (d, J=2.0 Hz, 1H), 5.38 (s, 2H), 1.67 (s, 9H).

Example 13

1-(4-Bromophenyl)-3-[1-(1H-pyrrolo[2,3-b]pyridin-3-ylmethyl)-1H-indol-4-yl]urea hydrochloride MS (ESI$^+$): m/z 460.6 (98) [M+H, $^{79}$Br]$^+$, 462.6 (100) [M+H, $^{81}$Br]$^+$

Example 14

1-(2-Methylphenyl)-3-[1-(1H-pyrrolo[2,3-b]pyridin-3-ylmethyl)-1H-indol-4-yl]urea hydrochloride $^1$H NMR (400 MHz, DMSO-d$_6$) δ 11.51 (s, 1H), 8.71 (s, 1H), 8.11-8.10 (m, 2H), 7.79-7.76 (m, 2H), 7.59 (d, J=7.6 Hz, 1H), 7.55 (d, J=2.4 Hz, 1H), 7.43 (d, J=3.2 Hz, 1H), 7.24 (d, J=8.4 Hz, 1H), 7.11-7.07 (m, 3H), 6.99-6.86 (m, 3H), 6.53 (d, J=2.8 Hz, 1H), 5.43 (s, 2H), 2.20 (s, 3H). MS (ESI$^+$): m/z 396.5 [M+H]$^+$

Example 15

1-(3-Methylphenyl)-3-[1-(1H-pyrrolo[2,3-b]pyridin-3-ylmethyl)-1H-indol-4-yl]urea hydrochloride MS (ESI$^+$): m/z 396.7 [M+H]$^+$

Example 16

1-(4-Methylphenyl)-3-[1-(1H-pyrrolo[2,3-b]pyridin-3-ylmethyl)-1H-indol-4-yl]urea hydrochloride MS (ESI$^+$): m/z 396.7 [M+H]$^+$

Example 17

1-(2-Methoxyphenyl)-3-[1-(1H-pyrrolo[2,3-b]pyridin-3-ylmethyl)-1H-indol-4-yl]urea hydrochloride MS (ESI$^+$): m/z 412.7 [M+H]$^+$

Example 18

1-(3-Methoxyphenyl)-3-[1-(1H-pyrrolo[2,3-b]pyridin-3-ylmethyl)-1H-indol-4-yl]urea hydrochloride MS (ESI$^+$): m/z 412.7 [M+H]$^+$

Example 18A 1-(3-Methoxyphenyl)-3-{1-[1-(t-butyloxycarbonyl)-1H-pyrrolo[2,3-b]pyridin-3-ylmethyl]-1H-indol-4-yl}urea $^1$H NMR (400 MHz, CDCl$_3$) δ 8.43 (d, J=4.8 Hz, 1H), 8.34 (s, 1H), 8.08 (s, 1H), 7.77 (d, J=8.0 Hz, 1H), 7.59 (s, 1H), 7.44 (dd, J=7.6, 1.6 Hz, 1H), 7.29 (t, J=1.6 Hz, 1H), 7.16 (t, J=8.0 Hz, 1H), 7.13-7.09 (m, 2H), 7.03 (dd, J=8.0, 4.8 Hz, 1H), 6.99 (d, J=3.6 Hz, 1H), 6.85 (dd, J=8.0, 0.8 Hz, 1H), 6.54 (d, J=3.2 Hz, 1H), 6.50 (dd, J=4.8 Hz, 1H), 5.33 (s, 2H), 3.75 (s, 3H), 1.62 (s, 9H).

Example 19

1-(4-Methoxyphenyl)-3-[1-(1H-pyrrolo[2,3-b]pyridin-3-ylmethyl)-1H-indol-4-yl]urea hydrochloride MS (ESI$^+$): m/z 412.7 [M+H]$^+$

Example 20

1-(2-Trifluoromethoxyphenyl)-3-[1-(1H-pyrrolo[2,3-b]pyridin-3-ylmethyl)-1H-indol-4-yl]urea hydrochloride MS (ESI$^+$): m/z 466.3 [M+H]$^+$

Example 21

1-(3-Trifluoromethoxyphenyl)-3-[1-(1H-pyrrolo[2,3-b]pyridin-3-ylmethyl)-1H-indol-4-yl]urea hydrochloride MS (ESI$^+$): m/z 466.3 [M+H]$^+$

Example 22

1-(4-Trifluoromethoxyphenyl)-3-[1-(1H-pyrrolo[2,3-b]pyridin-3-ylmethyl)-1H-indol-4-yl]urea hydrochloride MS (ESI$^+$): m/z 466.3 [M+H]$^+$

Example 22A 1-(4-Trifluoromethoxyphenyl)-3-{1-[1-(t-butyloxycarbonyl)-1H-pyrrolo[2,3-b]pyridin-3-ylmethyl]-1H-indol-4-yl}urea $^1$H NMR (400 MHz, CDCl$_3$) δ 8.42 (dd, J=4.8, 1.2 Hz, 1H), 8.05 (s, 1H), 7.89 (s, 1H), 7.65 (s, 1H), 7.49-7.44 (m, 2H), 7.36 (s, 1H), 7.34 (s, 1H), 7.22-7.16 (m, 2H), 7.04-7.01 (m, 3H), 6.89 (d, J=3.2 Hz, 1H), 6.21 (d, J=3.6 Hz, 1H), 5.31 (s, 2H), 1.64 (s, 9H).

Example 23

1-(2-Trifluoromethylphenyl)-3-[1-(1H-pyrrolo[2,3-b]pyridin-3-ylmethyl)-1H-indol-4-yl]urea hydrochloride MS (ESI$^+$): m/z 450.4 [M+H]$^+$

Example 24

1-(3-Trifluoromethylphenyl)-3-[1-(1H-pyrrolo[2,3-b]pyridin-3-ylmethyl)-1H-indol-4-yl]urea hydrochloride MS (ESI$^+$): m/z 450.4 [M+H]$^+$

Example 25

1-(4-Trifluoromethylphenyl)-3-[1-(1H-pyrrolo[2,3-b]pyridin-3-ylmethyl)-1H-indol-4-yl]urea hydrochloride MS (ESI$^+$): m/z 450.4 [M+H]$^+$

Example 26

1-(3-Cyanophenyl)-3-[1-(1H-pyrrolo[2,3-b]pyridin-3-ylmethyl)-1H-indol-4-yl]urea hydrochloride MS (ESI$^+$): m/z 407.7 [M+H]$^+$

Example 27

1-(4-Cyanophenyl)-3-[1-(1H-pyrrolo[2,3-b]pyridin-3-ylmethyl)-1H-indol-4-yl]urea hydrochloride MS (ESI$^+$): m/z 407.7 [M+H]$^+$

Example 28

1-(2-Fluoro-4-chlorophenyl)-3-[1-(1H-pyrrolo[2,3-b]pyridin-3-ylmethyl)-1H-indol-4-yl]urea hydrochloride MS (ESI$^+$): m/z 434.4 (100) [M+H, $^{35}$Cl]$^+$, 436.4 (33) [M+H, $^{37}$Cl]$^+$

Example 29

1-(2-Fluoro-5-chlorophenyl)-3-[1-(1H-pyrrolo[2,3-b]pyridin-3-ylmethyl)-1H-indol-4-yl]urea hydrochloride MS (ESI$^+$): m/z 434.4 (100) [M+H, $^{35}$Cl]$^+$, 436.4 (33) [M+H, $^{37}$Cl]$^+$

Example 30

1-(2-Fluoro-5-bromophenyl)-3-[1-(1H-pyrrolo[2,3-b]pyridin-3-ylmethyl)-1H-indol-4-yl]urea hydrochloride MS (ESI$^+$): m/z 478.3 (98) [M+H, $^{79}$Br]$^+$, 480.3 (100) [M+H, $^{81}$Br]$^+$

Example 31

1-(2-Fluoro-5-methoxyphenyl)-3-[1-(1H-pyrrolo[2,3-b]pyridin-3-ylmethyl)-1H-indol-4-yl]urea hydrochloride MS (ESI$^+$): m/z 430.5 [M+H]$^+$

Example 31A 1-(2-Fluoro-5-methoxyphenyl)-3-[1-(1H-pyrrolo[2,3-b]pyridin-3-ylmethyl)-1H-indol-4-yl]urea $^1$H NMR (400 MHz, DMSO-d$_6$): δ 11.67 (s, 1H), 8.92-8.91 (m, 2H), 8.16 (dd, J=4.4, 1.2 Hz, 1H), 7.89-7.85 (m, 2H), 7.69 (d, J=7.2 Hz, 1H), 7.64 (d, J=1.8 Hz, 1H), 7.52 (d, J=3.2 Hz, 1H), 7.34 (d, J=8.0 Hz, 1H), 7.15 (dd, J=11.2, 9.2 Hz, 1H), 7.05 (t, J=8.0 Hz, 1H), 6.99 (dd, J=8.0, 4.8 Hz, 1H), 6.56 (d, J=3.2 Hz, 1H), 6.51 (td, J=9.2, 3.6 Hz, 1H), 5.50 (s, 2H), 3.78 (s, 3H), 3.71 (s, 3H).

Example 32

1-(2,5-Dimethoxyphenyl)-3-[1-(1H-pyrrolo[2,3-b]pyridin-3-ylmethyl)-1H-indol-4-yl]urea hydrochloride MS (ESI$^+$): m/z 442.5 [M+H]$^+$

Example 32A 1-(2,5-Dimethoxyphenyl)-3-{1-[1-(t-butyloxycarbonyl)-1H-pyrrolo[2,3-b]pyridin-3-ylmethyl]-1H-indol-4-yl}urea $^1$H NMR (400 MHz, CDCl$_3$): δ 8.48 (dd, J=8.4, 1.2 Hz, 1H), 7.96 (d, J=3.2 Hz, 1H), 7.64 (s, 1H), 7.57 (s, 1H), 7.47 (dd, J=8.0, 1.6 Hz, 1H), 7.37 (d, J=7.2 Hz, 1H), 7.30-7.24 (m, 2H), 7.12 (d, J=3.2 Hz, 1H), 7.08 (dd, J=8.0, 4.4 Hz, 1H), 6.80 (s, 1H), 6.72 (d, J=8.8 Hz, 1H), 6.55 (d, J=3.6 Hz, 1H), 6.50 (dd, J=8.8, 3.6 Hz, 1H), 5.40 (s, 2H), 3.78 (s, 3H), 3.61 (s, 3H), 1.67 (s, 9H).

General Procedure 2:

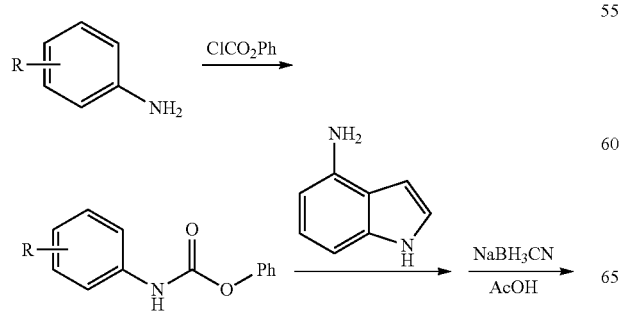

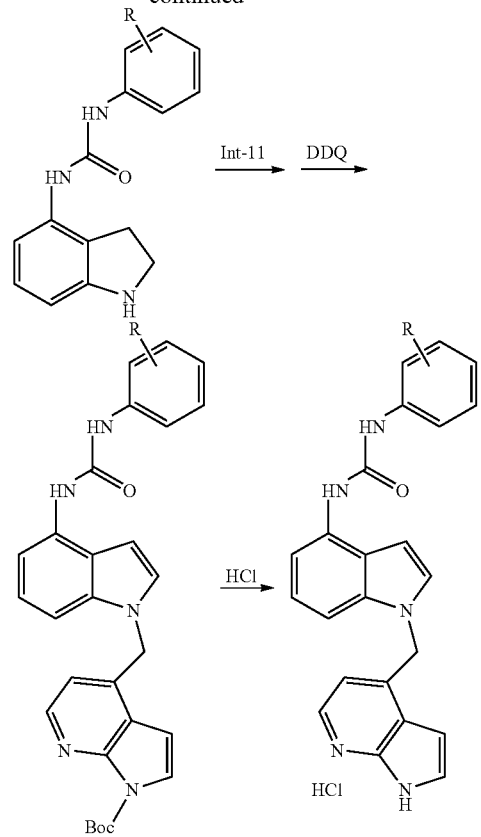

Under General Procedure 2, phenyl chloroformate (1 mmol) was added to a solution of arylamine (1 mmol) and NaHCO$_3$ (1 mmol) in DCM. After the reaction was completed (by TLC), the reaction mixture was concentrated under reduced pressure to dryness to provide phenyl arylcarbamate, which was used directly in the next step without purification.

A mixture of phenyl arylcarbamate, Et$_3$N (3 mmol), and 4-amino-1H-indole (1 mmol) in MeCN (30 mL) was stirred at 80° C. until the reaction was complete (by TLC). The reaction mixture was concentrated under reduced pressure, and residue was purified by flash column chromatography to give 1-aryl-3-(1H-indol-4-yl)urea, which was reduced into indolinyl intermediate. Alkylation with Int-11 followed by oxidation with DDQ and removal of Boc to afford the final product by following the procedures for preparing Examples 1 and 2.

The following compounds were synthesized according to General Procedure 2 and Examples 1 and 2.

Example 33

1-Phenyl-3-[1-(1H-pyrrolo[2,3-b]pyridin-4-ylmethyl)-1H-indol-4-yl]urea hydrochloride MS (ESI$^+$): m/z 382.7 [M+H]$^+$

Example 34

1-(2-Fluorophenyl)-3-[1-(1H-pyrrolo[2,3-b]pyridin-4-ylmethyl)-1H-indol-4-yl]urea hydrochloride MS (ESI$^+$): m/z 400.7 [M+H]$^+$

Example 35

1-(3-Fluorophenyl)-3-[1-(1H-pyrrolo[2,3-b]pyridin-4-ylmethyl)-1H-indol-4-yl]urea hydrochloride MS (ESI$^+$): m/z 400.7 [M+H]$^+$

Example 35A 1-(3-Fluorophenyl)-3-{1-[1-(t-butyloxycarbonyl)-1H-pyrrolo[2,3-b]pyridin-4-ylmethyl]-2,3-dihydro-1H-indol-4-yl}urea $^1$H NMR (400 MHz, CDCl$_3$) δ 8.45 (d, J=4.8 Hz, 1H), 8.29 (d, J=4.8 Hz, 1H), 7.64 (d, J=4.4 Hz, 1H), 7.38 (d, J=3.6 Hz, 1H), 7.22-7.18 (m, 2H), 7.14 (d, J=4.8 Hz, 1H), 7.10 (t, J=8.0 Hz, 1H), 7.05 (d, J=8.4 Hz, 1H), 6.74 (d, J=9.6 Hz, 1H), 6.62-6.61 (m, 2H), 6.34 (d, J=8.4 Hz, 1H), 4.48 (s, 2H), 3.31 (t, J=8.0 Hz, 2H), 2.84 (t, J=8.0 Hz, 2H), 1.67 (s, 9H).

Example 36

1-(4-Fluorophenyl)-3-[1-(1H-pyrrolo[2,3-b]pyridin-4-ylmethyl)-1H-indol-4-yl]urea hydrochloride MS (ESI$^+$): m/z 400.7 [M+H]$^+$

Example 37

1-(2-Chlorophenyl)-3-[1-(1H-pyrrolo[2,3-b]pyridin-4-ylmethyl)-1H-indol-4-yl]urea hydrochloride MS (ESI$^+$): m/z 416.7 (100) [M+H, $^{35}$Cl]$^+$, 418.6 (33) [M+H, $^{37}$Cl]$^+$

Example 38

1-(3-Chlorophenyl)-3-[1-(1H-pyrrolo[2,3-b]pyridin-4-ylmethyl)-1H-indol-4-yl]urea hydrochloride MS (ESI$^+$): m/z 416.7 (100) [M+H, $^{35}$Cl]$^+$, 418.5 (33) [M+H, $^{37}$Cl]$^+$

Example 39

1-(4-Chlorophenyl)-3-[1-(1H-pyrrolo[2,3-b]pyridin-4-ylmethyl)-1H-indol-4-yl]urea hydrochloride MS (ESI$^+$): m/z 416.7 (100) [M+H, $^{35}$Cl]$^1$, 418.6 (33) [M+H, $^{37}$Cl]$^+$

Example 40

1-(2-Bromophenyl)-3-[1-(1H-pyrrolo[2,3-b]pyridin-4-ylmethyl)-1H-indol-4-yl]urea hydrochloride MS (ESI$^+$): m/z 460.6 (98) [M+H, $^{79}$Br]$^+$, 462.7 (100) [M+H, $^{81}$Br]$^1$

Example 41

1-(3-Bromophenyl)-3-[1-(1H-pyrrolo[2,3-b]pyridin-4-ylmethyl)-1H-indol-4-yl]urea hydrochloride MS (ESI$^+$): m/z 460.6 (98) [M+H, $^{79}$Br]$^+$, 462.7 (100) [M+H, $^{81}$Br]$^+$

Example 42

1-(4-Bromophenyl)-3-[1-(1H-pyrrolo[2,3-b]pyridin-4-ylmethyl)-1H-indol-4-yl]urea hydrochloride MS (ESI$^+$): m/z 460.6 (98) [M+H, $^{79}$Br]$^+$, 462.6 (100) [M+H, $^{81}$Br]$^+$

Example 42A 1-(4-Bromophenyl)-3-{1-[1-(t-butyloxycarbonyl)-1H-pyrrolo[2,3-b]pyridin-4-ylmethyl]-1H-indol-4-yl}urea $^1$H NMR (400 MHz, CDCl$_3$): δ 8.61 (s, 1H), 8.19 (s, 1H), 8.05 (d, J=5.2 Hz, 1H), 7.49 (d, J=8.0 Hz, 1H), 7.34 (d, J=4.4 Hz, 1H), 7.16 (s, 1H), 7.07-7.05 (m, 3H), 6.88 (d, J=2.8 Hz, 1H), 6.76 (t, J=8.0 Hz, 1H), 6.54 (d, J=8.4 Hz, 1H), 6.51 (d, J=5.2 Hz, 1H), 6.47 (d, J=2.8 Hz, 1H), 6.04 (d, J=4.0 Hz, 1H), 5.36 (s, 2H), 1.35 (s, 9H).

Example 43

1-(2-Methylphenyl)-3-[1-(1H-pyrrolo[2,3-b]pyridin-4-ylmethyl)-1H-indol-4-yl]urea hydrochloride MS (ESI$^+$): m/z 396.5 [M+H]$^+$

Example 44

1-(3-Methylphenyl)-3-[1-(1H-pyrrolo[2,3-b]pyridin-4-ylmethyl)-1H-indol-4-yl]urea hydrochloride MS (ESI$^+$): m/z 396.7 [M+H]$^+$

Example 45

1-(4-Methylphenyl)-3-[1-(1H-pyrrolo[2,3-b]pyridin-4-ylmethyl)-1H-indol-4-yl]urea hydrochloride MS (ESI$^+$): m/z 396.7 [M+H]$^+$

Example 46

1-(2-Methoxyphenyl)-3-[1-(1H-pyrrolo[2,3-b]pyridin-4-ylmethyl)-1H-indol-4-yl]urea hydrochloride MS (ESI$^+$): m/z 412.7 [M+H]$^+$

Example 47

1-(3-Methoxyphenyl)-3-[1-(1H-pyrrolo[2,3-b]pyridin-4-ylmethyl)-1H-indol-4-yl]urea hydrochloride MS (ESI$^+$): m/z 412.7 [M+H]$^+$

Example 48

1-(2-Trifluoromethoxyphenyl)-3-[1-(1H-pyrrolo[2,3-b]pyridin-4-ylmethyl)-1H-indol-4-yl]urea hydrochloride MS (ESI$^+$): m/z 466.5 [M+H]$^+$

Example 49

1-(4-Trifluoromethoxyphenyl)-3-[1-(1H-pyrrolo[2,3-b]pyridin-4-ylmethyl)-1H-indol-4-yl]urea hydrochloride MS (ESI$^+$): m/z 466.5 [M+H]$^+$

Example 49A 1-(4-Trifluoromethoxyphenyl)-3-{1-[1-(t-butyloxycarbonyl)-1H-pyrrolo[2,3-b]pyridin-4-ylmethyl]-2,3-dihydro-1H-indol-4-yl}urea $^1$H NMR (400 MHz, CDCl$_3$): δ 8.39 (d, J=4.8 Hz, 1H), 8.00 (s, 1H), 7.62 (d, J=4.0 Hz, 1H), 7.44 (s, 1H), 7.42 (s, 1H), 7.16 (d, J=4.8 Hz, 1H), 7.10-7.06 (m, 4H), 6.99 (s, 1H), 6.60 (d, J=4.4 Hz, 1H), 6.30 (t, J=4.4 Hz, 1H), 4.41 (s, 2H), 3.12 (t, J=8.0 Hz, 2H), 2.53 (t, J=8.0 Hz, 2H), 1.65 (s, 9H).

Example 50

1-(2-Trifluoromethylphenyl)-3-[1-(1H-pyrrolo[2,3-b]pyridin-4-ylmethyl)-1H-indol-4-yl]urea hydrochloride MS (ESI$^+$): m/z 450.4 [M+H]$^+$

Example 51

1-(3-Trifluoromethylphenyl)-3-[1-(1H-pyrrolo[2,3-b]pyridin-4-ylmethyl)-1H-indol-4-yl]urea hydrochloride MS (ESI$^+$): m/z 450.4 [M+H]$^+$

Example 52

1-(4-Trifluoromethylphenyl)-3-[1-(1H-pyrrolo[2,3-b]pyridin-4-ylmethyl)-1H-indol-4-yl]urea hydrochloride MS (ESI$^+$): m/z 450.4 [M+H]$^+$

Example 52A 1-(4-Trifluoromethylphenyl)-3-{1-[1-(t-butyloxycarbonyl)-1H-pyrrolo[2,3-b]pyridin-4-ylmethyl]-1H-indol-4-yl}urea $^1$H NMR (400 MHz, CDCl$_3$): δ 8.37 (d, J=4.8 Hz, 1H), 7.62 (d, J=4.0 Hz, 1H), 7.55 (s, 1H), 7.50 (s, 4H), 7.35 (d, J=7.6 Hz, 1H), 7.18-7.14 (m, 2H), 7.08-7.04 (m, 2H), 6.74 (d, J=5.6 Hz, 1H), 6.48 (d, J=3.2 Hz, 1H), 6.24 (d, J=4.4 Hz, 1H), 5.56 (s, 2H), 1.65 (s, 9H).

Example 53

1-(3-Cyanophenyl)-3-[1-(1H-pyrrolo[2,3-b]pyridin-4-ylmethyl)-1H-indol-4-yl]urea hydrochloride MS (ESI$^+$): m/z 407.7 [M+H]$^+$

Example 53A 1-(3-Cyanophenyl)-3-{1-[1-(t-butyloxycarbonyl)-1H-pyrrolo[2,3-b]pyridin-4-ylmethyl]-2,3-dihydro-1H-indol-4-yl}urea $^1$H NMR (400 MHz, CDCl$_3$): δ 8.42 (d, J=5.2 Hz, 1H), 8.02 (bs, 1H), 7.83 (s, 1H), 7.78 (d, J=8.8 Hz, 1H), 7.65 (d, J=4.4 Hz, 1H), 7.38 (t, J=8.0 Hz, 1H), 7.31 (d, J=8.0 Hz, 1H), 7.19 (d, J=4.8 Hz, 1H), 7.16-7.09 (m, 2H), 6.63 (s, 1H), 6.62 (d, J=4.0 Hz, 1H), 6.39 (d, J=7.6 Hz, 1H), 4.46 (s, 2H), 3.09 (t, J=8.0 Hz, 2H), 2.37 (t, J=8.0 Hz, 2H), 1.66 (s, 9H).

Example 54

1-(4-Cyanophenyl)-3-[1-(1H-pyrrolo[2,3-b]pyridin-4-ylmethyl)-1H-indol-4-yl]urea hydrochloride MS (ESI$^+$): m/z 407.7 [M+H]$^+$

Example 55

1-(2-Fluoro-4-chlorophenyl)-3-[1-(1H-pyrrolo[2,3-b]pyridin-4-ylmethyl)-1H-indol-4-yl]urea hydrochloride MS (ESI$^+$): m/z 434.4 (100) [M+H, $^{35}$Cl]$^+$, 436.4 (33) [M+H, $^{37}$Cl]$^+$

Example 56

1-(2-Fluoro-5-chlorophenyl)-3-[1-(1H-pyrrolo[2,3-b]pyridin-4-ylmethyl)-1H-indol-4-yl]urea hydrochloride MS (ESI$^+$): m/z 434.4 (100) [M+H, $^{35}$Cl]$^+$, 436.4 (33) [M+H, $^{37}$Cl]$^+$

Example 57

1-(2-Fluoro-5-bromophenyl)-3-[1-(1H-pyrrolo[2,3-b]pyridin-4-ylmethyl)-1H-indol-4-yl]urea hydrochloride MS (ESI$^+$): m/z 478.3 (98) [M+H, $^{79}$Br]$^+$, 480.3 (100) [M+H, $^{81}$Br]$^+$

Example 57A 1-(2-Fluoro-5-bromophenyl)-3-{1-[1-(t-butyloxycarbonyl)-1H-pyrrolo[2,3-b]pyridin-4-ylmethyl]-2,3-dihydro-1H-indol-4-yl}urea $^1$H NMR (400 MHz, CDCl$_3$): δ 8.48-8.45 (m, 2H), 7.65 (d, J=4.4 Hz, 1H), 7.24 (d, J=2.8 Hz, 1H), 7.20 (d, J=4.8 Hz, 1H), 7.12 (t, J=8.0 Hz, 1H), 7.08 (td, J=4.4, 2.8 Hz, 1H), 6.92 (d, J=4.8 Hz, 1H), 6.89 (d, J=8.8 Hz, 1H), 6.63 (d, J=4.4 Hz, 1H), 6.57 (s, 1H), 6.37 (d, J=7.6 Hz, 1H), 4.50 (s, 2H), 3.35 (t, J=8.0 Hz, 2H), 2.89 (t, J=8.4 Hz, 2H), 1.67 (s, 9H).

Example 58

1-(2-Bromo-5-methylphenyl)-3-[1-(1H-pyrrolo[2,3-b]pyridin-4-ylmethyl)-1H-indol-4-yl]urea hydrochloride MS (ESI$^+$): m/z 474.3 (98) [M+H, $^{79}$Br]$^+$, 476.3 (100) [M+H, $^{81}$Br]$^+$

Example 58A 1-(2-Bromo-5-methylphenyl)-3-{1-[1-(t-butyloxy-carbonyl)-1H-pyrrolo[2,3-b]pyridin-4-ylmethyl]-2,3-dihydro-1H-indol-4-yl}urea $^1$H NMR (400 MHz, CDCl$_3$): δ 8.47 (d, J=5.6 Hz, 1H), 8.08 (s, 1H), 7.64 (d, J=3.2 Hz, 1H), 7.34 (d, J=8.4 Hz, 1H), 7.20-7.18 (m, 2H), 7.13 (t, J=8.0 Hz, 1H), 6.81 (d, J=8.0 Hz, 1H), 6.73 (d, J=8.4 Hz, 1H), 6.62 (d, J=4.4 Hz, 1H), 6.39 (d, J=8.0 Hz, 1H), 6.26 (s, 1H), 4.50 (s, 2H), 3.41 (t, J=8.0 Hz, 2H), 3.00 (t, J=8.4 Hz, 2H), 2.32 (s, 3H), 1.67 (s, 9H).

Example 59

1-(2-Methyl-3-fluorophenyl)-3-[1-(1H-pyrrolo[2,3-b]pyridin-4-ylmethyl)-1H-indol-4-yl]urea hydrochloride MS (ESI$^+$): m/z 414.5 [M+H]$^+$

Example 60 c-Kit, CSF-1R, and EPHA2 Biochemical Assays

A standard competition binding assay can be used to test the ability of a compound of this invention on competing with both intended and unintended kinases in vitro.

To screen a compound against a large number of human kinases, a competition binding assay with an active-site dependent binding technology was performed by KINOMEscan service (Ambit Biosciences, San Diego, Cal., USA). Three components were combined in this assay—DNA-tagged kinase, immobilized ligand, and the test compound. The ability of the test compound to compete with the immobilized ligand was measured by quantitative PCR of the DNA of the DNA tag.

A number of the compounds of this invention were screened at the concentration of 100 nM by this binding assay, and the results were reported as "% Ctrl," and the lower number indicates stronger "hit" in this matrix. Low number results for Examples 44 and 56 are summarized in the following table:

| Compound | c-Kit | CSF-1R | EPHA2 |
|---|---|---|---|
| Example 56 | 3.8 | 3.4 | 12 |
| Example 44 | 0.35 | 0.8 | 6 |

Example 61

PDGFRβ Cell-Based Assays

A standard cell-based assay for PDGFRβ kinase activity can be used to test a compound of this invention and to identify PDGFRβ antagonists.

Specifically, a compound to be tested was first dissolved in DMSO to a concentration of 10 mM and stored at −20° C. The activity of PDGFRβ in cells depends on the phosphorylation level of its intracellular domain induced by the ligand. In order to express PDGFRβ in the cell, full length PDGFRβ sequence was cloned into PC-DNA3.1 vector. The plasmid was then transfected into CHO cells. After 48 hours following the transfection, the expression of PDGFRβ in transfected CHO cells was confirmed by regular western blotting.

To screen the compound of this invention, the ELISA kit (R&D Systems, Minneapolis, Minn., USA) was used. One day before the screening, CHO cells transfected with full length PDGFRβ plasmid were grown in DMEM medium without the presence of serum. On the day of screening, various concentrations of compounds (from 0.5 nM to 500 nM) were added into DMEM medium. Two hours later, 20% of FBS (Fetal Bovine Serum) was added into the medium to stimulate the expression of phosphor-PDGFRβ. Cell lysate from approximately 5×10$^5$ transfected CHO cells were reacted with anti-phosphor-PDGFRβ or anti-total PDGFRβ antibody in 96 well plates, in the presence of detection antibody, the phosphor-PDGFRβ or total PDGFRβ were detected with Streptavidin-HRP (R&D Systems), followed by chemi-luminescent detection.

The compounds thus tested generally showed potent inhibitory effect on growth-factor induced or constitutively activated PDGFRβ phosphorylation. Some of these compounds were found to exhibit an IC$_{50}$ of 100 nM or less, and some other compounds exhibited an even lower IC$_{50}$, such as 10 nM or less. As such, the compounds of this invention may be used in the treatment of diseases implicated by angiogenesis.

The percentage of PDGFRβ kinase activity that remained in the presence of a compound at the concentration of 100 nM is listed in the following table for each tested compound, wherein A indicates that the percentage of kinase activity remains is below 70% and B indicates that the percentage is greater or equal to 70%.

| Compound | % PDGFRβ kinase activity remains |
|---|---|
| Example 2a/2b | A |
| Example 3 | B |
| Example 4 | B |
| Example 5 | A |
| Example 6 | A |
| Example 7 | A |
| Example 8 | A |
| Example 9 | A |
| Example 10 | B |
| Example 11 | A |
| Example 12 | B |
| Example 13 | B |
| Example 14 | A |
| Example 15 | A |
| Example 16 | A |
| Example 17 | A |
| Example 18 | A |
| Example 19 | A |
| Example 20 | A |
| Example 21 | B |
| Example 22 | B |
| Example 23 | A |
| Example 24 | A |
| Example 25 | A |
| Example 26 | A |
| Example 27 | A |
| Example 28 | B |
| Example 29 | B |
| Example 30 | B |
| Example 31 | B |
| Example 32 | B |
| Example 33 | A |
| Example 34 | A |
| Example 35 | B |
| Example 36 | B |
| Example 37 | A |

-continued

| Compound | % PDGFRβ kinase activity remains |
|---|---|
| Example 38 | A |
| Example 39 | A |
| Example 40 | A |
| Example 42 | A |
| Example 44 | A |
| Example 45 | A |
| Example 47 | B |
| Example 49 | A |
| Example 50 | B |
| Example 51 | B |
| Example 52 | B |
| Example 53 | B |
| Example 54 | B |
| Example 55 | B |
| Example 58 | A |
| Example 59 | A |

Example 62

VEGFR2 Cell-Based Assays

A standard cell-based assay for VEGFR2 kinase activity can be used to test compounds of this invention and to identify VEGFR2 antagonists.

Specifically, a compound to be tested was first dissolved in DMSO to a concentration of 10 mM and stored at −20° C. The activity of VEGFR2 in cells depends on the phosphorylation level at its intracellular domain induced by the ligand. In order to express VEGFR2 in the cells, full length VEGFR2 sequence was cloned into PC-DNA3.1 vector, the plasmid was then transfected into CHO cells. After 48 hours, the expression of VEGFR2 in transfected CHO cells was confirmed by regular western blotting.

To screen the compounds of this invention, the ELISA kit (R&D Systems) was used. One day before the screening, CHO cells transfected with full length VEGFR2 plasmid were grown in DMEM medium without the presence of serum. On the day of screening, various concentrations of compounds (From 0.5 nM to 500 nM) were added into DMEM medium. Two hours later, 20% of FBS (Fetal Bovine Serum) was added into the medium to stimulate the production of phosphor-VEGFR2. Cell lysate from approximately 5×10$^5$ transfected CHO cells were reacted with anti-phosphor-VEGFR2 or anti-total VEGFR2 antibody in 96 well plates. In the presence of detection antibody, the phosphor-VEGFR2 or total VEGFR2 were detected with Streptavidin-HRP (R&D Systems) followed by chemiluminescence detection.

The compounds thus tested generally showed potent inhibitory effect on growth factor-induced or constitutively activated VEGFR2 phosphorylation. Some of these compounds were found to exhibit an IC$_{50}$ of 100 nM or less, and some other compounds exhibited an even lower IC$_{50}$, such as 10 nM or less. As such, the compounds of this invention may be used in the treatment of diseases implicated by angiogenesis.

The percentage of VEGFR2 kinase activity that remained in the presence of a compound at the concentration of 100 nM is listed in the following table for each tested compound, wherein A indicates that the percentage of kinase activity remains is below 70% and B indicates that the percentage is greater or equal to 70%.

| Compound | % VEGFR2 kinase activity remains |
|---|---|
| Example 1 | A |
| Example 2a/2b | A |
| Example 3 | A |
| Example 4 | B |
| Example 5 | B |
| Example 6 | A |
| Example 7 | A |
| Example 8 | B |
| Example 9 | A |
| Example 10 | B |
| Example 11 | B |
| Example 12 | A |
| Example 13 | B |
| Example 14 | A |
| Example 15 | A |
| Example 16 | B |
| Example 17 | A |
| Example 18 | A |
| Example 19 | A |
| Example 20 | A |
| Example 21 | B |
| Example 22 | B |
| Example 23 | A |
| Example 24 | A |
| Example 25 | B |
| Example 26 | B |
| Example 27 | A |
| Example 28 | A |
| Example 29 | A |
| Example 30 | A |
| Example 32 | A |
| Example 33 | A |
| Example 34 | A |
| Example 35 | A |
| Example 36 | A |
| Example 37 | A |
| Example 38 | A |
| Example 39 | A |
| Example 40 | A |
| Example 41 | B |
| Example 42 | A |
| Example 44 | A |
| Example 45 | A |
| Example 46 | B |
| Example 47 | B |
| Example 51 | A |
| Example 52 | A |
| Example 54 | B |
| Example 55 | A |
| Example 56 | B |
| Example 57 | A |
| Example 58 | A |
| Example 59 | A |

Example 63

C-Met Cell-Based Assay

A procedure for standard cell-based assay for c-Met kinase activity can be used to test compounds of this invention for their inhibitory effect on this kinase and to identify c-Met antagonists.

Specifically, a compound to be tested was first dissolved in DMSO to a concentration of 10 mM and stored at −20° C. The activity of c-Met in cells depends on the phosphorylation level at its intracellular domain induced by its ligand, Hepatocyte growth factor (HGF). In order to induce the cells to produce phosphate c-Met, paracrine HGF-dependent NSCLC (None Small Cell Lung Cancer) A549 cells were grown in DMEM with 10% FBS.

To screen compounds of this invention for their inhibitory effect on c-Met kinase, the ELISA kit (R&D Systems) was used. One day before screening procedure, A549 cells were grown in DMEM without the presence of serum. On the day of screening procedure, various concentrations of compounds (from 0.5 nM to 500 nM) were added into the culture medium. Two hours later, 20% of FBS (Fetal Bovine Serum) was added into the medium to stimulate the expression of phosphor-c-Met. After 20 minutes, cell lysate from approximately $5 \times 10^5$ A549 cells were reacted with anti-phosphor-c-Met or anti total c-Met antibody in 96 well plates. In the presence of detection antibody, the phosphor-c-Met or total c-Met can be detected with Streptavidin-HRP (R&D Systems) followed by chemiluminescence detection.

The compounds thus tested generally exhibited potent inhibitory effect on growth factor-induced or constitutively activated c-Met phosphorylation. Some of these compounds exhibited an $IC_{50}$ of 100 nM or less, and some others were even more effective with an $IC_{50}$ of 10 nM or less. Such a kinase inhibitory activity is valuable in the treatment of diseases associated with angiogenesis, invasive growth, epithelial-to-mesenchymal transition (EMT), and cell migration such as cancers.

The percentage of c-Met kinase activity remains in the presence of a compound at the concentration of 100 nM is listed in the following table for each tested compounds, wherein A indicates that the percentage of kinase activity remains is below 70% and B indicates that the percentage is greater or equal to 70%.

| Compound | % c-Met kinase activity remains |
|---|---|
| Example 1 | A |
| Example 2a/2b | A |
| Example 3 | A |
| Example 4 | B |
| Example 5 | A |
| Example 6 | B |
| Example 7 | A |
| Example 8 | A |
| Example 9 | B |
| Example 10 | B |
| Example 11 | A |
| Example 12 | A |
| Example 13 | A |
| Example 14 | A |
| Example 15 | A |
| Example 16 | A |
| Example 17 | A |
| Example 18 | A |
| Example 19 | A |
| Example 20 | A |
| Example 21 | B |
| Example 22 | A |
| Example 23 | A |
| Example 24 | A |
| Example 25 | A |
| Example 26 | A |
| Example 27 | A |
| Example 28 | A |
| Example 29 | B |
| Example 30 | B |
| Example 32 | A |
| Example 33 | B |
| Example 34 | B |
| Example 35 | A |
| Example 36 | A |
| Example 37 | A |
| Example 38 | A |
| Example 39 | A |
| Example 40 | A |
| Example 41 | B |
| Example 42 | B |
| Example 44 | A |
| Example 45 | A |
| Example 46 | B |
| Example 47 | A |
| Example 51 | B |
| Example 52 | B |
| Example 54 | B |
| Example 55 | B |
| Example 56 | A |
| Example 57 | A |
| Example 58 | A |
| Example 59 | A |

Some other compounds of the present invention possess good inhibitory activity against both VEGFR2 and c-Met, or VEGFR2, PDGFRβ and c-Met, or VEGFR2, c-Met, and c-Kit, or some other combinations of kinases from among VEGFR2, c-Met, RON, PDGFRα, PDGFRβ, c-Kit, CSF1R, EphA2, Alk, Tie-1, Tie-2, Flt3, FGFR1, FGFR2, FGFR3, FGFR4, EGFR, Her2, Abl, Aurora A, Aurora B, Aurora C, Src, Lck, IGF-1R, or IR receptor tyrosine kinases. Such multiplex inhibitory activities against several receptor tyrosine kinases, which are among targets of some drugs that have shown effectiveness in the treatment of certain clinical indications, are of extreme interests in the treatment of diseases associated with angiogenesis, invasive growth, epithelial-to-mesenchymal transition (EMT), and cell migration, including cancer, rheumatoid arthritis, arterial restenosis, autoimmune diseases, acute inflammation, acute and chronic nephropathies, diabetic retinopathy, psoriasis, and macular degeneration.

Example 64

In Vivo Testing of Anti-Tumor Efficacy

Female (nu/nu) Balb/c athymic mice at 4-6 weeks of age were injected subcutaneously (s.c.) with MDA-MB-231 human breast cancer cells, A549 human non-small cell lung cancer cells, U87-MG human glioblastoma cells, PC-3 human prostate cancer cells, HT-29 human colon cancer, BEL-7404 human hepatocellular carcinoma, or MKN-45 human gastric cancer cells (ATCC, $5 \times 10^6$ cells suspended in 100 μl DMEM medium). Treatment was initiated after the tumor mass grown from s.c. implanted tumor cells reached a median volume of 200-400 mm³. Mice were randomized into groups with three in each group for small-sample efficacy tests such that the median tumor volume is nearly equal among all groups. For large-sample efficacy tests, mice were randomized into groups with thirteen or fourteen in each group. Each group was treated either with compounds (dissolved in 2:1 mixture of PEG400 and 0.01N HCl (v/v)) or without compounds (vehicle only, 2:1 mixture of PEG400 and 0.01N HCl (v/v)) once per day at dose 12.5, 25, 50 or 100 mg/kg by oral gavage. Tumor volumes were assessed at least twice weekly by caliper measurement from the start of treatment. Tumor volume was calculated using the formula ½× L×W² (L: length of tumor's long axis, W: length of tumor's short axis). Treatment was applied for at least two weeks or until the tumor volume reaches a size of ~2500 mm³ or greater. Mice were humanly sacrificed after the experiment.

The efficacy of compounds in reducing tumor growth was assessed by the index Tumor Growth Inhibition (TGI). TGI for a given treatment period was calculated using the group mean tumor volumes according to the formula:

$$TGI = 100 \times (V_{Vehicle\_group} - V_{Treatment\_group}) \div V_{Vehicle\_group}$$

wherein $V_{Vehicle\_group}$ represents the mean tumor volume for the group treated with vehicle and $V_{Treatment\_group}$ represents the mean tumor volume of the group treated with a compound.

The TGI for the compounds of this invention in in vivo anti-tumor efficacy test is listed in the following table for each tested compound, wherein B indicates that the TGI for the compound of this invention is between 0% and 50% and A indicates that the TGI is greater or equal to 50%.

The following table summarizes the results of efficacy studies of the test compounds:

| Compound | Indication (group × sample size) | Cancer cell line | Dosage (mg/kg) | Tumor Growth Inhibition (TGI) |
|---|---|---|---|---|
| Example 1 | Breast cancer (n = 2 × 3) | MDA-MB-231 | 100 | A |
| Example 2a/2b | Breast cancer (n = 2 × 3) | MDA-MB-231 | 100 | A |
| | Gastric cancer (n = 2 × 3) | MKN-45 | 100 | A |
| | Non-small cell lung cancer (n = 2 × 3) | A549 | 100 | A |
| | Prostate cancer (n = 2 × 3) | PC-3 | 100 | A |
| | Glioblastoma (n = 2 × 3) | U87-MG | 100 | A |
| Example 3 | Breast cancer (n = 2 × 3) | MDA-MB-231 | 100 | A |
| | Lung cancer (n = 2 × 3) | HT-1299 | 100 | A |
| | Non-small cell lung cancer (n = 2 × 3) | A549 | 100 | A |
| Example 38 | Breast cancer (n = 2 × 3) | MDA-MB-231 | 100 | A |
| | Liver cancer (n = 2 × 3) | BEL7404 | 50 | A |
| Example 44 | Breast cancer (n = 2 × 3) | MDA-MB-231 | 100 | A |
| | Gastric cancer (n = 2 × 3) | MKN-45 | 100 | A |
| | Prostate cancer (n = 2 × 3) | PC-3 | 50 | A |
| | Non-small cell lung cancer (n = 2 × 3) | A549 | 50 | A |
| Example 51 | Breast cancer (n = 2 × 3) | MDA-MB-231 | 50 | A |
| | Gastric cancer (n = 2 × 3) | MKN-45 | 50 | A |
| | Prostate cancer (n = 2 × 3) | PC-3 | 50 | A |
| | Non-small cell lung cancer (n = 2 × 3) | A549 | 50 | A |
| Example 56 | Breast cancer (n = 6 × 14) | MDA-MB-231 | 12.5 | A |
| | | | 25 | A |
| | | | 50 | A |
| | | | 100 | A |
| | Gastric Cancer (n = 6 × 13) | MKN-45 | 12.5 | B |
| | | | 25 | A |
| | | | 50 | A |
| | | | 100 | A |
| | Breast cancer (n = 2 × 3) | MDA-MB-231 | 50 | A |
| | Gastric cancer (n = 3 × 3) | MKN-45 | 50 | A |
| | Prostate cancer (n = 2 × 3) | PC-3 | 50 | A |
| | Liver cancer (n = 2 × 3) | BEL-7404 | 50 | A |
| | Non-small cell lung cancer (n = 2 × 3) | A549 | 50 | A |
| | Colon cancer (n = 2 × 3) | HT-29 | 50 | A |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications referenced herein are incorporated by reference in their entireties.

What is claimed is:

1. A compound of Formula Ia, IIa, Ib, IIb, or Id, or a pharmaceutically acceptable salt thereof,

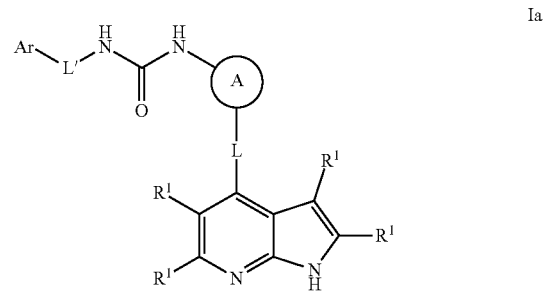

Ia

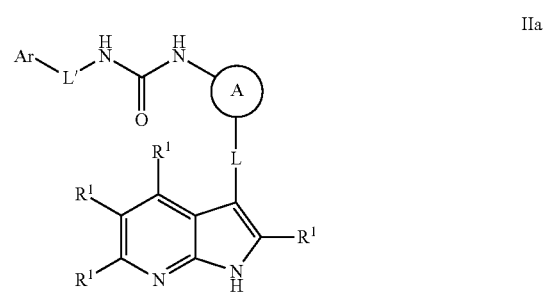

IIa

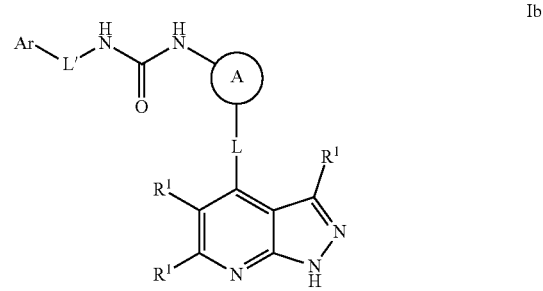

Ib

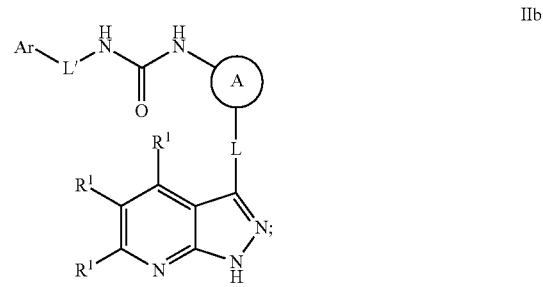

IIb

-continued

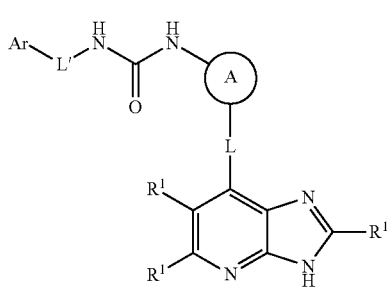

wherein:
L is O, S(O)$_n$, N—R$^2$, or alkylene which is optionally substituted with one or more independent R$^3$ groups;
R$^2$ is H, alkyl, aryl, heteroaryl, —C(=O)-alkyl, —C(=O)-aryl, or —C(=O)-heteroaryl, each of which is optionally substituted with one or more independent Q$^1$ groups;
L' is a covalent bond, —C(=O)—, —C(=O)-alkylene, or alkylene, each of which is optionally substituted with one or more independent R$^4$ groups;
A is

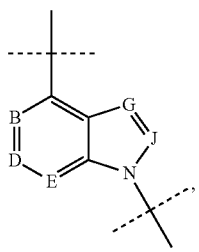

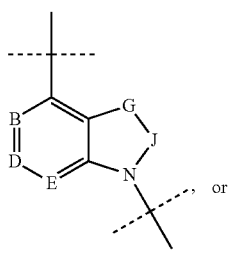

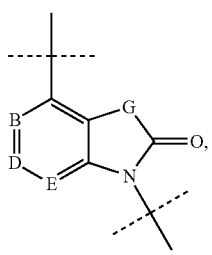

wherein B, D, E, G, and J are each independently N or C—R$^5$; the 5-membered ring of A is connected to L and the 6-membered ring of A is connected to the urea group in Formula I or II;
Ar is aryl or heteroaryl, and is optionally substituted with one or more independent R$^6$ groups;
R$^1$, R$^3$, R$^4$, R$^5$, and R$^6$ are each independently H, halo, —CN, —CF$_3$, —NO$_2$, —NH$_2$, —OH, —OCF$_3$, —OCH$_3$, —CO$_2$H, alkyl, alkenyl, alkynyl, cycloalkyl, heterocycloalkyl, arylalkyl, or heteroarylalkyl, each of which is optionally substituted with one or more independent Q$^2$ groups;
Q$^1$ and Q$^2$ are each independently H, halo, —CN, —CF$_3$, —OCF$_3$, —NO$_2$, oxo, alkyl, alkenyl, alkynyl, cycloalkyl, heterocycloalkyl, aryl, heteroaryl, heterocycloaryl, —OR$^7$, —S(O)$_n$R$^8$, —NR$^9$R$^{10}$, —SO$_2$NR$^9$R$^{10}$, —C(O)R$^{11}$, —C(O)NR$^9$R$^{10}$, —C(O)OR$^{12}$, —OC(O)R$^{13}$, —NR$^9$C(O)R$^{11}$, —NR$^9$S(O)$_2$R$^{14}$, —NR$^{15}$C(O)NR$^9$R$^{10}$, —NR$^{15}$S(O)$_2$NR$^9$R$^{10}$ or —NR$^{15}$S(O)NR$^9$R$^{10}$, each of which is optionally substituted with one or more independent H, halo, —CN, —OH, —NH$_2$, —NO$_2$, oxo, —CF$_3$, —OCF$_3$, —CO$_2$H, —S(O)$_n$H, alkyl, aryl, heteroaryl, cycloalkyl, heterocycloalkyl, heterocycloaryl, or —O-alkyl, each of which may be partially or fully halogenated;
R$^7$, R$^8$, R$^{11}$, R$^{12}$, R$^{13}$, R$^{14}$, or R$^{15}$ are each independently H, alkyl, alkenyl, alkynyl, cycloalkyl, heterocycloalkyl, aryl, heteroaryl, or heterocycloaryl;
R$^9$ and R$^{10}$ are each independently H, alkyl, alkenyl, alkynyl, cycloalkyl, heterocycloalkyl, aryl, heteroaryl, or heterocycloaryl; or when in —NR$^9$R$^{10}$, R$^9$ and R$^{10}$, together with the nitrogen atom to which they are attached, form a 3- to 12-membered saturated or unsaturated ring, wherein said ring optionally includes one or more heteroatoms each independently being O, N, or S(O)$_n$;
n is 0, 1, or 2; and
the R$^1$ groups in Formula Ia, IIa, Ib, IIb, or Id can be the same or different.

2. The compound of claim 1, wherein the compound is of Formula Ia or IIa, in which the R$^1$ groups can be the same or different

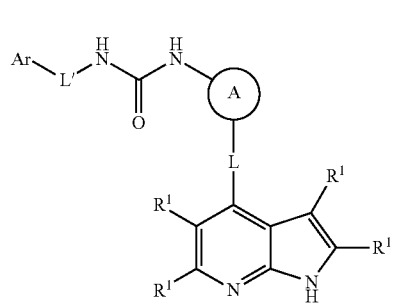

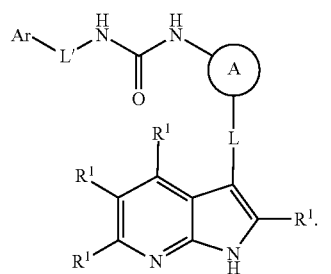

3. The compound of claim 2, wherein each R$^1$ is H, and L' is a covalent bond.

4. The compound of claim 1, wherein the compound is of Formula Ib or IIb, in which the R¹ groups can be the same or different

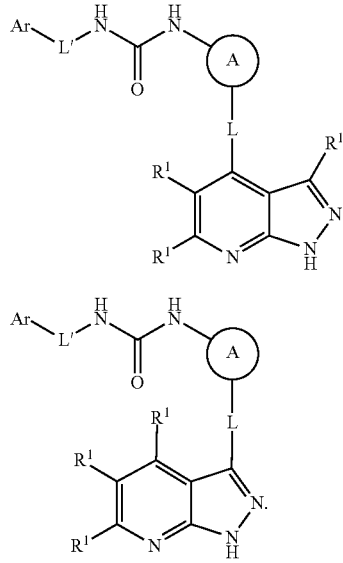

5. The compound of claim 4, wherein each R¹ is H and L' is a covalent bond.

6. The compound of claim 1, wherein the compound is of Formula Id, in which the R¹ groups can be the same or different

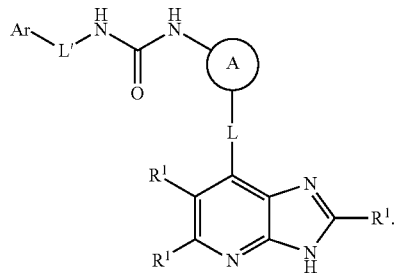

7. The compound of claim 6, wherein each R¹ is H and L' is a covalent bond.

8. The compound of claim 1, wherein L is alkylene optionally substituted with one or more independent R³ groups.

9. The compound of claim 8, wherein L is alkylene.

10. The compound of claim 9, wherein L is methylene, ethylene, propylene, or i-propylene.

11. The compound of claim 10, wherein L' is a covalent bond.

12. The compound of claim 1, wherein L' is a covalent bond.

13. The compound of claim 1, wherein Ar is phenyl, naphthyl, pyridinyl, pyridonyl, pyrimidinyl, pyridazinyl, triazinyl, imidazolyl, thiophenyl, furyl, thiazolyl, oxazolyl, triazolyl, quinolinyl, isoquinolinyl, tetrahydroquinolinyl, indolyl, azaindolyl, indazolyl, benzimidazolyl, benzofuryl, benzothiophenyl, benzotriazolyl, 2-oxindolyl, or indolinyl, each of which is optionally substituted with one or more groups each independently being halo, alkoxy, alkyl, haloalkoxy, cyano, oxo, or optionally substituted heterocycloalkyl.

14. The compound of claim 13, wherein L' is a covalent bond.

15. The compound of claim 14, wherein L is alkylene.

16. The compound of claim 15, wherein L is methylene, ethylene, propylene, or i-propylene.

17. The compound of claim 15, wherein A is A1-a, A1-b, A1-c, A1-d, A1-e, A1-f, A1-g, A1-h, A1-i, A2-a, A2-b, A3-a, A3-b, A3-c, A3-d, or A3-e, each of which is optionally substituted with one or more independent R⁵ groups

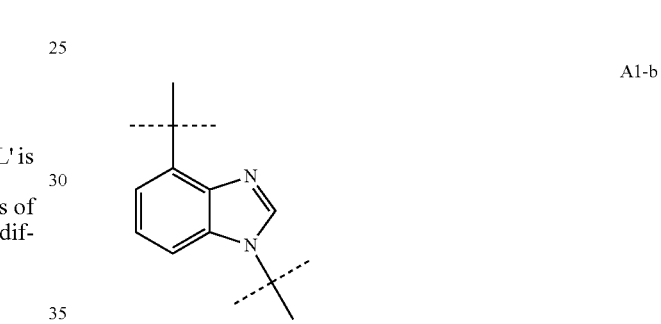

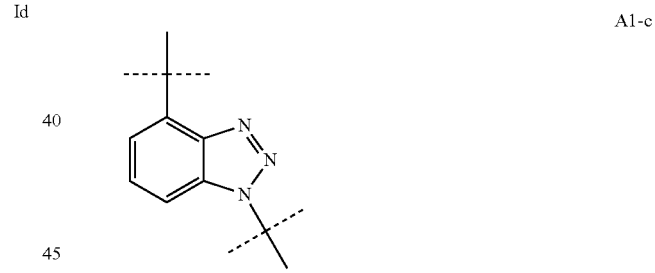

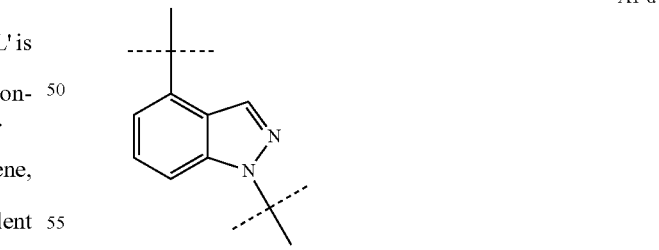

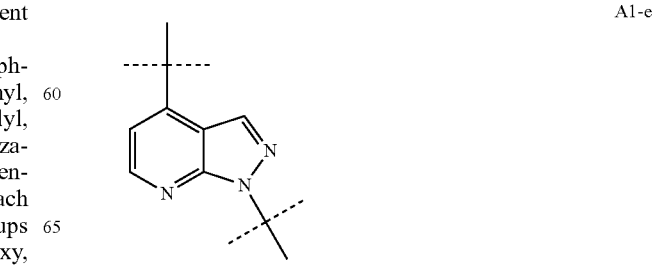

A1-f 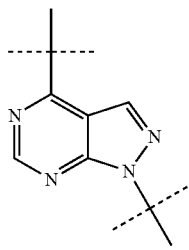

A1-g 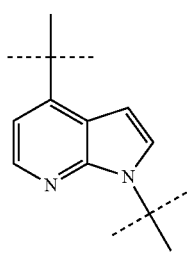

A1h 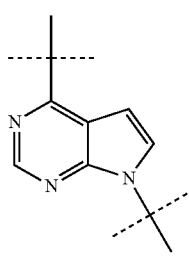

A1-i 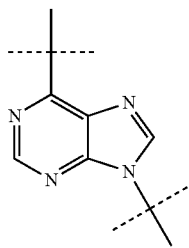

A2-a 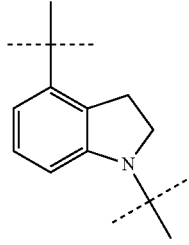

A2-b 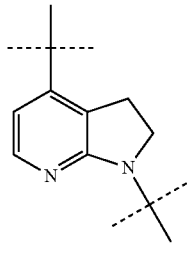

A3-a 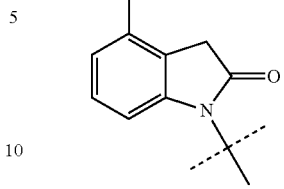

A3-b 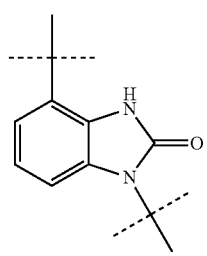

A3-c 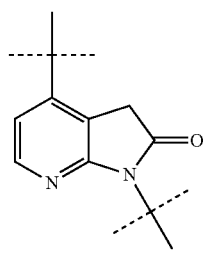

A3-d 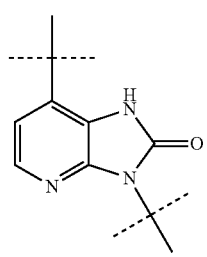

A3-e 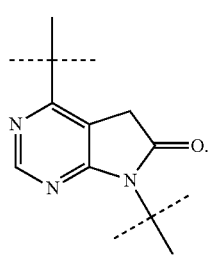

18. The compound of claim 17, wherein A is A1-a, A1-b, A1-d, A1-e, A1-g, A2-a, A2-b, A3-a, or A3-c, each of which is optionally substituted with one or more independent $R^5$ groups.

19. The compound of claim 18, wherein A is A1-a, A1-b, A1-d, A1-g, A2-a, or A2-b, each of which is optionally substituted with one or more independent $R^5$ groups.

20. The compound of claim 19, wherein A is A1-a or A2-a, each of which is optionally substituted with one or more independent $R^5$ groups.

21. The compound of claim 20, wherein A is A1-a or A2-a.

22. The compound of claim 1, wherein A is A1-a, A1-b, A1-c, A1-d, A1-e, A1-f, A1-g, A1-h, A1-i, A2-a, A2-b, A3-a, A3-b, A3-c, A3-d, or A3-e, each of which is optionally substituted with one or more independent $R^5$ groups.

23. The compound of claim 22, wherein A is A1-a, A1-b, A1-d, A1-e, A1-g, A2-a, A2-b, A3-a, or A3-c, each of which is optionally substituted with one or more independent $R^5$ groups.

24. The compound of claim 23, wherein A is A1-a, A1-b, A1-d, A1-g, A2-a, or A2-b, each of which is optionally substituted with one or more independent $R^5$ groups.

25. The compound of claim 24, wherein A is A1-a or A2-a, each of which is optionally substituted with one or more independent $R^5$ groups.

26. The compound of claim 25, wherein A is A1-a or A2-a.

27. The compound of claim 1, wherein the compound is:

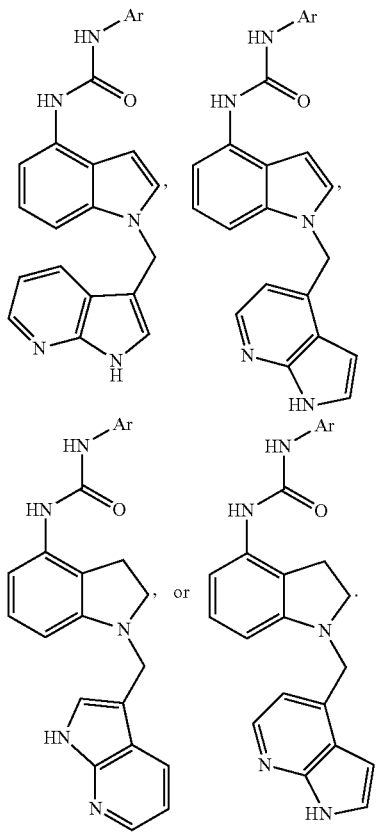

28. The compound of claim 1, wherein Ar is phenyl optionally substituted with one or two or three or four groups each independently being fluoro, bromo, chloro, cyano, methyl, trifluoromethyl, methoxy, trifluoromethoxy, or oxopyrrolidinyl; or Ar is indolinyl optionally substituted with one or two or three or four groups each independently being fluoro, bromo, chloro, cyano, methyl, trifluoromethyl, methoxy, trifluoromethoxy, or oxo.

29. The compound of claim 1, wherein the compound is:
1-Phenyl-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Fluorophenyl)-3-[1-(1H-pyrrolo[2,3-b]pyridin-3-ylmethyl)-1H-indol-4-yl]urea;
1-(4-Fluorophenyl)-3-[1-(1H-pyrrolo[2,3-b]pyridin-3-ylmethyl)-1H-indol-4-yl]urea;
1-(2-Chlorophenyl)-3-[1-(1H-pyrrolo[2,3-b]pyridin-3-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Chlorophenyl)-3-[1-(1H-pyrrolo[2,3-b]pyridin-3-ylmethyl)-1H-indol-4-yl]urea;
1-(2-Bromophenyl)-3-[1-(1H-pyrrolo[2,3-b]pyridin-3-ylmethyl)-1H-indol-4-yl]urea;
1-(3-Bromophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(2-Methylphenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(4-Methylphenyl)-3-[1-(1H-pyrrolo[2,3-b]pyridin-3-ylmethyl)-1H-indol-4-yl]urea;
1-(2-Methoxyphenyl)-3-[1-(1H-pyrrolo[2,3-b]pyridin-3-ylmethyl)-1H-indol-4-yl]urea;
1-(3-Methoxyphenyl)-3-[1-(1H-pyrrolo[2,3-b]pyridin-3-ylmethyl)-1H-indol-4-yl]urea;
1-(4-Methoxyphenyl)-3-[1-(1H-pyrrolo[2,3-b]pyridin-3-ylmethyl)-1H-indol-4-yl]urea;
1-(2-Trifluoromethoxyphenyl)-3-[1-(1H-pyrrolo[2,3-b]pyridin-3-ylmethyl)-1H-indol-4-yl]urea;
1-(3-Trifluoromethoxyphenyl)-3-[1-(1H-pyrrolo[2,3-b]pyridin-3-ylmethyl)-1H-indol-4-yl]urea;
1-(4-Trifluoromethoxyphenyl)-3-[1-(1H-pyrrolo[2,3-b]pyridin-3-ylmethyl)-1H-indol-4-yl]urea;
1-(2-Trifluoromethylphenyl)-3-[1-(1H-pyrrolo[2,3-b]pyridin-3-ylmethyl)-1H-indol-4-yl]urea;
1-(3-Trifluoromethylphenyl)-3-[1-(1H-pyrrolo[2,3-b]pyridin-3-ylmethyl)-1H-indol-4-yl]urea;
1-(4-Trifluoromethylphenyl)-3-[1-(1H-pyrrolo[2,3-b]pyridin-3-ylmethyl)-1H-indol-4-yl]urea;
1-(2-Cyanophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(4-Cyanophenyl)-3-[1-(1H-pyrrolo[2,3-b]pyridin-3-ylmethyl)-1H-indol-4-yl]urea;
1-(2-Methoxyl-5-fluorophenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea;
1-(2-Methoxyl-5-bromophenyl)-3-[1-(1H-pyrrolo[2,3-b]pyridin-3-ylmethyl)-1H-indol-4-yl]urea;
1-(2-Methoxyl-5-methylphenyl)-3-[1-(1H-pyrrolo[2,3-b]pyridin-3-ylmethyl)-1H-indol-4-yl]urea;
1-(2,5-Dimethoxyphenyl)-3-[1-(1H-pyrrolo[2,3-b]pyridin-3-ylmethyl)-1H-indol-4-yl]urea;
1-(2-Methoxyl-5-trifluomethylphenyl)-3-[1-(1H-pyrrolo[2,3-b]pyridin-3-ylmethyl)-1H-indol-4-yl]urea;
1-(2-Fluoro-5-methylphenyl)-3-[1-(1H-pyrrolo[2,3-b]pyridin-3-ylmethyl)-1H-indol-4-yl]urea;
1-(2-Fluoro-5-methoxyphenyl)-3-[1-(1H-pyrrolo[2,3-b]pyridin-3-ylmethyl)-1H-indol-4-yl]urea;
1-(2-Fluoro-5-trifluoromethylphenyl)-3-[1-(1H-pyrrolo[2,3-b]pyridin-3-ylmethyl)-1H-indol-4-yl]urea;
1-(2-Fluoro-5-chlorophenyl)-3-[1-(1H-pyrrolo[2,3-b]pyridin-3-ylmethyl)-1H-indol-4-yl]urea;
1-(2-Fluoro-5-bromophenyl)-3-[1-(1H-pyrrolo[2,3-b]pyridin-3-ylmethyl)-1H-indol-4-yl]urea;
1-(2-Trifluoromethyl-5-methylphenyl)-3-[1-(1H-pyrrolo[2,3-b]pyridin-3-ylmethyl)-1H-indol-4-yl]urea;
1-(2-oxo-2,3-dihydro-1H-indol-5-yl)-3-[1-(1H-pyrrolo[2,3-b]pyridin-3-ylmethyl)-1H-indol-4-yl]urea;

1-[4-(5-oxopyrrolidin-2-yl)phenyl]-3-[1-(1H-pyrrolo[2,3-b]pyridin-3-ylmethyl)-1H-indol-4-yl]urea;
1-Phenyl-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(4-Chlorophenyl)-3-[1-(1H-pyrrolo[2,3-b]pyridin-4-ylmethyl)-1H-indol-4-yl]urea;
1-(2-Bromophenyl)-3-[1-(1H-pyrrolo[2,3-b]pyridin-4-ylmethyl)-1H-indol-4-yl]urea;
1-(3-Bromophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-4-ylmethyl)-1H-indol-4-yl]urea;
1-(2-Methylphenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(4-Methylphenyl)-3-[1-(1H-pyrrolo[2,3-b]pyridin-4-ylmethyl)-1H-indol-4-yl]urea;
1-(2-Methoxyphenyl)-3-[1-(1H-pyrrolo[2,3-b]pyridin-4-ylmethyl)-1H-indol-4-yl]urea;
1-(3-Methoxyphenyl)-3-[1-(1H-pyrrolo[2,3-b]pyridin-4-ylmethyl)-1H-indol-4-yl]urea;
1-(4-Methoxyphenyl)-3-[1-(1H-pyrrolo[2,3-b]pyridin-4-ylmethyl)-1H-indol-4-yl]urea;
1-(2-Trifluoromethoxyphenyl)-3-[1-(1H-pyrrolo[2,3-b]pyridin-4-ylmethyl)-1H-indol-4-yl]urea;
1-(3-Trifluoromethoxyphenyl)-3-[1-(1H-pyrrolo[2,3-b]pyridin-4-ylmethyl)-1H-indol-4-yl]urea;
1-(4-Trifluoromethoxyphenyl)-3-[1-(1H-pyrrolo[2,3-b]pyridin-4-ylmethyl)-1H-indol-4-yl]urea;
1-(2-Trifluoromethylphenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Cyanophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(4-Cyanophenyl)-3-[1-(1H-pyrrolo[2,3-b]pyridin-4-ylmethyl)-1H-indol-4-yl]urea;
1-(2-Methoxyl-5-fluorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(2-Methoxyl-5-bromophenyl)-3-[1-(1H-pyrrolo[2,3-b]pyridin-4-ylmethyl)-1H-indol-4-yl]urea;
1-(2-Methoxyl-5-methylphenyl)-3-[1-(1H-pyrrolo[2,3-b]pyridin-4-ylmethyl)-1H-indol-4-yl]urea;
1-(2,5-Dimethoxyphenyl)-3-[1-(1H-pyrrolo[2,3-b]pyridin-4-ylmethyl)-1H-indol-4-yl]urea;
1-(2-Methoxyl-5-trifluomethylphenyl)-3-[1-(1H-pyrrolo[2,3-b]pyridin-4-ylmethyl)-1H-indol-4-yl]urea;
1-(2-Fluoro-5-methylphenyl)-3-[1-(1H-pyrrolo[2,3-b]pyridin-4-ylmethyl)-1H-indol-4-yl]urea;
1-(2-Fluoro-5-methoxyphenyl)-3-[1-(1H-pyrrolo[2,3-b]pyridin-4-ylmethyl)-1H-indol-4-yl]urea;
1-(2-Fluoro-5-trifluoromethylphenyl)-3-[1-(1H-pyrrolo[2,3-b]pyridin-4-ylmethyl)-1H-indol-4-yl]urea
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Trifluoromethyl-5-methylphenyl)-3-[1-(1H-pyrrolo[2,3-b]pyridin-4-ylmethyl)-1H-indol-4-yl]urea;
1-(2-oxo-2,3-dihydro-1H-indol-5-yl)-3-[1-(1H-pyrrolo[2,3-b]pyridin-4-ylmethyl)-1H-indol-4-yl]urea;
1-[4-(5-oxopyrrolidin-2-yl)phenyl]-3-[1-(1H-pyrrolo[2,3-b]pyridin-4-ylmethyl)-1H-indol-4-yl]urea;
1-Phenyl-3-[1-(1H-pyrrolo[2,3-b]pyridin-3-ylmethyl)-2,3-dihydro-1H-indol-4-yl]urea;
1-(2-Fluorophenyl)-3-[1-(1H-pyrrolo[2,3-b]pyridin-3-ylmethyl)-2,3-dihydro-1H-indol-4-yl]urea;
1-(3-Fluorophenyl)-3-[1-(1H-pyrrolo[2,3-b]pyridin-3-ylmethyl)-2,3-dihydro-1H-indol-4-yl]urea;
1-(4-Fluorophenyl)-3-[1-(1H-pyrrolo[2,3-b]pyridin-3-ylmethyl)-2,3-dihydro-1H-indol-4-yl]urea;
1-(2-Chlorophenyl)-3-[1-(1H-pyrrolo[2,3-b]pyridin-3-ylmethyl)-2,3-dihydro-1H-indol-4-yl]urea;
1-(3-Chlorophenyl)-3-[1-(1H-pyrrolo[2,3-b]pyridin-3-ylmethyl)-2,3-dihydro-1H-indol-4-yl]urea;
1-(4-Chlorophenyl)-3-[1-(1H-pyrrolo[2,3-b]pyridin-3-ylmethyl)-2,3-dihydro-1H-indol-4-yl]urea;
1-(2-Bromophenyl)-3-[1-(1H-pyrrolo[2,3-b]pyridin-3-ylmethyl)-2,3-dihydro-1H-indol-4-yl]urea;
1-(3-Bromophenyl)-3-[1-(1H-pyrrolo[2,3-b]pyridin-3-ylmethyl)-2,3-dihydro-1H-indol-4-yl]urea;
1-(4-Bromophenyl)-3-[1-(1H-pyrrolo[2,3-b]pyridin-3-ylmethyl)-2,3-dihydro-1H-indol-4-yl]urea;
1-(2-Methylphenyl)-3-[1-(1H-pyrrolo[2,3-b]pyridin-3-ylmethyl)-2,3-dihydro-1H-indol-4-yl]urea;
1-(3-Methylphenyl)-3-[1-(1H-pyrrolo[2,3-b]pyridin-3-ylmethyl)-2,3-dihydro-1H-indol-4-yl]urea;
1-(4-Methylphenyl)-3-[1-(1H-pyrrolo[2,3-b]pyridin-3-ylmethyl)-2,3-dihydro-1H-indol-4-yl]urea;
1-(2-Methoxyphenyl)-3-[1-(1H-pyrrolo[2,3-b]pyridin-3-ylmethyl)-2,3-dihydro-1H-indol-4-yl]urea;
1-(3-Methoxyphenyl)-3-[1-(1H-pyrrolo[2,3-b]pyridin-3-ylmethyl)-2,3-dihydro-1H-indol-4-yl]urea;
1-(4-Methoxyphenyl)-3-[1-(1H-pyrrolo[2,3-b]pyridin-3-ylmethyl)-2,3-dihydro-1H-indol-4-yl]urea;
1-(2-Trifluoromethoxyphenyl)-3-[1-(1H-pyrrolo[2,3-b]pyridin-3-ylmethyl)-2,3-dihydro-1H-indol-4-yl]urea;
1-(3-Trifluoromethoxyphenyl)-3-[1-(1H-pyrrolo[2,3-b]pyridin-3-ylmethyl)-2,3-dihydro-1H-indol-4-yl]urea;
1-(4-Trifluoromethoxyphenyl)-3-[1-(1H-pyrrolo[2,3-b]pyridin-3-ylmethyl)-2,3-dihydro-1H-indol-4-yl]urea;
1-(2-Trifluoromethylphenyl)-3-[1-(1H-pyrrolo[2,3-b]pyridin-3-ylmethyl)-2,3-dihydro-1H-indol-4-yl]urea;
1-(3-Trifluoromethylphenyl)-3-[1-(1H-pyrrolo[2,3-b]pyridin-3-ylmethyl)-2,3-dihydro-1H-indol-4-yl]urea;
1-(4-Trifluoromethylphenyl)-3-[1-(1H-pyrrolo[2,3-b]pyridin-3-ylmethyl)-2,3-dihydro-1H-indol-4-yl]urea;
1-(2-Cyanophenyl)-3-[1-(1H-pyrrolo[2,3-b]pyridin-3-ylmethyl)-2,3-dihydro-1H-indol-4-yl]urea;
1-(3-Cyanophenyl)-3-[1-(1H-pyrrolo[2,3-b]pyridin-3-ylmethyl)-2,3-dihydro-1H-indol-4-yl]urea;
1-(4-Cyanophenyl)-3-[1-(1H-pyrrolo[2,3-b]pyridin-3-ylmethyl)-2,3-dihydro-1H-indol-4-yl]urea;
1-(2-Methoxyl-5-fluorophenyl)-3-[1-(1H-pyrrolo[2,3-b]pyridin-3-ylmethyl)-2,3-dihydro-1H-indol-4-yl]urea;

1-(2-Methoxyl-5-chlorophenyl)-3-[1-(1H-pyrrolo[2,3-b]pyridin-3-ylmethyl)-2,3-dihydro-1H-indol-4-yl]urea;
1-(2-Methoxyl-5-bromophenyl)-3-[1-(1H-pyrrolo[2,3-b]pyridin-3-ylmethyl)-2,3-dihydro-1H-indol-4-yl]urea;
1-(2-Methoxyl-5-methylphenyl)-3-[1-(1H-pyrrolo[2,3-b]pyridin-3-ylmethyl)-2,3-dihydro-1H-indol-4-yl]urea;
1-(2,5-Dimethoxyphenyl)-3-[1-(1H-pyrrolo[2,3-b]pyridin-3-ylmethyl)-2,3-dihydro-1H-indol-4-yl]urea;
1-(2-Methoxyl-5-trifluomethylphenyl)-3-[1-(1H-pyrrolo[2,3-b]pyridin-3-ylmethyl)-2,3-dihydro-1H-indol-4-yl]urea;
1-(2-Fluoro-5-methylphenyl)-3-[1-(1H-pyrrolo[2,3-b]pyridin-3-ylmethyl)-2,3-dihydro-1H-indol-4-yl]urea;
1-(2-Fluoro-5-methoxyphenyl)-3-[1-(1H-pyrrolo[2,3-b]pyridin-3-ylmethyl)-2,3-dihydro-1H-indol-4-yl]urea;
1-(2-Fluoro-5-trifluoromethylphenyl)-3-[1-(1H-pyrrolo[2,3-b]pyridin-3-ylmethyl)-2,3-dihydro-1H-indol-4-yl]urea;
1-(2-Fluoro-5-chlorophenyl)-3-[1-(1H-pyrrolo[2,3-b]pyridin-3-ylmethyl)-2,3-dihydro-1H-indol-4-yl]urea;
1-(2-Fluoro-5-bromophenyl)-3-[1-(1H-pyrrolo[2,3-b]pyridin-3-ylmethyl)-2,3-dihydro-1H-indol-4-yl]urea;
1-(2-Trifluoromethyl-5-methylphenyl)-3-[1-(1H-pyrrolo[2,3-b]pyridin-3-ylmethyl)-2,3-dihydro-1H-indol-4-yl]urea;
1-(2-oxo-2,3-dihydro-1H-indol-5-yl)-3-[1-(1H-pyrrolo[2,3-b]pyridin-3-ylmethyl)-2,3-dihydro-1H-indol-4-yl]urea;
1-[4-(5-oxopyrrolidin-2-yl)phenyl]-3-[1-(1H-pyrrolo[2,3-b]pyridin-3-ylmethyl)-2,3-dihydro-1H-indol-4-yl]urea;
1-Phenyl-3-[1-(1H-pyrrolo[2,3-b]pyridin-4-ylmethyl)-2,3-dihydro-1H-indol-4-yl]urea;
1-(2-Fluorophenyl)-3-[1-(1H-pyrrolo[2,3-b]pyridin-4-ylmethyl)-2,3-dihydro-1H-indol-4-yl]urea;
1-(3-Fluorophenyl)-3-[1-(1H-pyrrolo[2,3-b]pyridin-4-ylmethyl)-2,3-dihydro-1H-indol-4-yl]urea;
1-(4-Fluorophenyl)-3-[1-(1H-pyrrolo[2,3-b]pyridin-4-ylmethyl)-2,3-dihydro-1H-indol-4-yl]urea;
1-(2-Chlorophenyl)-3-[1-(1H-pyrrolo[2,3-b]pyridin-4-ylmethyl)-2,3-dihydro-1H-indol-4-yl]urea;
1-(3-Chlorophenyl)-3-[1-(1H-pyrrolo[2,3-b]pyridin-4-ylmethyl)-2,3-dihydro-1H-indol-4-yl]urea;
1-(4-Chlorophenyl)-3-[1-(1H-pyrrolo[2,3-b]pyridin-4-ylmethyl)-2,3-dihydro-1H-indol-4-yl]urea;
1-(2-Bromophenyl)-3-[1-(1H-pyrrolo[2,3-b]pyridin-4-ylmethyl)-2,3-dihydro-1H-indol-4-yl]urea;
1-(3-Bromophenyl)-3-[1-(1H-pyrrolo[2,3-b]pyridin-4-ylmethyl)-2,3-dihydro-1H-indol-4-yl]urea;
1-(4-Bromophenyl)-3-[1-(1H-pyrrolo[2,3-b]pyridin-4-ylmethyl)-2,3-dihydro-1H-indol-4-yl]urea;
1-(2-Methylphenyl)-3-[1-(1H-pyrrolo[2,3-b]pyridin-4-ylmethyl)-2,3-dihydro-1H-indol-4-yl]urea;
1-(3-Methylphenyl)-3-[1-(1H-pyrrolo[2,3-b]pyridin-4-ylmethyl)-2,3-dihydro-1H-indol-4-yl]urea;
1-(4-Methylphenyl)-3-[1-(1H-pyrrolo[2,3-b]pyridin-4-ylmethyl)-2,3-dihydro-1H-indol-4-yl]urea;
1-(2-Methoxyphenyl)-3-[1-(1H-pyrrolo[2,3-b]pyridin-4-ylmethyl)-2,3-dihydro-1H-indol-4-yl]urea;
1-(3-Methoxyphenyl)-3-[1-(1H-pyrrolo[2,3-b]pyridin-4-ylmethyl)-2,3-dihydro-1H-indol-4-yl]urea;
1-(4-Methoxyphenyl)-3-[1-(1H-pyrrolo[2,3-b]pyridin-4-ylmethyl)-2,3-dihydro-1H-indol-4-yl]urea;
1-(2-Trifluoromethoxyphenyl)-3-[1-(1H-pyrrolo[2,3-b]pyridin-4-ylmethyl)-2,3-dihydro-1H-indol-4-yl]urea;
1-(3-Trifluoromethoxyphenyl)-3-[1-(1H-pyrrolo[2,3-b]pyridin-4-ylmethyl)-2,3-dihydro-1H-indol-4-yl]urea;
1-(4-Trifluoromethoxyphenyl)-3-[1-(1H-pyrrolo[2,3-b]pyridin-4-ylmethyl)-2,3-dihydro-1H-indol-4-yl]urea;
1-(2-Trifluoromethylphenyl)-3-[1-(1H-pyrrolo[2,3-b]pyridin-4-ylmethyl)-2,3-dihydro-1H-indol-4-yl]urea;
1-(3-Trifluoromethylphenyl)-3-[1-(1H-pyrrolo[2,3-b]pyridin-4-ylmethyl)-2,3-dihydro-1H-indol-4-yl]urea;
1-(4-Trifluoromethylphenyl)-3-[1-(1H-pyrrolo[2,3-b]pyridin-4-ylmethyl)-2,3-dihydro-1H-indol-4-yl]urea;
1-(2-Cyanophenyl)-3-[1-(1H-pyrrolo[2,3-b]pyridin-4-ylmethyl)-2,3-dihydro-1H-indol-4-yl]urea;
1-(3-Cyanophenyl)-3-[1-(1H-pyrrolo[2,3-b]pyridin-4-ylmethyl)-2,3-dihydro-1H-indol-4-yl]urea;
1-(4-Cyanophenyl)-3-[1-(1H-pyrrolo[2,3-b]pyridin-4-ylmethyl)-2,3-dihydro-1H-indol-4-yl]urea;
1-(2-Methoxyl-5-fluorophenyl)-3-[1-(1H-pyrrolo[2,3-b]pyridin-4-ylmethyl)-2,3-dihydro-1H-indol-4-yl]urea;
1-(2-Methoxyl-5-chlorophenyl)-3-[1-(1H-pyrrolo[2,3-b]pyridin-4-ylmethyl)-2,3-dihydro-1H-indol-4-yl]urea;
1-(2-Methoxyl-5-bromophenyl)-3-[1-(1H-pyrrolo[2,3-b]pyridin-4-ylmethyl)-2,3-dihydro-1H-indol-4-yl]urea;
1-(2-Methoxyl-5-methylphenyl)-3-[1-(1H-pyrrolo[2,3-b]pyridin-4-ylmethyl)-2,3-dihydro-1H-indol-4-yl]urea;
1-(2,5-Dimethoxyphenyl)-3-[1-(1H-pyrrolo[2,3-b]pyridin-4-ylmethyl)-2,3-dihydro-1H-indol-4-yl]urea;
1-(2-Methoxyl-5-trifluomethylphenyl)-3-[1-(1H-pyrrolo[2,3-b]pyridin-4-ylmethyl)-2,3-dihydro-1H-indol-4-yl]urea;
1-(2-Fluoro-5-methylphenyl)-3-[1-(1H-pyrrolo[2,3-b]pyridin-4-ylmethyl)-2,3-dihydro-1H-indol-4-yl]urea;
1-(2-Fluoro-5-methoxyphenyl)-3-[1-(1H-pyrrolo[2,3-b]pyridin-4-ylmethyl)-2,3-dihydro-1H-indol-4-yl]urea;
1-(2-Fluoro-5-trifluoromethylphenyl)-3-[1-(1H-pyrrolo[2,3-b]pyridin-4-ylmethyl)-2,3-dihydro-1H-indol-4-yl]urea;
1-(2-Fluoro-5-chlorophenyl)-3-[1-(1H-pyrrolo[2,3-b]pyridin-4-ylmethyl)-2,3-dihydro-1H-indol-4-yl]urea;
1-(2-Fluoro-5-bromophenyl)-3-[1-(1H-pyrrolo[2,3-b]pyridin-4-ylmethyl)-2,3-dihydro-1H-indol-4-yl]urea;
1-(2-Trifluoromethyl-5-methylphenyl)-3-[1-(1H-pyrrolo[2,3-b]pyridin-4-ylmethyl)-2,3-dihydro-1H-indol-4-yl]urea;
1-(2-oxo-2,3-dihydro-1H-indol-5-yl)-3-[1-(1H-pyrrolo[2,3-b]pyridin-4-ylmethyl)-2,3-dihydro-1H-indol-4-yl]urea;
1-[4-(5-oxopyrrolidin-2-yl)phenyl]-3-[1-(1H-pyrrolo[2,3-b]pyridin-4-ylmethyl)-2,3-dihydro-1H-indol-4-yl]urea;
1-(2-chloro-5-methylphenyl)-3-[1-(1H-pyrrolo[2,3-b]pyridin-3-ylmethyl)-1H-indol-4-yl]urea;
1-(2-bromo-5-methylphenyl)-3-[1-(1H-pyrrolo[2,3-b]pyridin-3-ylmethyl)-1H-indol-4-yl]urea;
1-(2-fluoro-4-chlorophenyl)-3-[1-(1H-pyrrolo[2,3-b]pyridin-3-ylmethyl)-1H-indol-4-yl]urea;
1-(2-fluoro-6-chlorophenyl)-3-[1-(1H-pyrrolo[2,3-b]pyridin-3-ylmethyl)-1H-indol-4-yl]urea;
1-(4-morpholinomethylphenyl)-3-[1-(1H-pyrrolo[2,3-b]pyridin-3-ylmethyl)-1H-indol-4-yl]urea;
1-(2-Methyl-3-fluorophenyl)-3-[1-(1H-pyrrolo[2,3-b]pyridin-3-ylmethyl)-1H-indol-4-yl]urea;
1-(2-Methyl-3-chlorophenyl)-3-[1-(1H-pyrrolo[2,3-b]pyridin-3-ylmethyl)-1H-indol-4-yl]urea;
1-(2-Methyl-3-bromophenyl)-3-[1-(1H-pyrrolo[2,3-b]pyridin-3-ylmethyl)-1H-indol-4-yl]urea;
1-(2-chloro-5-methylphenyl)-3-[1-(1H-pyrrolo[2,3-b]pyridin-4-ylmethyl)-1H-indol-4-yl]urea;
1-(2-bromo-5-methylphenyl)-3-[1-(1H-pyrrolo[2,3-b]pyridin-4-ylmethyl)-1H-indol-4-yl]urea;

1-(2-fluoro-6-chlorophenyl)-3-[1-(1H-pyrrolo[2,3-b]pyridin-4-ylmethyl)-1H-indol-4-yl]urea;
1-(4-morpholinomethylphenyl)-3-[1-(1H-pyrrolo[2,3-b]pyridin-4-ylmethyl)-1H-indol-4-yl]urea;
1-(2-Methyl-3-fluorophenyl)-3-[1-(1H-pyrrolo[2,3-b]pyridin-4-ylmethyl)-1H-indol-4-yl]urea;
1-(2-Methyl-3-chlorophenyl)-3-[1-(1H-pyrrolo[2,3-b]pyridin-4-ylmethyl)-1H-indol-4-yl]urea;
1-(2-Methyl-3-bromophenyl)-3-[1-(1H-pyrrolo[2,3-b]pyridin-4-ylmethyl)-1H-indol-4-yl]urea;
1-(2-Methoxy-5-chlorophenyl)-3-[1-(1H-pyrrolo[2,3-b]pyridin-4-ylmethyl)-2,3-dihydro-1H-indol-4-yl]urea.

30. The compound of claim 1, wherein the compound is:
1-Phenyl-3-[1-(1H-pyrrolo[2,3-b]pyridin-3-ylmethyl)-1H-indol-4-yl]urea;
1-(2-Chlorophenyl)-3-[1-(1H-pyrrolo[2,3-b]pyridin-3-ylmethyl)-1H-indol-4-yl]urea;
1-(3-Chlorophenyl)-3-[1-(1H-pyrrolo[2,3-b]pyridin-3-ylmethyl)-1H-indol-4-yl]urea;
1-(4-Chlorophenyl)-3-[1-(1H-pyrrolo[2,3-b]pyridin-3-ylmethyl)-1H-indol-4-yl]urea;
1-(2-Bromophenyl)-3-[1-(1H-pyrrolo[2,3-b]pyridin-3-ylmethyl)-1H-indol-4-yl]urea;
1-(3-Bromophenyl)-3-[1-(1H-pyrrolo[2,3-b]pyridin-3-ylmethyl)-1H-indol-4-yl]urea;
1-(4-Bromophenyl)-3-[1-(1H-pyrrolo[2,3-b]pyridin-3-ylmethyl)-1H-indol-4-yl]urea;
1-(2-Methoxyphenyl)-3-[1-(1H-pyrrolo[2,3-b]pyridin-3-ylmethyl)-1H-indol-4-yl]urea;
1-(3-Methoxyphenyl)-3-[1-(1H-pyrrolo[2,3-b]pyridin-3-ylmethyl)-1H-indol-4-yl]urea;
1-(4-Methoxyphenyl)-3-[1-(1H-pyrrolo[2,3-b]pyridin-3-ylmethyl)-1H-indol-4-yl]urea;
1-(2-Methylphenyl)-3-[1-(1H-pyrrolo[2,3-b]pyridin-3-ylmethyl)-1H-indol-4-yl]urea;
1-(3-Methylphenyl)-3-[1-(1H-pyrrolo[2,3-b]pyridin-3-ylmethyl)-1H-indol-4-yl]urea;
1-(4-Methylphenyl)-3-[1-(1H-pyrrolo[2,3-b]pyridin-3-ylmethyl)-1H-indol-4-yl]urea;
1-(2-Fluorophenyl)-3-[1-(1H-pyrrolo[2,3-b]pyridin-3-ylmethyl)-1H-indol-4-yl]urea;
1-(3-Fluorophenyl)-3-[1-(1H-pyrrolo[2,3-b]pyridin-3-ylmethyl)-1H-indol-4-yl]urea;
1-(4-Fluorophenyl)-3-[1-(1H-pyrrolo[2,3-b]pyridin-3-ylmethyl)-1H-indol-4-yl]urea;
1-(3-Cyanophenyl)-3-[1-(1H-pyrrolo[2,3-b]pyridin-3-ylmethyl)-1H-indol-4-yl]urea;
1-(4-Cyanophenyl)-3-[1-(1H-pyrrolo[2,3-b]pyridin-3-ylmethyl)-1H-indol-4-yl]urea;
1-(2-Trifluoromethylphenyl)-3-[1-(1H-pyrrolo[2,3-b]pyridin-3-ylmethyl)-1H-indol-4-yl]urea;
1-(3-Trifluoromethylphenyl)-3-[1-(1H-pyrrolo[2,3-b]pyridin-3-ylmethyl)-1H-indol-4-yl]urea;
1-(2-Trifluoromethoxyphenyl)-3-[1-(1H-pyrrolo[2,3-b]pyridin-3-ylmethyl)-1H-indol-4-yl]urea;
1-(2-Trifluoromethoxyphenyl)-3-[1-(1H-pyrrolo[2,3-b]pyridin-3-ylmethyl)-1H-indol-4-yl]urea;
1-(3-Trifluoromethoxyphenyl)-3-[1-(1H-pyrrolo[2,3-b]pyridin-3-ylmethyl)-1H-indol-4-yl]urea;
1-(4-Trifluoromethoxyphenyl)-3-[1-(1H-pyrrolo[2,3-b]pyridin-3-ylmethyl)-1H-indol-4-yl]urea;
1-(2-Fluoro-5-chlorophenyl)-3-[1-(1H-pyrrolo[2,3-b]pyridin-3-ylmethyl)-1H-indol-4-yl]urea;
1-(2-Fluoro-5-bromophenyl)-3-[1-(1H-pyrrolo[2,3-b]pyridin-3-ylmethyl)-1H-indol-4-yl]urea;
1-(2-Fluoro-5-methoxyphenyl)-3-[1-(1H-pyrrolo[2,3-b]pyridin-3-ylmethyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea;
1-(2,5-Dimethoxyphenyl)-3-[1-(1H-pyrrolo[2,3-b]pyridin-3-ylmethyl)-1H-indol-4-yl]urea;
1-(2-fluoro-4-chlorophenyl)-3-[1-(1H-pyrrolo[2,3-b]pyridin-3-ylmethyl)-1H-indol-4-yl]urea;
1-Phenyl-3-[1-(1H-pyrrolo[2,3-b]pyridin-4-ylmethyl)-1H-indol-4-yl]urea;
1-(2-Chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-4-ylmethyl)-1H-indol-4-yl]urea;
1-(4-Chlorophenyl)-3-[1-(1H-pyrrolo[2,3-b]pyridin-4-ylmethyl)-1H-indol-4-yl]urea;
1-(2-Bromophenyl)-3-[1-(1H-pyrrolo[2,3-b]pyridin-4-ylmethyl)-1H-indol-4-yl]urea;
1-(3-Bromophenyl)-3-[1-(1H-pyrrolo[2,3-b]pyridin-4-ylmethyl)-1H-indol-4-yl]urea;
1-(4-Bromophenyl)-3-[1-(1H-pyrrolo[2,3-b]pyridin-4-ylmethyl)-1H-indol-4-yl]urea;
1-(2-Methoxyphenyl)-3-[1-(1H-pyrrolo[2,3-b]pyridin-4-ylmethyl)-1H-indol-4-yl]urea;
1-(3-Methoxyphenyl)-3-[1-(1H-pyrrolo[2,3-b]pyridin-4-ylmethyl)-1H-indol-4-yl]urea;
1-(3-Methylphenyl)-3-[1-(1H-pyrrolo[2,3-b]pyridin-4-ylmethyl)-1H-indol-4-yl]urea;
1-(4-Methylphenyl)-3-[1-(1H-pyrrolo[2,3-b]pyridin-4-ylmethyl)-1H-indol-4-yl]urea;
1-(2-Fluorophenyl)-3-[1-(1H-pyrrolo[2,3-b]pyridin-4-ylmethyl)-1H-indol-4-yl]urea;
1-(3-Fluorophenyl)-3-[1-(1H-pyrrolo[2,3-b]pyridin-4-ylmethyl)-1H-indol-4-yl]urea;
1-(4-Fluorophenyl)-3-[1-(1H-pyrrolo[2,3-b]pyridin-4-ylmethyl)-1H-indol-4-yl]urea;
1-(3-Cyanophenyl)-3-[1-(1H-pyrrolo[2,3-b]pyridin-4-ylmethyl)-1H-indol-4-yl]urea;
1-(4-Cyanophenyl)-3-[1-(1H-pyrrolo[2,3-b]pyridin-4-ylmethyl)-1H-indol-4-yl]urea;
1-(2-Trifluoromethylphenyl)-3-[1-(1H-pyrrolo[2,3-b]pyridin-4-ylmethyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(4-Trifluoromethoxyphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(2-bromo-5-methylphenyl)-3-[1-(1H-pyrrolo[2,3-b]pyridin-4-ylmethyl)-1H-indol-4-yl]urea;
1-(2-fluoro-4-chlorophenyl)-3-[1-(1H-pyrrolo[2,3-b]pyridin-4-ylmethyl)-1H-indol-4-yl]urea;
1-(2-Methyl-3-fluorophenyl)-3-[1-(1H-pyrrolo[2,3-b]pyridin-4-ylmethyl)-1H-indol-4-yl]urea;
1-(2-Trifluoromethoxyphenyl)-3-[1-(1H-pyrrolo[2,3-b]pyridin-4-ylmethyl)-1H-indol-4-yl]urea;
1-(2-Methylphenyl)-3-[1-(1H-pyrrolo[2,3-b]pyridin-4-ylmethyl)-1H-indol-4-yl]urea; or
1-(2-Methoxy-5-chlorophenyl)-3-[1-(1H-pyrrolo[2,3-b]pyridin-4-ylmethyl)-2,3-dihydro-1H-indol-4-yl]urea.

31. The compound of claim 1, wherein the compound is 1-(2-Chlorophenyl)-3-[1-(1H-pyrrolo[2,3-b]pyridin-4-ylmethyl)-1H-indol-4-yl]urea;

1-(3-Chlorophenyl)-3-[1-(1H-pyrrolo[2,3-b]pyridin-4-yl-methyl)-1H-indol-4-yl]urea;
1-(3-Methylphenyl)-3-[1-(1H-pyrrolo[2,3-b]pyridin-4-yl-methyl)-1H-indol-4-yl]urea;
1-(2-Fluorophenyl)-3-[1-(1H-pyrrolo[2,3-b]pyridin-4-yl-methyl)-1H-indol-4-yl]urea;
1-(3-Fluorophenyl)-3-[1-(1H-pyrrolo[2,3-b]pyridin-4-yl-methyl)-1H-indol-4-yl]urea;
1-(4-Fluorophenyl)-3-[1-(1H-pyrrolo[2,3-b]pyridin-4-yl-methyl)-1H-indol-4-yl]urea;
1-(3-Cyanophenyl)-3-[1-(1H-pyrrolo[2,3-b]pyridin-4-yl-methyl)-1H-indol-4-yl]urea;
1-(3-Trifluoromethylphenyl)-3-[1-(1H-pyrrolo[2,3-b]pyridin-4-ylmethyl)-1H-indol-4-yl]urea;
1-(4-Trifluoromethylphenyl)-3-[1-(1H-pyrrolo[2,3-b]pyridin-4-ylmethyl)-1H-indol-4-yl]urea;
1-(2-Fluoro-5-chlorophenyl)-3-[1-(1H-pyrrolo[2,3-b]pyridin-4-ylmethyl)-1H-indol-4-yl]urea;
1-(2-Fluoro-5-bromophenyl)-3-[1-(1H-pyrrolo[2,3-b]pyridin-4-ylmethyl)-1H-indol-4-yl]urea;
1-(2-fluoro-4-chlorophenyl)-3-[1-(1H-pyrrolo[2,3-b]pyridin-4-ylmethyl)-1H-indol-4-yl]urea;
1-(2-Methoxyl-5-chlorophenyl)-3-[1-(1H-pyrrolo[2,3-b]pyridin-4-ylmethyl)-1H-indol-4-yl]urea;
1-(3-Chlorophenyl)-3-[1-(1H-pyrrolo[2,3-b]pyridin-3-yl-methyl)-1H-indol-4-yl]urea;
1-(4-Bromophenyl)-3-[1-(1H-pyrrolo[2,3-b]pyridin-3-yl-methyl)-1H-indol-4-yl]urea;
1-(3-Methylphenyl)-3-[1-(1H-pyrrolo[2,3-b]pyridin-3-yl-methyl)-1H-indol-4-yl]urea;
1-(2-Fluorophenyl)-3-[1-(1H-pyrrolo[2,3-b]pyridin-3-yl-methyl)-1H-indol-4-yl]urea;
1-(3-Cyanophenyl)-3-[1-(1H-pyrrolo[2,3-b]pyridin-3-yl-methyl)-1H-indol-4-yl]urea;
1-(2-Methoxyl-5-chlorophenyl)-3-[1-(1H-pyrrolo[2,3-b]pyridin-3-ylmethyl)-1H-indol-4-yl]urea; or
1-(2-Fluoro-5-bromophenyl)-3-[1-(1H-pyrrolo[2,3-b]pyridin-3-ylmethyl)-1H-indol-4-yl]urea.

32. A pharmaceutical composition comprising a therapeutically effective amount of a compound of any one of claims 1-5,6-7, and 8-31 and a pharmaceutically acceptable carrier.

33. A method for treating a patient having a condition mediated by protein kinase, wherein the condition is tumor, rheumatoid arthritis, autoimmune disease, acute inflammation, nephritis, diabetic retinitis, psoriasis, or macular degeneration, comprising administering to the patient a therapeutically effective amount of a compound of any one of claims 1-5, 6-7, and 8-31 or a pharmaceutical composition of claim 32.

34. A method of inhibiting protein kinase, wherein the protein kinase is VEGFR2, c-Met, RON, PDGFRα, PDGFRβ, c-Kit, CSF1R, EphA2, Alk, Tie-1, Tie-2, Flt3, FGFR1, FGFR2, FGFR3, FGFR4, EGFR, Her2, Abl, Aurora A, Aurora B, Aurora C, Src, Lck, IGF-1R, or IR.

35. The method of claim 33, wherein the condition is tumor, rheumatoid arthritis, autoimmune disease, acute inflammation, nephritis, diabetic retinitis, psoriasis, or macular degeneration.

* * * * *